United States Patent
Williams et al.

(10) Patent No.: US 11,404,154 B2
(45) Date of Patent: Aug. 2, 2022

(54) ACTIVITY TRENDS AND WORKOUTS

(71) Applicant: Apple Inc., Cupertino, CA (US)

(72) Inventors: Aled Hywel Williams, San Francisco, CA (US); Julie A. Arney, Los Gatos, CA (US); Jay Blahnik, San Francisco, CA (US); Gary Ian Butcher, San Jose, CA (US); Nicholas Felton, Sunnyvale, CA (US); Stephen O. Lemay, Palo Alto, CA (US); Matthew J. Sundstrom, Campell, CA (US); Molly Pray Wiebe, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/994,352

(22) Filed: Aug. 14, 2020

(65) Prior Publication Data

US 2020/0381100 A1  Dec. 3, 2020

Related U.S. Application Data

(63) Continuation of application No. 16/588,950, filed on Sep. 30, 2019, now Pat. No. 10,777,314.

(60) Provisional application No. 62/844,063, filed on May 6, 2019.

(51) Int. Cl.
| | | |
|---|---|---|
| *G16H 20/30* | (2018.01) | |
| *A61B 5/11* | (2006.01) | |
| *A63B 24/00* | (2006.01) | |
| *A61B 5/00* | (2006.01) | |
| *A63B 71/06* | (2006.01) | |

(52) U.S. Cl.
CPC ............ *G16H 20/30* (2018.01); *A61B 5/1118* (2013.01); *A61B 5/1123* (2013.01); *A61B 5/4866* (2013.01); *A61B 5/743* (2013.01); *A61B 5/7435* (2013.01); *A61B 5/7475* (2013.01); *A63B 24/0062* (2013.01); *A63B 71/0622* (2013.01)

(58) Field of Classification Search
CPC ..... G16H 20/30; A61B 5/1118; A61B 5/1123; A61B 5/4866; A61B 5/743; A61B 5/7435; A61B 5/7475; A63B 24/0062; A63B 71/0622; G06F 3/0488
See application file for complete search history.

(56) References Cited

U.S. PATENT DOCUMENTS

| | | |
|---|---|---|
| 4,205,628 A | 6/1980 | Null |
| 4,842,266 A | 6/1989 | Sweeney et al. |
| 5,423,863 A | 6/1995 | Felblinger et al. |
| 5,458,548 A | 10/1995 | Crossing et al. |

(Continued)

FOREIGN PATENT DOCUMENTS

| | | |
|---|---|---|
| CA | 2815518 A1 | 5/2012 |
| CN | 1337638 A | 2/2002 |

(Continued)

OTHER PUBLICATIONS

Applicant-Initiated Interview Summary received for U.S. Appl. No. 16/138,809, dated Dec. 16, 2020, 7 pages.

(Continued)

*Primary Examiner* — Orlando Bousono
(74) *Attorney, Agent, or Firm* — Dentons US LLP

(57) ABSTRACT

The present disclosure generally relates to computer user interfaces, and more specifically to techniques for presenting activity trends and managing workouts.

30 Claims, 29 Drawing Sheets

(56) References Cited

U.S. PATENT DOCUMENTS

| | | |
|---|---|---|
| 5,474,077 A | 12/1995 | Suga |
| 5,642,731 A | 7/1997 | Kehr |
| 5,685,723 A | 11/1997 | Ladin et al. |
| 5,788,655 A | 8/1998 | Yoshimura et al. |
| 6,013,008 A | 1/2000 | Fukushima |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,244,988 B1 | 6/2001 | Delman |
| 6,302,789 B2 | 10/2001 | Harada et al. |
| 6,416,471 B1 | 7/2002 | Kumar et al. |
| 6,603,477 B1 | 8/2003 | Tittle |
| 6,639,584 B1 | 10/2003 | Li |
| 6,705,972 B1 | 3/2004 | Takano et al. |
| 6,837,827 B1 | 1/2005 | Lee et al. |
| 6,866,613 B1 | 3/2005 | Brown et al. |
| 7,020,514 B1 | 3/2006 | Wiesel |
| 7,107,546 B2 | 9/2006 | Coulthard et al. |
| 7,128,693 B2 | 10/2006 | Brown et al. |
| 7,251,454 B2 | 7/2007 | White |
| 7,302,272 B2 | 11/2007 | Ackley |
| 7,662,065 B1 | 2/2010 | Kahn et al. |
| 7,695,406 B2 | 4/2010 | Waters |
| 7,739,148 B2 | 6/2010 | Suzuki et al. |
| 8,060,229 B2 | 11/2011 | Gupta et al. |
| 8,105,208 B2 | 1/2012 | Oleson et al. |
| 8,321,006 B1 | 11/2012 | Snyder et al. |
| 8,341,557 B2 | 12/2012 | Pisula et al. |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,725,527 B1 | 5/2014 | Kahn et al. |
| 8,768,648 B2 | 7/2014 | Panther et al. |
| 8,784,115 B1 | 7/2014 | Chuang |
| 8,784,271 B2 | 7/2014 | Brumback et al. |
| 8,825,445 B2 | 9/2014 | Hoffman et al. |
| 8,888,707 B2 | 11/2014 | Shirasaki et al. |
| 8,934,963 B1 | 1/2015 | Farazi |
| 8,990,006 B1 | 3/2015 | Wallace et al. |
| 9,020,538 B1 | 4/2015 | White et al. |
| 9,224,291 B2 | 12/2015 | Moil-Carrillo et al. |
| 9,230,076 B2 | 1/2016 | King et al. |
| 9,557,881 B1 | 1/2017 | Jain et al. |
| 9,579,060 B1 | 2/2017 | Lisy et al. |
| 9,589,445 B2 | 3/2017 | White et al. |
| 9,712,629 B2 | 7/2017 | Molettiere et al. |
| 9,721,066 B1 | 8/2017 | Funaro et al. |
| 9,730,621 B2 | 8/2017 | Cohen et al. |
| 9,734,477 B2 | 8/2017 | Weast et al. |
| 9,808,206 B1 | 11/2017 | Zhao et al. |
| 9,813,642 B1 | 11/2017 | Chen et al. |
| 9,817,481 B2 | 11/2017 | Pantelopoulos et al. |
| 9,854,653 B1 | 12/2017 | Ackmann et al. |
| 9,880,805 B1 | 1/2018 | Guralnick |
| 9,910,571 B2 | 3/2018 | Chen et al. |
| 9,940,682 B2 | 4/2018 | Hoffman et al. |
| 10,056,006 B1 | 8/2018 | Hsu-Hoffman et al. |
| 10,220,258 B2 | 3/2019 | Gu et al. |
| 10,226,195 B2 | 3/2019 | Briante et al. |
| 10,254,911 B2 | 4/2019 | Yang |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,489,508 B2 | 11/2019 | Zhai et al. |
| 10,576,327 B2 | 3/2020 | Kim et al. |
| 10,602,964 B2 | 3/2020 | Kerber |
| 10,635,267 B2 | 4/2020 | Williams |
| 10,674,942 B2 | 6/2020 | Williams et al. |
| 10,736,543 B2 | 8/2020 | Chen et al. |
| 10,762,990 B1 | 9/2020 | Schilling et al. |
| 10,777,314 B1 | 9/2020 | Williams et al. |
| 10,796,549 B2 | 10/2020 | Roberts et al. |
| 11,103,161 B2 | 8/2021 | Williams et al. |
| 11,107,569 B1 | 8/2021 | Devoto |
| 11,107,580 B1 | 8/2021 | Felton et al. |
| 11,152,100 B2 | 10/2021 | Crowley et al. |
| 11,202,598 B2 | 12/2021 | Soli et al. |
| 11,209,957 B2 | 12/2021 | Dryer et al. |
| 11,317,833 B2 | 5/2022 | Williams et al. |
| 2001/0049470 A1 | 12/2001 | Mault et al. |
| 2002/0045960 A1 | 4/2002 | Phillips et al. |
| 2002/0086774 A1 | 7/2002 | Warner |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2003/0182628 A1 | 9/2003 | Lira |
| 2003/0216971 A1 | 11/2003 | Sick et al. |
| 2003/0226695 A1 | 12/2003 | Mault |
| 2004/0014567 A1 | 1/2004 | Mendel |
| 2004/0034288 A1 | 2/2004 | Hennessy et al. |
| 2004/0077462 A1 | 4/2004 | Brown et al. |
| 2004/0077958 A1 | 4/2004 | Kato et al. |
| 2004/0128286 A1 | 7/2004 | Yasushi et al. |
| 2004/0236189 A1 | 11/2004 | Hawthorne et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0139852 A1 | 6/2005 | Chen et al. |
| 2005/0165627 A1 | 7/2005 | Fotsch et al. |
| 2005/0172311 A1 | 8/2005 | Hjelt et al. |
| 2005/0197063 A1 | 9/2005 | White et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2006/0020174 A1 | 1/2006 | Matsumura et al. |
| 2006/0052727 A1 | 3/2006 | Palestrant |
| 2006/0094969 A1 | 5/2006 | Nissila |
| 2006/0098109 A1 | 5/2006 | Ooki |
| 2006/0106741 A1 | 5/2006 | Janarthanan |
| 2006/0136173 A1 | 6/2006 | Case, Jr. et al. |
| 2006/0184800 A1 | 8/2006 | Rosenberg |
| 2006/0205564 A1 | 9/2006 | Peterson |
| 2006/0240959 A1 | 10/2006 | Huang |
| 2006/0250524 A1 | 11/2006 | Roche |
| 2007/0021269 A1 | 1/2007 | Shum |
| 2007/0032733 A1 | 2/2007 | Burton |
| 2007/0033069 A1 | 2/2007 | Rao et al. |
| 2007/0056727 A1 | 3/2007 | Newman |
| 2007/0071256 A1 | 3/2007 | Ito |
| 2007/0113726 A1 | 5/2007 | Oliver et al. |
| 2007/0136093 A1 | 6/2007 | Rankin et al. |
| 2007/0143433 A1 | 6/2007 | Daigle |
| 2007/0169614 A1 | 7/2007 | Sasaki et al. |
| 2007/0249949 A1 | 10/2007 | Hadley |
| 2007/0271065 A1 | 11/2007 | Gupta et al. |
| 2008/0012701 A1 | 1/2008 | Kass et al. |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0076637 A1 | 3/2008 | Gilley et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0141135 A1 | 6/2008 | Mason et al. |
| 2008/0146892 A1 | 6/2008 | Leboeuf et al. |
| 2008/0150731 A1 | 6/2008 | Laukkanen et al. |
| 2008/0161161 A1 | 7/2008 | Pipinich et al. |
| 2008/0161707 A1 | 7/2008 | Farringdon et al. |
| 2008/0200312 A1 | 8/2008 | Tagliabue |
| 2008/0228045 A1 | 9/2008 | Gao et al. |
| 2008/0229226 A1 | 9/2008 | Rowbottom et al. |
| 2008/0254767 A1 | 10/2008 | Jin |
| 2008/0262946 A1 | 10/2008 | Wren |
| 2008/0300110 A1 | 12/2008 | Smith et al. |
| 2009/0007017 A1 | 1/2009 | Anzures et al. |
| 2009/0012988 A1 | 1/2009 | Brown |

(56) References Cited

U.S. PATENT DOCUMENTS

| | | |
|---|---|---|
| 2009/0047645 A1 | 2/2009 | Dibenedetto et al. |
| 2009/0054743 A1 | 2/2009 | Stewart |
| 2009/0065578 A1 | 3/2009 | Peterson et al. |
| 2009/0118100 A1 | 5/2009 | Oliver et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0233771 A1 | 9/2009 | Quatrochi et al. |
| 2009/0259134 A1 | 10/2009 | Levine |
| 2009/0262088 A1 | 10/2009 | Moll-Carrillo et al. |
| 2009/0268949 A1 | 10/2009 | Ueshima et al. |
| 2009/0287103 A1 | 11/2009 | Pillai |
| 2009/0307105 A1 | 12/2009 | Lemay et al. |
| 2009/0319243 A1 | 12/2009 | Suarez-Rivera et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1 | 3/2010 | Rottler et al. |
| 2010/0064255 A1 | 3/2010 | Rottler et al. |
| 2010/0076331 A1 | 3/2010 | Chan et al. |
| 2010/0079291 A1 | 4/2010 | Kroll et al. |
| 2010/0094658 A1 | 4/2010 | Mok et al. |
| 2010/0099539 A1 | 4/2010 | Haataja |
| 2010/0121700 A1 | 5/2010 | Wigder et al. |
| 2010/0137106 A1 | 6/2010 | Oshima et al. |
| 2010/0145209 A1 | 6/2010 | Lee et al. |
| 2010/0179832 A1 | 7/2010 | Van et al. |
| 2010/0194692 A1 | 8/2010 | Orr et al. |
| 2010/0198453 A1 | 8/2010 | Dorogusker et al. |
| 2010/0222645 A1 | 9/2010 | Nadler et al. |
| 2010/0281374 A1 | 11/2010 | Schulz et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van |
| 2011/0201911 A1 | 8/2011 | Johnson et al. |
| 2011/0213276 A1 | 9/2011 | Sarussi et al. |
| 2011/0214162 A1 | 9/2011 | Brakensiek et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1 | 1/2012 | Lee et al. |
| 2012/0015779 A1 | 1/2012 | Powch et al. |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0059664 A1 | 3/2012 | Georgiev et al. |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0112908 A1 | 5/2012 | Prykaeri et al. |
| 2012/0116550 A1 | 5/2012 | Hoffman et al. |
| 2012/0150759 A1 | 6/2012 | Tarjan |
| 2012/0159380 A1 | 6/2012 | Kocienda et al. |
| 2012/0179319 A1 | 7/2012 | Gilman et al. |
| 2012/0203124 A1 | 8/2012 | Lim |
| 2012/0215115 A1 | 8/2012 | Takahashi |
| 2012/0232414 A1 | 9/2012 | Mollicone et al. |
| 2012/0232929 A1 | 9/2012 | Experton |
| 2012/0245447 A1 | 9/2012 | Karan et al. |
| 2012/0253485 A1 | 10/2012 | Weast et al. |
| 2012/0272186 A1 | 10/2012 | Kraut |
| 2012/0274508 A1 | 11/2012 | Brown et al. |
| 2012/0283524 A1 | 11/2012 | Kiani et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1* | 11/2012 | Otsubo ................ G16H 40/60 600/301 |
| 2012/0317167 A1 | 12/2012 | Rahman et al. |
| 2012/0326873 A1 | 12/2012 | Utter, II |
| 2013/0011819 A1 | 1/2013 | Horseman |
| 2013/0012788 A1 | 1/2013 | Horseman |
| 2013/0013331 A1 | 1/2013 | Horseman |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0072765 A1 | 3/2013 | Kahn et al. |
| 2013/0081083 A1 | 3/2013 | Yu et al. |
| 2013/0093715 A1 | 4/2013 | Marsden et al. |
| 2013/0095459 A1 | 4/2013 | Tran |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0144653 A1 | 6/2013 | Poe et al. |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0191647 A1 | 7/2013 | Ferrara et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0215119 A1 | 8/2013 | Vanhoecke |
| 2013/0217979 A1 | 8/2013 | Blackadar et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0262155 A1 | 10/2013 | Hinkamp |
| 2013/0263719 A1 | 10/2013 | Watterson et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0019162 A1 | 1/2014 | Skowronski et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0073486 A1 | 3/2014 | Ahmed et al. |
| 2014/0081666 A1 | 3/2014 | Teller et al. |
| 2014/0088995 A1 | 3/2014 | Damani |
| 2014/0089836 A1 | 3/2014 | Damani et al. |
| 2014/0100885 A1 | 4/2014 | Stern |
| 2014/0108998 A1 | 4/2014 | Chaudhri et al. |
| 2014/0127996 A1 | 5/2014 | Park et al. |
| 2014/0129007 A1 | 5/2014 | Utter, II |
| 2014/0129243 A1 | 5/2014 | Utter, II |

(56) References Cited

U.S. PATENT DOCUMENTS

| | | |
|---|---|---|
| 2014/0139637 A1 | 5/2014 | Mistry et al. |
| 2014/0142403 A1 | 5/2014 | Brumback et al. |
| 2014/0164611 A1 | 6/2014 | Molettiere et al. |
| 2014/0176335 A1 | 6/2014 | Brumback et al. |
| 2014/0176346 A1 | 6/2014 | Brumback et al. |
| 2014/0176475 A1 | 6/2014 | Myers et al. |
| 2014/0180595 A1 | 6/2014 | Brumback et al. |
| 2014/0180786 A1 | 6/2014 | Sullivan |
| 2014/0184422 A1 | 7/2014 | Mensinger et al. |
| 2014/0189584 A1 | 7/2014 | Weng et al. |
| 2014/0197946 A1 | 7/2014 | Park et al. |
| 2014/0200426 A1 | 7/2014 | Taub et al. |
| 2014/0200691 A1 | 7/2014 | Lee et al. |
| 2014/0218369 A1 | 8/2014 | Yuen et al. |
| 2014/0222446 A1 | 8/2014 | Ash et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0266776 A1 | 9/2014 | Miller et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278220 A1 | 9/2014 | Yuen |
| 2014/0278229 A1 | 9/2014 | Hong et al. |
| 2014/0282153 A1 | 9/2014 | Christiansen et al. |
| 2014/0288680 A1 | 9/2014 | Hoffman et al. |
| 2014/0297217 A1 | 10/2014 | Yuen |
| 2014/0310598 A1 | 10/2014 | Sprague et al. |
| 2014/0310643 A1 | 10/2014 | Karmanenko et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344687 A1 | 11/2014 | Durham et al. |
| 2014/0344723 A1 | 11/2014 | Malik et al. |
| 2014/0344951 A1 | 11/2014 | Brewer |
| 2014/0354494 A1 | 12/2014 | Katz |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0046814 A1 | 2/2015 | Haughay et al. |
| 2015/0057943 A1 | 2/2015 | Self et al. |
| 2015/0058263 A1 | 2/2015 | Landers |
| 2015/0065095 A1 | 3/2015 | Seo et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0083970 A1 | 3/2015 | Koh et al. |
| 2015/0089536 A1 | 3/2015 | Byerley |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0113553 A1 | 4/2015 | Pan |
| 2015/0118657 A1 | 4/2015 | Shrake et al. |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0130830 A1 | 5/2015 | Nagasaki et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0180746 A1 | 6/2015 | Day et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0186602 A1 | 7/2015 | Pipke et al. |
| 2015/0193217 A1 | 7/2015 | Xiang et al. |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0205947 A1 | 7/2015 | Berman et al. |
| 2015/0217163 A1 | 8/2015 | Amis et al. |
| 2015/0220883 A1 | 8/2015 | B'Far et al. |
| 2015/0230717 A1 | 8/2015 | Wan |
| 2015/0251053 A1 | 9/2015 | Hoffman et al. |
| 2015/0262499 A1 | 9/2015 | Wicka et al. |
| 2015/0269848 A1 | 9/2015 | Yuen et al. |
| 2015/0286800 A1 | 10/2015 | Kanagala et al. |
| 2015/0289823 A1 | 10/2015 | Rack-gomer et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0343709 A1 | 12/2015 | Gerstle et al. |
| 2015/0347690 A1 | 12/2015 | Keen et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0048298 A1 | 2/2016 | Choi et al. |
| 2016/0055420 A1 | 2/2016 | Karanam et al. |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0063215 A1 | 3/2016 | Zamer |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0078778 A1 | 3/2016 | Holland |
| 2016/0085937 A1 | 3/2016 | Dettinger et al. |
| 2016/0086500 A1 | 3/2016 | Kaleal, III |
| 2016/0098522 A1 | 4/2016 | Weinstein |
| 2016/0107031 A1 | 4/2016 | Palatsi et al. |
| 2016/0135731 A1 | 5/2016 | Drennan |
| 2016/0140828 A1 | 5/2016 | Deforest |
| 2016/0150978 A1 | 6/2016 | Yuen et al. |
| 2016/0156584 A1 | 6/2016 | Hum et al. |
| 2016/0180026 A1 | 6/2016 | Kim et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0210434 A1 | 7/2016 | Al-Sharif |
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0270717 A1 | 9/2016 | Luna et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0285985 A1 | 9/2016 | Molettiere et al. |
| 2016/0287177 A1 | 10/2016 | Huppert et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0314670 A1 | 10/2016 | Roberts et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328736 A1 | 11/2016 | Wang et al. |

(56) References Cited

U.S. PATENT DOCUMENTS

| | | |
|---|---|---|
| 2016/0332025 A1 | 11/2016 | Repka |
| 2016/0346607 A1 | 12/2016 | Rapfogel |
| 2016/0360972 A1 | 12/2016 | Kusakabe et al. |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0000348 A1 | 1/2017 | Karsten et al. |
| 2017/0001073 A1 | 1/2017 | Krueger et al. |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0039327 A1 | 2/2017 | Bitran et al. |
| 2017/0043214 A1 | 2/2017 | Higashi |
| 2017/0053542 A1 | 2/2017 | Wilson et al. |
| 2017/0065224 A1 | 3/2017 | Rahko et al. |
| 2017/0071551 A1 | 3/2017 | Jain et al. |
| 2017/0075551 A1 | 3/2017 | Robinson et al. |
| 2017/0095695 A1 | 4/2017 | Mangusson et al. |
| 2017/0132395 A1 | 5/2017 | Futch |
| 2017/0136297 A1 | 5/2017 | Penie |
| 2017/0143262 A1 | 5/2017 | Kurunmäki et al. |
| 2017/0147197 A1 | 5/2017 | Yang et al. |
| 2017/0153606 A1 | 6/2017 | Pitis et al. |
| 2017/0153804 A1 | 6/2017 | Kim et al. |
| 2017/0156593 A1 | 6/2017 | Ferber et al. |
| 2017/0161014 A1 | 6/2017 | Kikugawa et al. |
| 2017/0177797 A1 | 6/2017 | Kurniawan et al. |
| 2017/0181645 A1 | 6/2017 | Mahalingam et al. |
| 2017/0188893 A1 | 7/2017 | Venkatraman et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2017/0364637 A1 | 12/2017 | Kshepakaran et al. |
| 2018/0000426 A1 | 1/2018 | Li |
| 2018/0001184 A1 | 1/2018 | Tran et al. |
| 2018/0032234 A1 | 2/2018 | Michalske |
| 2018/0042559 A1 | 2/2018 | Cabrera et al. |
| 2018/0053200 A1 | 2/2018 | Cronin et al. |
| 2018/0056132 A1 | 3/2018 | Foley et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0081918 A1 | 3/2018 | Gravenites et al. |
| 2018/0107962 A1 | 4/2018 | Lundin et al. |
| 2018/0117414 A1 | 5/2018 | Miyasaka et al. |
| 2018/0120985 A1 | 5/2018 | Wallace et al. |
| 2018/0126248 A1 | 5/2018 | Dion et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0150709 A1 | 5/2018 | Ha |
| 2018/0154212 A1 | 6/2018 | Park et al. |
| 2018/0189077 A1 | 7/2018 | Gupta et al. |
| 2018/0206766 A1 | 7/2018 | Blahnik et al. |
| 2018/0211020 A1 | 7/2018 | Fukuda |
| 2018/0232494 A1 | 8/2018 | Leppala et al. |
| 2018/0239869 A1 | 8/2018 | Laing et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0272190 A1 | 9/2018 | Miura et al. |
| 2018/0279885 A1 | 10/2018 | Bulut |
| 2018/0294053 A1 | 10/2018 | Runyon et al. |
| 2018/0318647 A1 | 11/2018 | Foley et al. |
| 2018/0329584 A1 | 11/2018 | Wiiiiams et al. |
| 2018/0336530 A1 | 11/2018 | Johnson et al. |
| 2018/0339195 A1 | 11/2018 | Bernotas |
| 2018/0345078 A1 | 12/2018 | Blahnik et al. |
| 2018/0350453 A1 | 12/2018 | Nag et al. |
| 2018/0376107 A1 | 12/2018 | Shibaev et al. |
| 2019/0008467 A1 | 1/2019 | Averina et al. |
| 2019/0014205 A1 | 1/2019 | Miloseski et al. |
| 2019/0025995 A1 | 1/2019 | Williams |
| 2019/0034049 A1 | 1/2019 | Williams et al. |
| 2019/0034050 A1 | 1/2019 | Williams et al. |
| 2019/0034494 A1 | 1/2019 | Bradley et al. |
| 2019/0089701 A1 | 3/2019 | Mercury et al. |
| 2019/0090800 A1 | 3/2019 | Bosworth et al. |
| 2019/0090816 A1 | 3/2019 | Horseman |
| 2019/0104951 A1 | 4/2019 | Valys et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0184234 A1 | 6/2019 | Packles et al. |
| 2019/0192086 A1 | 6/2019 | Menon et al. |
| 2019/0206538 A1 | 7/2019 | Xing et al. |
| 2019/0209777 A1 | 7/2019 | O'Connell et al. |
| 2019/0228179 A1 | 7/2019 | Rakshit et al. |
| 2019/0228847 A1 | 7/2019 | Soli |
| 2019/0232110 A1 | 8/2019 | Williams et al. |
| 2019/0232111 A1 | 8/2019 | Williams et al. |
| 2019/0240534 A1 | 8/2019 | Black |
| 2019/0252054 A1 | 8/2019 | Dirani et al. |
| 2019/0274563 A1 | 9/2019 | Soli et al. |
| 2019/0274565 A1 | 9/2019 | Soli et al. |
| 2019/0279520 A1 | 9/2019 | Wilson et al. |
| 2019/0298230 A1 | 10/2019 | Nicholson et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0342616 A1 | 11/2019 | Domm et al. |
| 2019/0365332 A1 | 12/2019 | Fedichev et al. |
| 2019/0380624 A1 | 12/2019 | Ota et al. |
| 2019/0385708 A1 | 12/2019 | Hong et al. |
| 2019/0387982 A1 | 12/2019 | Buller |
| 2020/0014967 A1 | 1/2020 | Putnam |
| 2020/0054931 A1 | 2/2020 | Martin et al. |
| 2020/0069258 A1 | 3/2020 | Grinberg |
| 2020/0098278 A1 | 3/2020 | Doti et al. |
| 2020/0100693 A1 | 4/2020 | Velo |
| 2020/0101365 A1 | 4/2020 | Wiison et al. |
| 2020/0126673 A1 | 4/2020 | Tanabe et al. |
| 2020/0149921 A1 | 5/2020 | Hoffman et al. |
| 2020/0160961 A1 | 5/2020 | Wadhawan et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0297249 A1 | 9/2020 | Williams et al. |
| 2020/0356687 A1 | 11/2020 | Salzman et al. |
| 2020/0357522 A1 | 11/2020 | Pahwa et al. |
| 2020/0374682 A1 | 11/2020 | Newman et al. |
| 2020/0381099 A1 | 12/2020 | Crowley et al. |
| 2020/0382613 A1 | 12/2020 | Sundstrom et al. |
| 2020/0384314 A1 | 12/2020 | Lee et al. |
| 2021/0007632 A1 | 1/2021 | Blahnik et al. |

(56) References Cited

U.S. PATENT DOCUMENTS

| | | |
|---|---|---|
| 2021/0007633 A1 | 1/2021 | Blahnik et al. |
| 2021/0093919 A1 | 4/2021 | Lyke et al. |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0210182 A1 | 7/2021 | Nag et al. |
| 2021/0225482 A1 | 7/2021 | Crowley et al. |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0350900 A1 | 11/2021 | Blahnik et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375450 A1 | 12/2021 | Felton et al. |
| 2021/0379447 A1 | 12/2021 | Lee |
| 2022/0047212 A1 | 2/2022 | Balsamo et al. |
| 2022/0047918 A1 | 2/2022 | Williams et al. |
| 2022/0062707 A1 | 3/2022 | Bedekar et al. |
| 2022/0121299 A1 | 4/2022 | De Vries et al. |
| 2022/0157184 A1 | 5/2022 | Wilson et al. |

FOREIGN PATENT DOCUMENTS

| | | |
|---|---|---|
| CN | 1397904 A | 2/2003 |
| CN | 1585943 A | 2/2005 |
| CN | 101150810 A | 3/2008 |
| CN | 101541387 A | 9/2009 |
| CN | 101651870 A | 2/2010 |
| CN | 101836894 A | 9/2010 |
| CN | 101978374 A | 2/2011 |
| CN | 102339201 A | 2/2012 |
| CN | 102448555 A | 5/2012 |
| CN | 102804238 A | 11/2012 |
| CN | 102989159 A | 3/2013 |
| CN | 103154954 A | 6/2013 |
| CN | 103212197 A | 7/2013 |
| CN | 103370924 A | 10/2013 |
| CN | 103403627 A | 11/2013 |
| CN | 103561640 A | 2/2014 |
| CN | 104288983 A | 1/2015 |
| CN | 104501043 A | 4/2015 |
| CN | 104508426 A | 4/2015 |
| CN | 104815428 A | 8/2015 |
| CN | 105260078 A | 1/2016 |
| CN | 105388998 A | 3/2016 |
| CN | 105721667 A | 6/2016 |
| CN | 106537397 A | 3/2017 |
| CN | 106709235 A | 5/2017 |
| CN | 106878550 A | 6/2017 |
| EP | 1935339 A1 | 6/2008 |
| EP | 2025368 A2 | 2/2009 |
| EP | 2568409 A1 | 3/2013 |
| EP | 2921899 A2 | 9/2015 |
| EP | 3096235 A1 | 11/2016 |
| EP | 3101882 A2 | 12/2016 |
| EP | 3122038 A1 | 1/2017 |
| EP | 3557590 A1 | 10/2019 |
| JP | 6-187118 A | 7/1994 |
| JP | 2001-76078 A | 3/2001 |
| JP | 2002-190007 A | 7/2002 |
| JP | 2003-102868 A | 4/2003 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-107134 A | 4/2006 |
| JP | 2006-230679 A | 9/2006 |
| JP | 2007-260288 A | 10/2007 |
| JP | 2007-330513 A | 12/2007 |
| JP | 2008-104758 A | 5/2008 |
| JP | 2008-183339 A | 8/2008 |
| JP | 2009-78134 A | 4/2009 |
| JP | 2009-112731 A | 5/2009 |
| JP | 2010-012335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-200575 A | 10/2011 |
| JP | 2011-206323 A | 10/2011 |
| JP | 2011-259253 A | 12/2011 |
| JP | 2012-20134 A | 2/2012 |
| JP | 2012-35071 A | 2/2012 |
| JP | 2012-59264 A | 3/2012 |
| JP | 2012-524640 A | 10/2012 |
| JP | 2012-230503 A | 11/2012 |
| JP | 2012-239808 A | 12/2012 |
| JP | 2013-103020 A | 5/2013 |
| JP | 2013-117690 A | 6/2013 |
| JP | 2013-544140 A | 12/2013 |
| JP | 2014-500740 A | 1/2014 |
| JP | 2015-213686 A | 12/2015 |
| JP | 2016-502875 A | 2/2016 |
| JP | 2016-52512 A | 4/2016 |
| JP | 2016-517329 A | 6/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| JP | 2018-523554 A | 8/2018 |
| KR | 10-2006-0117570 A | 11/2006 |
| KR | 10-2011-0017076 A | 2/2011 |
| KR | 10-2012-0023657 A | 3/2012 |
| KR | 10-2012-0076559 A | 7/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2016-0028351 A | 3/2016 |
| KR | 10-2016-0076264 A | 6/2016 |
| KR | 10-2017-0003608 A | 1/2017 |
| KR | 10-2017-0029014 A | 3/2017 |
| WO | 1999/41682 A2 | 8/1999 |
| WO | 2002/27530 A2 | 4/2002 |
| WO | 2005/070289 A1 | 8/2005 |
| WO | 2009/129402 A1 | 10/2009 |
| WO | 2010/126825 A1 | 11/2010 |
| WO | 2012/021507 A2 | 2/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2013/052789 A1 | 4/2013 |
| WO | 2013/109762 A1 | 7/2013 |
| WO | 2013/109777 A1 | 7/2013 |
| WO | 2013/109916 A1 | 7/2013 |
| WO | 2013/173838 A2 | 11/2013 |
| WO | 2014/006862 A1 | 1/2014 |
| WO | 2014/200730 A1 | 12/2014 |
| WO | 2014/207294 A1 | 12/2014 |
| WO | 2014/207875 A1 | 12/2014 |
| WO | 2015/027133 A1 | 2/2015 |
| WO | 2015/179592 A1 | 11/2015 |
| WO | 2015/183828 A1 | 12/2015 |
| WO | 2015/198488 A1 | 12/2015 |
| WO | 2016/036472 A1 | 3/2016 |

(56) References Cited

FOREIGN PATENT DOCUMENTS

| WO | 2016/036582 A2 | 3/2016 |
|---|---|---|
| WO | 2017/037242 A1 | 3/2017 |
| WO | 2018/222313 A1 | 12/2018 |
| WO | 2019/017508 A1 | 1/2019 |
| WO | 2019/024603 A1 | 2/2019 |
| WO | 2019/183422 A1 | 9/2019 |
| WO | 2019/217249 A2 | 11/2019 |
| WO | 2019/231982 A1 | 12/2019 |

OTHER PUBLICATIONS

Board Decision received for Chinese Patent Application No. 201380081349.6, mailed on Nov. 23, 2020, 2 pages (1 page of English Translation and 1 page of Official Copy).
International Search Report and Written Opinion received for PCT Patent Application No. PCT/US2020/035199, dated Oct. 30, 2020, 20 pages.
Invitation to Pay Additional Fees and Partial International Search Report received for PCT Patent Application No. PCT/US2020/035164, dated Oct. 16, 2020, 14 pages.
Invitation to Pay Additional Fees received for PCT Patent Application No. PCT/US2020/035199, dated Sep. 8, 2020, 12 pages.
Non-Final Office Action received for U.S. Appl. No. 16/820,383, dated Dec. 14, 2020, 11 pages.
Non-Final Office Action received for U.S. Appl. No. 16/880,714, dated Oct. 28, 2020, 11 pages.
Non-Final Office Action received for U.S. Appl. No. 17/031,859, dated Dec. 15, 2020, 13 pages.
Notice of Allowance received for U.S. Appl. No. 16/144,753, dated Dec. 4, 2020, 22 pages.
Result of Consultation received for European Patent Application No. 18154145.9, mailed on Nov. 30, 2020, 17 pages.
Tech, Kalyani,"I See Some problems in Honor Band 5", Retrieved from: https://www.youtube.com/watch?v=5XPnYJFqajl, May 19, 2020, 1 page.
Ticks, Smartwatch,"SENBONO S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
Final Office Action received for U.S. Appl. No. 16/144,753, dated Sep. 22, 2020, 9 pages.
Notice of Allowance received for U.S. Appl. No. 16/144,864, dated Sep. 29, 2020, 2 pages.
Summons to Attend Oral Proceedings received for European Patent Application No. 18154145.9, mailed on Sep. 17, 2020, 11 pages.
International Preliminary Report on Patentability received for PCT Patent Application No. PCT/US2019/024570, dated Nov. 19, 2020, 10 pages.
Non-Final Office Action received for U.S. Appl. No. 17/031,717, dated Nov. 19, 2020, 22 pages.
Notice of Allowance received for U.S. Appl. No. 15/925,652, dated Nov. 20, 2020, 9 pages.
Office Action received for Chinese Patent Application No. 201710439448.7, dated Oct. 10, 2020, 19 pages (8 pages of English Translation and 11 pages of Official Copy).
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Notice of Allowance received for Japanese Patent Application No. 2019-162293, dated Apr. 9, 2021, 4 pages (1 page of English Translation and 3 pages of Official Copy).
Notice of Allowance received for U.S. Appl. No. 16/138,809, dated Apr. 16, 2021, 11 pages.
Office Action received for Danish Patent Application No. PA202170113, dated Apr. 15, 2021, 2 pages.
Applicant Initiated Interview Summary received for U.S. Appl. No. 15/608,848, dated Oct. 26, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
European Search Report received for European Patent Application No. 20182116.2, dated Oct. 21, 2020, 4 pages.
Notice of Allowance received for U.S. Appl. No. 16/144,735, dated Oct. 28, 2020, 13 pages.
Office Action received for Japanese Patent Application No. 2020-104679, dated Sep. 18, 2020, 13 pages (7 pages of English Translation and 6 pages of Official Copy).
Notice of Allowance received for U.S. Appl. No. 16/144,864, dated Sep. 16, 2020, 2 pages.
Office Action received for Japanese Patent Application No. 2018-014096, dated Aug. 28, 2020, 4 pages (2 pages of English Translation and 2 pages of Official Copy).
Advisory Action received for U.S. Appl. No. 16/144,864, dated Jul. 29, 2019, 6 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 16/144,849, dated Aug. 12, 2019, 5 pages.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant-Initiated Interview Summary received for U.S. Appl. No. 15/627,069, dated Nov. 4, 2019, 6 pages.
Applicant-Initiated Interview Summary received for U.S. Appl. No. 16/144,849, dated Jan. 21, 2020, 6 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Applicant-Initiated Interview Summary received for U.S. Appl. No. 15/705,849, dated Feb. 14, 2020, 3 pages.
Certificate of Examination received for Australian Patent Application No. 2018101855, dated Aug. 6, 2019, 2 pages.
Certification of Examination received for Australian Patent Application No. 2018100158, dated Oct. 23, 2018, 2 pages.
Cho H.S., "Satisfactory Innovative Smart-watch (fitbit force) . . . review after seven days of use, such as the amount of sleep and movement (improving sleep is the object of X-Blue", Online Available at: https://x-blueuv.blogspot.com/2013/12/fitbit-force.html, Dec. 3, 2013, 8 pages.
CNet, "Google Fit's automatic activity tracking is getting smarter on Android Wear", Available online at: https://www.youtube.com/watch?v=lttzlCid_d8, May 18, 2016, 1 page.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Corrected Notice of Allowance received for U.S. Appl. No. 14/732,773, dated Feb. 10, 2020, 3 pages.
Corrected Notice of Allowance received for U.S. Appl. No. 14/732,773, dated Mar. 24, 2020, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Corrected Notice of Allowance received for U.S. Appl. No. 15/600,243, dated Feb. 5, 2020, 3 pages.
Corrected Notice of Allowance received for U.S. Appl. No. 15/600,243, dated Mar. 13, 2020, 3 pages.
Corrected Notice of Allowance received for U.S. Appl. No. 15/600,243, dated Mar. 31, 2020, 5 pages.
Cyclespeed Tours, "The Most Useful Data Fields to Display on Your Garmin", Online Available at: https://www.youtube.com/watch?v=AN0Eo50yxdg, Nov. 16, 2016, 3 pages.

(56) References Cited

OTHER PUBLICATIONS

DC Rainmaker, "Garmin Fenix3 New Auto Climb Functionality", Available online at: https://www.youtube.com/watch?v=iuavOSNpVRc, Feb. 19, 2015, 1 page.
Decision to Grant received for Danish Patent Application No. PA201870379, dated Jul. 5, 2019, 2 pages.
Decision to Refuse received for European Application No. 13811085.3, dated Sep. 11, 2018, 21 pages.
Decision to Refuse received for European Patent Application No. 15771747.1, dated Aug. 10, 2018, 22 pages.
"DwProgressBar v2: Stepping and Events", davidwalsh.name/dwprogressbar-2-stepping-events-mootools-progress-bar, retrieved from the Wayback Machine, Aug. 31, 2008, 4 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.
Final Office Action received for U.S. Appl. No. 12/205,847, dated Apr. 25, 2012, 42 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/839,922, dated Dec. 14, 2016, 22 pages.
Final Office Action received for U.S. Appl. No. 15/608,848, dated Jun. 26, 2019, 27 pages.
Final Office Action received for U.S. Appl. No. 15/627,069, dated Mar. 2, 2020, 22 pages.
Final Office Action received for U.S. Appl. No. 15/925,652, dated Aug. 1, 2019, 30 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
"Fitbit App", Available online at: http://web.archive.org/web/20180114083150/https://www.fitbit.com/au/app, Jan. 14, 2018, 8 pages.
Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
"Graphs and Charts", Online available at: https://www.teachervision.com/lesson-planning/graph-chart-teacher-resources, retrieved on Dec. 12, 2018, 4 pages.
Intention to Grant received for Danish Patent Application No. PA201570668, dated Mar. 27, 2017, 2 pages.
Intention to Grant received for Danish Patent Application No. PA201870379, dated May 2, 2019, 2 pages.
International Preliminary Report on Patentability received for PCT Application No. PCT/US2016/037686, dated Mar. 1, 2018, 12 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2015/047282, dated Mar. 16, 2017, 26 pages.
International Preliminary Report on Patentability received for PCT Patent Application No. PCT/US2017/035554, dated Dec. 20, 2018, 39 pages.
International Preliminary Report on Patentability received for PCT Patent Application No. PCT/US2018/031662, dated Nov. 28, 2019, 12 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/024570, dated Aug. 8, 2019, 18 pages.
International Search Report and written Opinion received for PCT Patent Application No. PCT/US2020/025997, dated Jul. 1, 2020, 16 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2015/047282, dated Dec. 22, 2015, 7 pages.
Invitation to Pay Additional Fees received for PCT Patent Application No. PCT/US2017/035554, dated Jul. 20, 2017, 2 pages.
JenbsJourney, "Wondering About a Fitbit?", Available at: https://jenbsjourney.blogspot.kr/2013/08/wondering-about-fitbit.html, Aug. 6, 2013, 12 pages.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
"Mugs", Online Available at: https://web.archive.org/web/20151029034349/http://lemugs.com/, Oct. 29, 2015, 14 pages.
"Multi-Set Bar Chart", The Data Visualization Catalogue, Available Online at: https://datavizcatalogue.com/methods/multiset_barchart.html, Feb. 8, 2014, 3 pages.
"My CalStep", http://www.surprisesoftware.com/mycalstep/, retrieved from the Wayback Machine, May 9, 2007, 2 pages.
Non-Final Office Action received for U.S. Appl. No. 15/608,848, dated Nov. 2, 2018, 21 pages.
Non-Final Office Action received for U.S. Appl. No. 12/205,847, dated Oct. 3, 2011, 59 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Non-Final Office Action received for U.S. Appl. No. 15/183,663, dated Jul. 9, 2018, 13 pages.
Non-Final Office Action received for U.S. Appl. No. 15/600,243, dated Jun. 27, 2019, 17 pages.
Non-Final Office Action received for U.S. Appl. No. 15/608,848, dated Feb. 6, 2020, 12 pages.
Non-Final Office Action received for U.S. Appl. No. 15/627,069, dated Jun. 21, 2019, 22 pages.
Non-Final Office Action received for U.S. Appl. No. 15/705,849, dated Nov. 12, 2019, 15 pages.
Non-Final Office Action received for U.S. Appl. No. 15/925,652, dated Apr. 5, 2019, 28 pages.
Non-Final Office Action received for U.S. Appl. No. 16/138,809, dated Feb. 28, 2020, 22 pages.
Non-Final Office Action received for U.S. Appl. No. 16/144,735, dated Feb. 19, 2020, 10 pages.

(56) References Cited

OTHER PUBLICATIONS

Non-Final Office Action received for U.S. Appl. No. 16/144,753, dated Mar. 5, 2020, 9 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Dec. 18, 2018, 19 pages.
Non-Final Office Action received for U.S. Appl. No. 16/144,864, dated Jan. 31, 2020, 29 pages.
Notice of Acceptance received for Australian Patent Application No. 2015312215, dated Oct. 9, 2017, 3 pages.
Notice of Acceptance received for Australian Patent Application No. 2019201583, dated Jul. 15, 2019, 3 pages.
Notice of Allowance received for Chinese Patent Application No. 201580037927.5, dated Oct. 17, 2019, 3 pages.
Notice of Allowance received for Chinese Patent Application No. 201810105846.X, dated Feb. 18, 2020, 2 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages.
Notice of Allowance received for Japanese Patent Application No. 2016-557650, dated Apr. 9, 2019, 4 pages.
Notice of Allowance received for Japanese Patent Application No. 2018-068846, dated Dec. 9, 2019, 4 pages.
Notice of Allowance received for Korean Patent Application No. 10-2016-7014577, dated May 30, 2019, 5 pages.
Notice of Allowance received for Korean Patent Application No. 10-2016-7033638, dated May 31, 2017, 5 pages.
Notice of Allowance received for Taiwanese Patent Application No. 104128685, dated May 3, 2017, 3 pages.
Notice of Allowance received for U.S. Appl. No. 12/205,847, dated Aug. 20, 2012, 13 pages.
Notice of Allowance received for U.S. Appl. No. 14/732,773, dated Dec. 18, 2019, 21 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/183,663, dated Jan. 17, 2019, 6 pages.
Notice of Allowance received for U.S. Appl. No. 15/600,243, dated Dec. 12, 2019, 7 pages.
Notice of Allowance received for U.S. Appl. No. 15/616,480, dated Jan. 3, 2019, 8 pages.
Notice of Allowance received for U.S. Appl. No. 16/144,671, dated Feb. 10, 2020, 17 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081349.6, dated Feb. 26, 2019, 12 pages.
Office Action received for Chinese Patent Application No. 201380081349.6, dated Jan. 16, 2020, 11 pages.
Office Action received for Chinese Patent Application No. 201380081349.6, dated Jul. 15, 2019, 10 pages.
Office Action received for Chinese Patent Application No. 201580037927.5, dated Apr. 22, 2019, 9 pages.
Office Action received for Chinese Patent Application No. 201580037927.5, dated Jul. 20, 2018, 21 pages.
Office Action received for Chinese Patent Application No. 201680047983.1, dated Mar. 18, 2019, 18 pages.
Office Action received for Chinese Patent Application No. 201680047983.1, dated Nov. 28, 2019, 9 pages.
Office Action received for Chinese Patent Application No. 201710439448.7, dated Mar. 27, 2020, 13 pages.
Office Action received for Chinese Patent Application No. 201810105846.X, dated Aug. 27, 2019, 12 pages.
Office Action received for Chinese Patent Application No. 201810105846.X, dated Feb. 25, 2019, 10 pages.
Office Action received for Chinese Patent Application No. 201810105846.X, dated Nov. 28, 2019, 9 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 2, 2019, 4 pages.
Office Action Received for Danish Patent Application No. PA201670656, dated May 30, 2018, 5 pages.
Office Action Received for Danish Patent Application No. PA201670656, dated Nov. 3, 2016, 8 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770191, dated Oct. 25, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.

(56) References Cited

OTHER PUBLICATIONS

Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201970532, dated May 29, 2020, 3 pages.
Office Action received for European Patent Application No. 13811085.3, dated Apr. 20, 2018, 15 pages.
Office Action received for European Patent Application No. 16837432.0, dated Jan. 10, 2020, 7 pages.
Office Action received for European Patent Application No. 17810749.6, dated Aug. 20, 2019, 9 pages.
Office Action received for European Patent Application No. 18154145.9, dated Apr. 3, 2018, 6 pages.
Office Action received for European Patent Application No. 19721883.7, dated Jan. 10, 2020, 4 pages.
Office Action received for European Patent Application No. 15771747.1, dated Oct. 31, 2017, 7 pages.
Office Action received for German Patent Application No. 112015002326.7, dated Feb. 20, 2019, 7 pages.
Office Action received for Japanese Patent Application No. 2016-535045, dated May 12, 2017, 10 pages.
Office Action received for Japanese Patent Application No. 2016-557650, dated Apr. 13, 2018, 9 pages.
Office Action received for Japanese Patent Application No. 2016-557650, dated Aug. 10, 2017, 10 pages.
Office Action received for Japanese Patent Application No. 2016-557650, dated Nov. 9, 2018, 6 pages.
Office Action received for Japanese Patent Application No. 2018-014096, dated Jan. 6, 2020, 17 pages.
Office Action received for Japanese Patent Application No. 2018-014096, dated Jun. 29, 2018, 20 pages.
Office Action received for Japanese Patent Application No. 2018-014096, dated May 8, 2019, 14 pages.
Office Action received for Japanese Patent Application No. 2018-014096, dated Nov. 6, 2018, 15 pages.
Office Action received for Japanese Patent Application No. 2018-068846, dated Jan. 8, 2019, 6 pages.
Office Action received for Japanese Patent Application No. 2019-162293, dated Jan. 31, 2020, 8 pages.
Office Action received for Korean Patent Application No. 10-2016-7014577, dated Dec. 26, 2017, 14 pages.
Office Action received for Korean Patent Application No. 10-2016-7014577, dated Oct. 31, 2018, 11 pages.
Office Action received for Korean Patent Application No. 10-2016-7033638, dated Jan. 31, 2017, 6 pages.
Office Action received for Korean Patent Application No. 10-2019-7025538, dated Feb. 17, 2020, 12 pages.
Office Action received for Korean Patent Application No. 10-2019-7025781, dated Nov. 26, 2019, 10 pages.
Office Action received for Taiwanese Patent Application No. 104128685, dated Jan. 4, 2017, 40 pages.
Partial Supplementary European Search Report received for European Patent Application No. 17810749.6, dated Apr. 25, 2019, 8 pages.
Razykdreviews, "In Depth Review of Apple Watch Activity and Workout App", Online available at: https://www.youtube.com/watch?v=GkKI3qlK0ow>, Category: X Claims: 1-5 Category: L Reason: Internet citation/video, May 11, 2015, 1 page.
Rizknows, "Garmin Connect Mobile App—Review #2", https://www.youtube.com/watch?v=7my3wMpeRbE, Category: X Claims: 1-5 Category: L Reason: Internet citation/video, Oct. 22, 2015, 1 page.
Rizknows, "TomTom Multisport Cardio Review", Online available at: https://www.youtube.com/watch?v=WoVCzLrSN9A, Sep. 4, 2015, 1 page.
Search report and opinion received for Danish Patent Application No. PA201770191, dated Jun. 30, 2017, 9 pages.

Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201970532, dated Nov. 8, 2019, 9 pages.
Smith, "Garmin Fenix 5 Activity/Smart Watch Review", Online Available at: https://www.youtube.com/watch?v=6PkQxXQxpoU, Sep. 2, 2017, 1 page.
SportsTechGuides, "Garmin Fenix 5: How to Add Power Data Fields", Online Available at: https://www.youtube.com/watch?v=ZkPptnnXEiQ, Apr. 29, 2017, 2 pages.
SportsTechGuides, "Garmin Fenix 5: How to Set Up Run Alerts", Online Available at: https://www.youtube.com/watch?v=gSMwv8vlhB4, May 13, 2017, 2 pages.
Summons to attend oral proceedings received for European Patent Application No. 13811085.3, mailed on Jan. 26, 2018, 14 pages.
Summons to Attend Oral Proceedings received for European Patent Application No. 15771747.1, mailed on May 25, 2018, 17 pages.
Supplemental Notice of Allowance received for U.S. Appl. No. 15/616,480, dated Mar. 28, 2019, 2 pages.
Supplemental Notice of Allowance received for U.S. Appl. No. 16/144,849, dated Mar. 31, 2020, 2 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Supplementary European Search Report received for European Patent Application No. 17810749.6, dated Aug. 6, 2019, 6 pages.
Suunto Spartan Trainer Wrist HR 1.12, Online Available at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at: https://www.youtube.com/watch?v=aixfoCnS0OU, Mar. 19, 2018, 2 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-GB.pdf, Sep. 8, 2015, 44 pages.
Utilization of Galaxy S4—S Health, ChatOn and Samsung Hub, Available at: http://seeit.kr/1263, Jun. 12, 2013, 25 pages.
"Visual Pace Alarm app", Available Online at: https://apps.garmin.com/en-US/apps/3940f3a2-4847-4078-a911-d77422966c82, Oct. 19, 2016, 1 page.
Wesley, "Apple Watch Series 1", Online available at: http://toolbox.info/blog/archives/1737-unknown.html, May 28, 2015, 5 pages.
Youtube, "Apple Watch Series 3", Online available at: https://www.youtube.com/watch?v=iBPr9gEfkK8, Nov. 21, 2017, 15 pages.
Zlelik, "Garmin Fenix 5 Open Water Swimming Activity Demo", Online Available at: https://www.youtube.com/watch?v=iSVhdvw2dcs, Jun. 9, 2017, 1 page.
Applicant-Initiated Interview Summary received for U.S. Appl. No. 16/377,892, dated Mar. 26, 2021, 2 pages.
Applicant-Initiated Interview Summary received for U.S. Appl. No. 16/378,136, dated Mar. 26, 2021, 2 pages.
Applicant-Initiated Interview Summary received for U.S. Appl. No. 16/418,786, dated Mar. 30, 2021, 4 pages.
Decision on Appeal received for Korean Patent Application No. 10-2019-7025538, mailed on Feb. 24, 2021, 20 pages (4 pages of English Translation and 16 pages of Official Copy).
Notice of Allowance received for Korean Patent Application No. 10-2019-7025538, dated Mar. 10, 2021, 5 pages (2 pages of English Translation and 3 pages of Official Copy).

(56) References Cited

OTHER PUBLICATIONS

Notice of Allowance received for U.S. Appl. No. 16/144,864, dated Mar. 30, 2021, 2 pages.
Notice of Allowance received for U.S. Appl. No. 16/880,714, dated Mar. 19, 2021, 7 pages.
Office Action received for European Patent Application No. 18727543.3, dated Mar. 26, 2021, 7 pages.
Search Report and Opinion received for Danish Patent Application No. PA202070815, dated Mar. 16, 2021, 8 pages.
Final Office Action received for U.S. Appl. No. 16/418,786, dated Jan. 13, 2021, 14 pages.
Notice of Acceptance received for Australian Patent Application No. 2018268972, dated Dec. 18, 2020, 3 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/556,023, dated Jan. 13, 2021, 8 pages.
Search Report and Opinion received for Danish Patent Application No. PA202070614, dated Jan. 14, 2021, 9 pages.
Supplemental Notice of Allowance received for U.S. Appl. No. 15/925,652, dated Jan. 6, 2021, 2 pages.
Non-Final Office Action received for U.S. Appl. No. 15/608,848, dated Feb. 12, 2021, 14 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Supplemental Notice of Allowance received for U.S. Appl. No. 15/925,652, dated Feb. 17, 2021, 3 pages.
CBS This Morning, "This smart mirror puts a personal trainer in your reflection", Available at: https://www.youtube.com/watch?v=nSmTTZcpVGg, Oct. 13, 2018, 4 pages.
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Applicant Initiated Interview Summary received for U.S. Appl. No. 15/608,848, dated Apr. 13, 2021, 4 pages.
Non-Final Office Action received for U.S. Appl. No. 16/888,629, dated Mar. 31, 2021, 14 pages.
Notice of Acceptance received for Australian Patent Application No. 2021200787, dated Mar. 19, 2021, 3 pages.
Notice of Allowance received for U.S. Appl. No. 16/820,383, dated Mar. 31, 2021, 11 pages.
Office Action received for Japanese Patent Application No. 2018-184532, dated Mar. 1, 2021, 11 pages (6 pages of English Translation and 5 pages of Official Copy).
Applicant-Initiated Interview Summary received for U.S. Appl. No. 16/820,383, dated Mar. 11, 2021, 2 pages.
Non-Final Office Action received for U.S. Appl. No. 16/249,627, dated Mar. 11, 2021, 21 pages.
Notice of Acceptance received for Australian Patent Application No. 2019250251, dated Feb. 18, 2021, 3 pages.
Notice of Allowance received for U.S. Appl. No. 15/925,652, dated Mar. 9, 2021, 9 pages.
Notice of Allowance received for U.S. Appl. No. 16/144,864, dated Mar. 12, 2021, 2 pages.
Office Action received for Chinese Patent Application No. 202010606407.4, dated Jan. 27, 2021, 16 pages (7 pages of English Translation and 9 pages of Official Copy).
Office Action received for Japanese Patent Application No. 2019-563407, dated Feb. 5, 2021, 5 pages (2 pages of English Translation and 3 pages of Official Copy).
Applicant-Initiated Interview Summary received for U.S. Appl. No. 16/377,892, dated Oct. 13, 2020, 5 pages.
Applicant-Initiated Interview Summary received for U.S. Appl. No. 16/378,136, dated Oct. 13, 2020, 4 pages.
Final Office Action received for U.S. Appl. No. 15/627,069, dated Oct. 20, 2020, 25 pages.
Non-Final Office Action received for U.S. Appl. No. 16/894,309, dated Oct. 15, 2020, 24 pages.
Notice of Allowance received for U.S. Appl. No. 15/705,849, dated Oct. 16, 2020, 14 pages.
Notice of Allowance received for U.S. Appl. No. 16/556,023, dated Oct. 15, 2020, 8 pages.
Result of Consultation received for European Patent Application No. 19721883.7, mailed on Oct. 7, 2020, 3 pages.
Corrected Notice of Allowance received for U.S. Appl. No. 16/378,136, dated Jun. 11, 2021, 2 pages.
Notice of Allowance received for U.S. Appl. No. 15/627,069, dated Jun. 17, 2021, 14 pages.
Office Action received for Australian Patent Application No. 2020256383, dated Jun. 4, 2021, 3 pages.
Office Action received for European Patent Application No. 19721883.7, dated Jun. 15, 2021, 9 pages.
Applicant Initiated Interview Summary received for U.S. Appl. No. 16/894,309, dated Jan. 26, 2021, 3 pages.
Adeniyi Samuel, "How to connect a second PS4 controller to a PlayStation 4 console", Online available on:—https://www.youtube.com/watch?v=mOZX_SrNISE, May 28, 2017, 2 pages.
Allison Conor, "Working out with Fiit's wearable-powered boutique fitness classes", Online available at:—<https://www.wareable.com/wearable-tech/fiit-fitness-classes-review-3849>, May 14, 2018, 8 pages.
Applicant-Initiated Interview Summary received for U.S. Appl. No. 15/627,069, dated Jan. 22, 2021, 4 pages.
Decision to Refuse received for European Patent Application No. 17810749.6, dated Jan. 29, 2021, 24 pages.
Extended European Search Report received for European Patent Application No. 20203526.7, dated Jan. 29, 2021, 13 pages.
Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Hamilton Jim, "Peloton Tips", Online available on:—<https://www.youtube.com/watch?app=desktop&v=OneXtB0kaD4>, Oct. 22, 2015, 3 pages.
Intention to Grant received for Danish Patent Application No. PA201670656, dated Jan. 18, 2021, 2 pages.
Minutes of the Oral Proceedings received for European Patent Application No. 17810749.6, mailed on Jan. 26, 2021, 8 pages.
Notice of Allowance received for Chinese Patent Application No. 201710439448.7, dated Jan. 26, 2021, 2 pages (1 page of English Translation and 1 page of Official Copy).
Office Action received for European Patent Application No. 16837432.0, dated Jan. 27, 2021, 7 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7033834, dated Jan. 22, 2021, 13 pages (6 pages of English Translation and 7 pages of Official Copy).
Result of Consultation received for European Patent Application No. 17810749.6, mailed on Jan. 18, 2021, 3 pages.
Result of Consultation received for European Patent Application No. 17810749.6, mailed on Jan. 21, 2021, 18 pages.
Supplemental Notice of Allowance received for U.S. Appl. No. 15/925,652, dated Jan. 26, 2021, 3 pages.
Supplemental Notice of Allowance received for U.S. Appl. No. 16/556,023, dated Feb. 3, 2021, 2 pages.
Vicky's Blog, "Howto Log in to PS4 Automatically with Particular User?", Online available on:—https://www.youtube.com/watch?v=kqdlzXAvOkY, May 30, 2018, 3 pages.
YoyoDavid, "Howto Use Multiple Accounts on the PlayStation 4", Online available at:—https://www.youtube.com/watch?v=5V21obRMeKE, Jan. 9, 2014, 3 pages.
Advisory Action received for U.S. Appl. No. 16/144,864, dated Jul. 6, 2020, 6 pages.

(56) References Cited

OTHER PUBLICATIONS

Applicant-Initiated Interview Summary received for U.S. Appl. No. 15/608,848, dated May 12, 2020, 5 pages.
Applicant-Initiated Interview Summary received for U.S. Appl. No. 16/144,735, dated Jun. 18, 2020, 3 pages.
Applicant-Initiated Interview Summary received for U.S. Appl. No. 16/144,753, dated Jun. 18, 2020, 3 pages.
Applicant-Initiated Interview Summary received for U.S. Appl. No. 16/144,864, dated Apr. 29, 2020, 4 pages.
Applicant-Initiated Interview Summary received for U.S. Appl. No. 15/627,069, dated Jul. 20, 2020, 5 pages.
Applicant-Initiated Interview Summary received for U.S. Appl. No. 15/705,849, dated Jun. 29, 2020, 3 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,864, dated Jun. 22, 2020, 3 pages.
Final Office Action received for U.S. Appl. No. 15/608,848, dated Aug. 21, 2020, 15 pages.
Final Office Action received for U.S. Appl. No. 15/705,849, dated May 1, 2020, 17 pages.
Final Office Action received for U.S. Appl. No. 16/138,809, dated Aug. 27, 2020, 24 pages.
Final Office Action received for U.S. Appl. No. 16/144,735, dated May 4, 2020, 12 pages.
Final Office Action received for U.S. Appl. No. 16/144,864, dated May 28, 2020, 29 pages.
International Preliminary Report on Patentability received for PCT Patent Application No. PCT/US2019/014215, dated Aug. 6, 2020, 14 pages.
International Search Report and Written Opinion received for PCT Patent Application No. PCT/US2019/014215, dated Jun. 4, 2019, 17 pages.
International Search Report and Written Opinion received for PCT Patent Application No. PCT/US2020/025997, dated Jul. 14, 2020, 15 pages.
Invitation to Pay Additional Fees and Partial International Search Report received for PCT Patent Application No. PCT/US2019/014215, dated Apr. 12, 2019, 13 pages.
Non-Final Office Action received for U.S. Appl. No. 15/627,069, dated May 26, 2020, 25 pages.
Non-Final Office Action received for U.S. Appl. No. 15/925,652, dated Aug. 7, 2020, 39 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Non-Final Office Action received for U.S. Appl. No. 16/418,786, dated Apr. 24, 2020, 16 pages.
Notice of Acceptance received for Australian Patent Application No. 2019222943, dated May 5, 2020, 3 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,735, dated Jul. 21, 2020, 13 pages.
Notice of Allowance received for U.S. Appl. No. 16/144,864, dated Jul. 28, 2020, 27 pages.
Notice of Allowance received for U.S. Appl. No. 16/144,864, dated Sep. 10, 2020, 3 pages.
Office Action received for Australian Patent Application No. 2017277971, dated Aug. 12, 2020, 3 pages.
Office Action received for Australian Patent Application No. 2017277971, dated Jun. 3, 2020, 3 pages.
Office Action received for Australian Patent Application No. 2018268972, dated Jul. 9, 2020, 4 pages.
Office Action received for Australian Patent Application No. 2019250251, dated Aug. 6, 2020, 3 pages.
Office Action received for Chinese Patent Application No. 201380081349.6, dated Jul. 15, 2020, 9 pages (4 pages of English Translation and 5 pages of Official Copy).
Office Action received for Chinese Patent Application No. 201680047983.1, dated Jul. 1, 2020, 6 pages (3 pages of English Translation and 3 pages of Official Copy).
Office Action received for Chinese Patent Application No. 201910858933.7, dated Aug. 18, 2020, 14 pages (7 pages of English Translation and 7 pages of Official Copy).
Office Action Received for Danish Patent Application No. PA201670656, dated Jul. 1, 2020, 4 pages.
Office Action received for European Patent Application No. 19721883.7, dated May 28, 2020, 11 pages.
Office Action received for Japanese Patent Application No. 2019-044107, dated May 29, 2020, 6 pages (3 pages of English Translation and 3 pages of Official Copy).
Office Action received for Japanese Patent Application No. 2019-162293, dated Jul. 27, 2020, 9 pages (5 pages of English Translation and 4 pages of Official Copy).
Office Action received for Korean Patent Application No. 10-2019-7025538, dated Aug. 15, 2020, 8 pages (4 pages of English Translation and 4 pages of Official Copy).
Result of Consultation received for European Patent Application No. 18154145.9, mailed on Sep. 4, 2020, 3 pages.
Summons to Attend Oral Proceedings received for European Patent Application No. 17810749.6, mailed on Aug. 12, 2020, 11 pages.
Bagala et al., "Evaluation of Accelerometer-Based Fall Detection Algorithms on Real-World Falls", PloS ONE, vol. 7, No. 5, May 16, 2012, 9 pages.
Office Action received for European Patent Application No. 20182116.2, dated Nov. 6, 2020, 9 pages.
Office Action received for Korean Patent Application No. 10-2019-7025781, dated Oct. 30, 2020, 10 pages (4 pages of English Translation and 6 pages of Official Copy).
Applicant-Initiated Interview Summary received for U.S. Appl. No. 16/880,714, dated Feb. 26, 2021, 5 pages.
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
Decision to Refuse received for European Patent Application No. 18154145.9, dated Feb. 17, 2021, 20 pages.
Final Office Action received for U.S. Appl. No. 16/894,309, dated Feb. 24, 2021, 30 pages.
International Search Report and Written Opinion received for PCT Patent Application No. PCT/US2020/035164, dated Feb. 8, 2021, 26 pages.
Minutes of the Oral Proceedings received for European Patent Application No. 18154145.9, mailed on Feb. 12, 2021, 8 pages.
Notice of Acceptance received for Australian Patent Application No. 2017277971, dated Feb. 17, 2021, 3 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680047983.1, dated Feb. 1, 2021, 6 pages (3 pages of English Translation and 3 pages of Official Copy).
Office Action received for Korean Patent Application No. 10-2020-7026035, dated Feb. 19, 2021, 13 pages (6 pages of English Translation and 7 pages of Official Copy).
Applicant-Initiated Interview Summary received for U.S. Appl. No. 16/249,627, dated Jun. 2, 2021, 5 pages.
Notice of Allowance received for U.S. Appl. No. 16/378,136, dated Jun. 3, 2021, 7 pages.
Notice of Allowance received for U.S. Appl. No. 16/880,714, dated Jun. 9, 2021, 6 pages.
Office Action received for Australian Patent Application No. 2019210192, dated May 25, 2021, 4 pages.
Office Action received for European Patent Application No. 20182116.2, dated May 25, 2021, 9 pages.
Office Action received for Japanese Patent Application No. 2020-115940, dated May 7, 2021, 3 pages (1 page of English Translation and 2 pages of Official Copy).

(56) References Cited

OTHER PUBLICATIONS

Non-Final Office Action received for U.S. Appl. No. 17/192,161, dated May 13, 2021, 28 pages.
Notice of Allowance received for Chinese Patent Application No. 201680047983.1, dated Apr. 28, 2021, 3 pages (1 page of English Translation and 2 pages of Official Copy).
Notice of Allowance received for U.S. Appl. No. 16/377,892, dated May 24, 2021, 9 pages.
Office Action received for Danish Patent Application No. PA202070620, dated May 10, 2021, 5 pages.
Summons to Oral Proceedings received for European Patent Application No. 15771747.1, mailed on Apr. 29, 2021, 8 pages.
Non-Final Office Action received for U.S. Appl. No. 17/031,874, dated Dec. 28, 2020, 14 pages.
Result of Consultation received for European Patent Application No. 17810749.6, mailed on Dec. 15, 2020, 3 pages.
Search Report and Opinion received for Danish Patent Application No. PA202070620, dated Dec. 11, 2020, 9 pages.
Applicant-Initiated Interview Summary received for U.S. Appl. No. 16/894,309, dated Jun. 25, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
European Search Report received for European Patent Application No. 21165295.3, dated Jun. 18, 2021, 4 pages.
Office Action received for Chinese Patent Application No. 202010606407.4, dated Jun. 2, 2021, 12 pages (5 pages of English Translation and 7 pages of Official Copy).
Office Action received for European Patent Application No. 21165295.3, dated Jul. 1, 2021, 10 pages.
Final Office Action received for U.S. Appl. No. 17/192,161, dated Oct. 18, 2021, 22 pages.
International Search Report and Written Opinion received for PCT Patent Application No. PCT/US2021/035227, dated Oct. 6, 2021, 17 pages.
Non-Final Office Action received for U.S. Appl. No. 17/030,321, dated Oct. 18, 2021, 28 pages.
Notice of Allowance received for Japanese Patent Application No. 2020-115940, dated Oct. 22, 2021, 4 pages (1 page of English Translation and 3 pages of Official Copy).
Notice of Allowance received for U.S. Appl. No. 15/608,848, dated Oct. 29, 2021, 7 pages.
Office Action received for Australian Patent Application No. 2020239752, dated Oct. 25, 2021, 5 pages.
Office Action received for Chinese Patent Application No. 201780034203.4, dated Sep. 24, 2021, 7 pages (3 pages of English Translation and 4 pages of Official Copy).
Office Action received for Danish Patent Application No. PA202070619, dated Oct. 14, 2021, 3 pages.
Office Action received for Danish Patent Application No. PA202070815, dated Oct. 18, 2021, 2 pages.
Office Action received for Korean Patent Application No. 10-2021-7031939, dated Oct. 19, 2021, 11 pages (5 pages of English Translation and 6 pages of Official Copy).
Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Applicant-Initiated Interview Summary received for U.S. Appl. No. 17/031,704, dated Feb. 9, 2021, 3 pages.
Applicant-Initiated Interview Summary received for U.S. Appl. No. 17/031,704, dated Jun. 25, 2021, 3 pages.
Applicant-Initiated Interview Summary received for U.S. Appl. No. 17/031,717, dated Jan. 29, 2021, 5 pages.
Applicant-Initiated Interview Summary received for U.S. Appl. No. 17/031,717, dated May 17, 2021, 5 pages.
Communication of the Board of Appeal received for European Patent Application No. 15771747.1, mailed on Aug. 25, 2021, 9 pages.
Corrected Notice of Allowance received for U.S. Appl. No. 16/820,383, dated Aug. 19, 2021, 2 pages.
Final Office Action received for U.S. Appl. No. 17/030,321, dated Apr. 2, 2021, 28 pages.
Final Office Action received for U.S. Appl. No. 17/031,704, dated Apr. 1, 2021, 31 pages.
Final Office Action received for U.S. Appl. No. 17/031,717, dated Feb. 24, 2021, 23 pages.
"Gym Book—Strength Training Planner, Logger and Analyzer", GymBookApp, Available Online at: https://web.archive.org/web/20160401104508/https://gymbookapp.com/, Apr. 1, 2016, 10 pages.
Invitation to Pay Additional Fees received for PCT Patent Application No. PCT/US2021/017736, dated Jun. 15, 2021, 14 pages.
Non-Final Office Action received for U.S. Appl. No. 16/249,627, dated Aug. 31, 2021, 18 Pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Non-Final Office Action received for U.S. Appl. No. 17/031,704, dated Dec. 10, 2020, 30 pages.
Notice of Allowance received for Japanese Patent Application No. 2019-563407, dated Aug. 20, 2021, 4 pages (1 page of English Translation and 3 pages of Official Copy).
Notice of Allowance received for U.S. Appl. No. 15/608,848, dated Aug. 25, 2021, 9 pages.
Notice of Allowance received for U.S. Appl. No. 17/031,704, dated Jul. 21, 2021, 10 pages.
Notice of Allowance received for U.S. Appl. No. 17/031,727, dated Dec. 24, 2020, 12 pages.
Notice of Allowance received for U.S. Appl. No. 17/031,727, dated Jun. 25, 2021, 6 pages.
Notice of Allowance received for U.S. Appl. No. 17/031,727, dated Mar. 12, 2021, 7 pages.
Office Action received for Australian Patent Application No. 2020239740, dated Jul. 9, 2021, 4 pages.
Office Action received for Australian Patent Application No. 2020239743, dated Mar. 25, 2021, 8 pages.
Office Action received for Australian Patent Application No. 2020239748, dated Apr. 21, 2021, 6 pages.
Office Action received for Australian Patent Application No. 2020239752, dated Jun. 4, 2021, 8 pages.
Office Action received for European Patent Application No. 21168916.1, dated Aug. 23, 2021, 8 pages.
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
Search Report and Opinion received for Danish Patent Application No. PA202070619, dated Dec. 2, 2020, 11 pages.
Supplemental Notice of Allowance received for U.S. Appl. No. 17/031,727, dated Jan. 15, 2021, 2 pages.
Applicant-Initiated Interview Summary received for U.S. Appl. No. 17/192,161, dated Sep. 29, 2021, 3 pages.
International Search Report and Written Opinion received for PCT Patent Application No. PCT/US2021/017736, dated Sep. 2, 2021, 25 pages.
Notice of Allowance received for U.S. Appl. No. 16/378,136, dated Sep. 22, 2021, 7 pages.

(56) References Cited

OTHER PUBLICATIONS

Office Action received for Australian Patent Application No. 2019210192, dated Sep. 9, 2021, 4 pages.
Supplemental Notice of Allowance received for U.S. Appl. No. 16/880,714, dated Sep. 16, 2021, 2 pages.
"FAQ|SleepScore", Available Online at: https://www.sleepscore.com/sleepscore-app/faq/, Retrieved on May 26, 2021, 31 pages.
Notice of Allowance received for Japanese Patent Application No. 2020-000492, dated Jul. 16, 2021, 4 pages (1 page of English Translation and 3 pages of Official Copy).
Office Action received for Australian Patent Application No. 2020239692, dated Jul. 20, 2021, 5 pages.
Applicant-Initiated Interview Summary received for U.S. Appl. No. 17/031,717, dated Nov. 4, 2021, 5 pages.
Corrected Notice of Allowance received for U.S. Appl. No. 17/031,704, dated Nov. 2, 2021, 7 pages.
Notice of Allowance received for Japanese Patent Application No. 2020-560883, dated Oct. 29, 2021, 4 pages (1 page of English Translation and 3 pages of Official Copy).
Notice of Allowance received for U.S. Appl. No. 16/888,629, dated Nov. 9, 2021, 11 pages.
Notice of Allowance received for U.S. Appl. No. 16/894,309, dated Nov. 5, 2021, 12 pages.
Office Action received for European Patent Application No. 20721342.2, dated Nov. 4, 2021, 9 pages.
European Search Report received for European Patent Application No. 21168916.1, dated Jul. 14, 2021, 5 pages.
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7033834, dated Jul. 3, 2021, 4 pages (2 page of English Translation and 2 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Supplemental Notice of Allowance received for U.S. Appl. No. 15/627,069, dated Jul. 12, 2021, 2 pages.
Non-Final Office Action received for U.S. Appl. No. 17/031,717, dated Sep. 14, 2021, 35 pages.
Notice of Allowance received for Korean Patent Application No. 10-2020-7026035, dated Aug. 23, 2021, 4 pages (2 pages of English Translation and 2 pages of Official Copy).
Notice of Allowance received for U.S. Appl. No. 16/377,892, dated Sep. 9, 2021, 9 pages.
Office Action received for Australian Patent Application No. 2020239743, dated Sep. 3, 2021, 4 pages.
Office Action received for Australian Patent Application No. 2020239748, dated Sep. 1, 2021, 4 pages.
Office Action received for Danish Patent Application No. PA202070619, dated Aug. 27, 2021, 12 pages.
Office Action received for Japanese Patent Application No. 2019-044107, dated Jul. 30, 2021, 9 pages (5 pages of English Translation and 4 pages of Official Copy).
Office Action received for Korean Patent Application No. 10-2021-7026284, dated Aug. 31, 2021, 10 pages (4 pages of English Translation and 6 pages of Official Copy).
Applicant-Initiated Interview Summary received for U.S. Appl. No. 15/978,126, dated Jan. 19, 2021, 4 pages.
Applicant-Initiated Interview Summary received for U.S. Appl. No. 15/978,126, dated Jul. 1, 2020, 6 pages.
Applicant-Initiated Interview Summary received for U.S. Appl. No. 16/249,627, dated Oct. 6, 2021, 4 pages.
Corrected Notice of Allowance received for U.S. Appl. No. 16/820,383, dated Oct. 5, 2021, 2 pages.
Final Office Action received for U.S. Appl. No. 15/978,126, dated Sep. 30, 2020, 23 pages.
Final Office Action received for U.S. Appl. No. 17/030,318, dated Sep. 30, 2021, 28 pages.
International Preliminary Report on Patentability received for PCT Patent Application No. PCT/US2018/023303, dated Dec. 12, 2019, 8 pages.
International Search Report and Written Opinion received for PCT Patent Application No. PCT/US2018/023303, dated Jun. 19, 2018, 10 pages.
Non-Final Office Action received for U.S. Appl. No. 15/978,126, dated Mar. 26, 2020, 16 pages.
Non-Final Office Action received for U.S. Appl. No. 16/418,786, dated Oct. 4, 2021, 10 pages.
Notice of Allowance received for U.S. Appl. No. 15/978,126, dated Feb. 4, 2021, 10 pages.
Office Action received for Australian Patent Application No. 2020239740, dated Sep. 28, 2021, 5 pages.
Office Action received for Danish Patent Application No. PA202070613, dated Sep. 30, 2021, 4 pages.
Office Action received for Danish Patent Application No. PA202070614, dated Sep. 28, 2021, 4 pages.
Applicant-Initiated Interview Summary received for U.S. Appl. No. 16/888,629, dated Aug. 4, 2021, 5 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.
Corrected Notice of Allowance received for U.S. Appl. No. 16/820,383, dated Aug. 13, 2021, 2 pages.
Final Office Action received for U.S. Appl. No. 17/192,161, dated Aug. 16, 2021, 22 pages.
Notice of Acceptance received for Australian Patent Application No. 2020256383, dated Aug. 3, 2021, 3 pages.
Office Action received for Chinese Patent Application No. 201780034203.4, dated Jul. 14, 2021, 12 pages (5 pages of English Translation and 7 pages of Official Copy).
International Preliminary Report on Patentability received for PCT Patent Application No. PCT/US2020/025997, dated Nov. 18, 2021, 10 pages.
Office Action received for Chinese Patent Application No. 202110363565.6, dated Nov. 16, 2021, 16 pages (9 pages of English Translation and 7 pages of Official Copy).
Applicant Initiated Interview Summary received for U.S. Appl. No. 17/381,570, dated Apr. 26, 2022, 5 pages.
Applicant-Initiated Interview Summary received for U.S. Appl. No. 16/249,627, dated Mar. 23, 2022, 3 pages.
Applicant-Initiated Interview Summary received for U.S. Appl. No. 16/418,786, dated May 9, 2022, 2 pages.
Applicant-Initiated Interview Summary received for U.S. Appl. No. 16/820,383, dated May 10, 2022, 2 pages.
Applicant-Initiated Interview Summary received for U.S. Appl. No. 16/987,275, dated Feb. 3, 2022, 4 pages.
Applicant-Initiated Interview Summary received for U.S. Appl. No. 17/031,543, dated Apr. 21, 2022, 2 pages.
Applicant-Initiated Interview Summary received for U.S. Appl. No. 17/031,723, dated Mar. 21, 2021, 5 pages.
Applicant-Initiated Interview Summary received for U.S. Appl. No. 17/031,779, dated Mar. 10, 2022, 2 pages.
Applicant-Initiated Interview Summary received for U.S. Appl. No. 17/031,854, dated Feb. 25, 2022, 5 pages.
Applicant-Initiated Interview Summary received for U.S. Appl. No. 17/031,859, dated Feb. 25, 2022, 4 pages.
Applicant-Initiated Interview Summary received for U.S. Appl. No. 17/031,874, dated Feb. 25, 2022, 4 pages.
Applicant-Initiated Interview Summary received for U.S. Appl. No. 17/157,728, dated Feb. 3, 2022, 5 pages.
Applicant-Initiated Interview Summary received for U.S. Appl. No. 17/192,161, dated Dec. 24, 2021, 4 pages.

(56) References Cited

OTHER PUBLICATIONS

Brief Communication Regarding Oral Proceedings received for European Patent Application No. 20182116.2, dated Apr. 13, 2022, 3 pages.
Corrected Notice of Allowance received for U.S. Appl. No. 16/418,786, dated Jan. 5, 2022, 3 pages.
Corrected Notice of Allowance received for U.S. Appl. No. 16/888,629, dated Jan. 21, 2022, 2 pages.
Corrected Notice of Allowance received for U.S. Appl. No. 17/030,318, dated Jan. 24, 2022, 2 pages.
Corrected Notice of Allowance received for U.S. Appl. No. 17/031,717, dated Apr. 15, 2022, 3 pages.
Corrected Notice of Allowance received for U.S. Appl. No. 17/157,728, dated Apr. 4, 2022, 3 pages.
Corrected Notice of Allowance received for U.S. Appl. No. 17/157,728, dated Apr. 14, 2022, 6 pages.
Corrected Notice of Allowance received for U.S. Appl. No. 17/192,161, dated Apr. 22, 2022, 2 pages.
Corrected Notice of Allowance received for U.S. Appl. No. 17/192,161, dated Mar. 23, 2022, 2 pages.
Corrected Notice of Allowance received for U.S. Appl. No. 17/197,628, dated Apr. 27, 2022, 3 pages.
Decision of Appeal received for European Patent Application No. 15771747.1, dated Dec. 14, 2021, 21 pages.
Final Office Action received for U.S. Appl. No. 16/249,627, dated Feb. 14, 2022, 19 pages.
Intention to Grant received for Danish Patent Application No. PA202070615, dated Jan. 27, 2022, 2 pages.
Intention to Grant received for Danish Patent Application No. PA202070619, dated Jan. 17, 2022, 2 pages.
International Preliminary Report on Patentability received for PCT Patent Application No. PCT/US2020/035164, dated Dec. 16, 2021, 19 pages.
International Preliminary Report on Patentability received for PCT Patent Application No. PCT/US2020/035199, dated Dec. 16, 2021, 14 pages.
International Search Report and Written Opinion received for PCT Patent Application No. PCT/US2021/045375, dated Jan. 10, 2022, 21 pages.
Invitation to Pay Additional Fees received for PCT Patent Application No. PCT/US2021/045375, dated Nov. 16, 2021, 12 pages.
Minutes of the Oral Proceedings received for European Patent Application No. 15771747.1, dated Dec. 1, 2021, 4 pages.
Non-Final Office Action received for U.S. Appl. No. 16/418,786, dated Mar. 28, 2022, 14 pages.
Non-Final Office Action received for U.S. Appl. No. 16/820,383, dated Jan. 10, 2022, 18 pages.
Non-Final Office Action received for U.S. Appl. No. 16/987,275, dated Nov. 23, 2021, 17 pages.
Non-Final Office Action received for U.S. Appl. No. 17/031,543, dated Apr. 1, 2022, 9 pages.
Non-Final Office Action received for U.S. Appl. No. 17/031,723, dated Jan. 24, 2022, 17 pages.
Non-Final Office Action received for U.S. Appl. No. 17/031,779, dated Feb. 16, 2022, 17 pages.
Non-Final Office Action received for U.S. Appl. No. 17/031,854, dated Dec. 27, 2021, 13 pages.
Non-Final Office Action received for U.S. Appl. No. 17/031,859, dated Dec. 24, 2021, 16 pages.
Non-Final Office Action received for U.S. Appl. No. 17/031,874, dated Jan. 24, 2022, 18 pages.
Non-Final Office Action received for U.S. Appl. No. 17/041,415, dated Mar. 29, 2022, 11 pages.
Non-Final Office Action received for U.S. Appl. No. 17/157,728, dated Nov. 26, 2021, 18 pages.
Non-Final Office Action received for U.S. Appl. No. 17/381,570, dated Apr. 1, 2022, 29 pages.
Non-Final Office Action received for U.S. Appl. No. 17/516,537, dated May 5, 2022, 8 pages.
Notice of Acceptance received for Australian Patent Application No. 2019210192, dated Dec. 2, 2021, 3 pages.
Notice of Acceptance received for Australian Patent Application No. 2020239692, dated Apr. 6, 2022, 3 pages.
Notice of Acceptance received for Australian Patent application No. 2020239740, dated Feb. 22, 2022, 3 pages.
Notice of Acceptance received for Australian Patent Application No. 2020239743, dated Jan. 13, 2022, 3 pages.
Notice of Acceptance received for Australian Patent Application No. 2020239752, dated Jan. 31, 2022, 3 pages.
Notice of Acceptance received for Australian Patent Application No. 2021201130, dated Mar. 28, 2022, 3 pages.
Notice of Acceptance received for Australian Patent Application No. 2021203636, dated Apr. 14, 2022, 3 pages.
Notice of Allowance received for Australian Patent Application No. 2020239748, dated Mar. 7, 2022, 3 pages.
Notice of Allowance received for Chinese Patent Application No. 201380081349.6, dated Dec. 17, 2021, 2 pages (1 page of English Translation and 1 page of Official Copy).
Notice of Allowance received for Chinese Patent Application No. 201780034203.4, dated Jan. 17, 2022, 2 pages (1 page of English Translation and 1 page of Official Copy).
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Notice of Allowance received for Japanese Patent Application No. 2020-160023, dated Apr. 11, 2022, 4 pages (1 page of English Translation and 3 pages of Official Copy).
Notice of Allowance received for Japanese Patent Application No. 2020-160054, dated Apr. 4, 2022, 4 pages (1 page of English Translation and 3 pages of Official Copy).
Notice of Allowance received for Korean Patent Application No. 10-2021-7031939, dated Apr. 5, 2022, 4 pages (1 page of English Translation and 3 pages of Official Copy).
Notice of Allowance received for Korean Patent Application No. 10-2021-7038005, dated Dec. 14, 2021, 4 pages (2 pages of English Translation and 2 pages of Official Copy).
Notice of Allowance received for U.S. Appl. No. 16/418,786, dated Dec. 9, 2021, 9 pages.
Notice of Allowance received for U.S. Appl. No. 16/894,309, dated Feb. 25, 2022, 9 pages.
Notice of Allowance received for U.S. Appl. No. 17/030,318, dated Jan. 5, 2022, 8 pages.
Notice of Allowance received for U.S. Appl. No. 17/030,321, dated Apr. 1, 2022, 8 pages.
Notice of Allowance received for U.S. Appl. No. 17/031,717, dated Mar. 16, 2022, 12 pages.
Notice of Allowance received for U.S. Appl. No. 17/157,728, dated Feb. 24, 2022, 7 pages.
Notice of Allowance received for U.S. Appl. No. 17/192,161, dated Feb. 16, 2022, 8 pages.
Notice of Allowance received for U.S. Appl. No. 17/197,628, dated Mar. 23, 2022, 35 pages.
Office Action received for Australian Patent Application No. 2020239692, dated Jan. 27, 2022, 3 pages.
Office Action received for Australian Patent Application No. 2020239748, dated Feb. 11, 2022, 2 pages.
Office Action received for Australian Patent Application No. 2021201130, dated Jan. 27, 2022, 2 pages.
Office Action received for Australian Patent Application No. 2021203636, dated Mar. 23, 2022, 3 pages.
Office Action received for Chinese Patent Application No. 201910858933.7, dated Dec. 30, 2021, 9 pages (4 pages of English Translation and 5 pages of Official Copy).
Office Action received for Chinese Patent Application No. 201911401161.0, dated Jan. 24, 2022, 6 pages (3 pages of English Translation and 3 pages of Official Copy).
Office Action received for Chinese Patent Application No. 202010606407.4, dated Nov. 18, 2021, 6 pages (3 pages of English Translation and 3 pages of Official Copy).

(56) References Cited

OTHER PUBLICATIONS

Office Action received for Chinese Patent Application No. 202110783860.7, dated Mar. 10, 2022, 15 pages (5 pages of English Translation and 10 pages of Official Copy).
Office Action received for Danish Patent Application No. PA 2020 70612, dated Mar. 1, 2022, 2 pages.
Office Action received for Danish Patent Application No. PA202070614, dated Apr. 28, 2022, 4 pages.
Office Action received for Danish Patent Application No. PA202070615, dated Nov. 16, 2021, 4 pages.
Office Action received for Danish Patent Application No. PA202070616, dated Jan. 27, 2022, 2 pages.
Office Action received for Danish Patent Application No. PA202070616, dated May 5, 2022, 3 pages.
Office Action received for Danish Patent Application No. PA202070620, dated Nov. 19, 2021, 2 pages.
Office Action received for Danish Patent Application No. PA202170113, dated May 3, 2022, 2 pages.
Office Action received for European Patent Application No. 20203526.7, dated Nov. 23, 2021, 9 pages.
Office Action received for Indian Patent Application No. 202014041484, dated Dec. 8, 2021, 8 pages.
Office Action received for Indian Patent Application No. 202014041563, dated Dec. 30, 2021, 6 pages.
Office Action received for Indian Patent Application No. 202014041571, dated Dec. 17, 2021, 5 pages.
Office Action received for Japanese Patent Application No. 2020-160023, dated Jan. 17, 2022, 11 pages (6 pages of English Translation and 5 pages of Official Copy).
Office Action received for Japanese Patent Application No. 2020-160052, dated Dec. 17, 2021, 10 pages (5 pages of English Translation and 5 pages of Official Copy).
Office Action received for Japanese Patent Application No. 2020-160053, dated Jan. 31, 2022, 8 pages (4 pages of English Translation and 4 pages of Official Copy).
Office Action received for Japanese Patent Application No. 2020-160054, dated Jan. 21, 2022, 8 pages (4 pages of English Translation and 4 pages of Official Copy).
Office Action received for Japanese Patent Application No. 2020-551585, dated Jan. 6, 2022, 11 pages (5 pages of English Translation and 6 pages of Official Copy).
Office Action received for Korean Patent Application No. 10-2020-7023277, dated Jan. 26, 2022, 11 pages (5 pages of English Translation and 6 pages of Official Copy).
Search Report and Opinion received for Danish Patent Application No. PA202170113, dated Nov. 30, 2021, 9 pages.
Summons to Attend Oral Proceedings received for European Patent Application No. 13811085.3, dated Mar. 3, 2022, 3 pages.
Summons to Attend Oral Proceedings received for European Patent Application No. 20182116.2, dated Dec. 21, 2021, 7 pages.
Supplemental Notice of Allowance received for U.S. Appl. No. 16/894,309, dated Apr. 8, 2022, 3 pages.
Supplemental Notice of Allowance received for U.S. Appl. No. 16/894,309, dated Dec. 24, 2021, 2 pages.
Supplemental Notice of Allowance received for U.S. Appl. No. 16/894,309, dated Jan. 25, 2022, 2 pages.
Supplemental Notice of Allowance received for U.S. Appl. No. 17/030,318, dated Apr. 4, 2022, 2 pages.
Supplemental Notice of Allowance received for U.S. Appl. No. 17/030,318, dated Feb. 22, 2022, 2 pages.
Supplemental Notice of Allowance received for U.S. Appl. No. 17/030,318, dated Mar. 16, 2022, 2 pages.
Supplemental Notice of Allowance received for U.S. Appl. No. 17/030,321, dated Apr. 15, 2022, 2 pages.
Corrected Notice of Allowance received for U.S. Appl. No. 17/031,717, dated May 19, 2022, 3 pages.
Garmin Edge 520, Owner's Manual, Online available at https://www8.garmin.com/manuals/webhelp/edge520/EN-US/Edge_520_OM_EN-US.pdf, 2015, 24 pages.
Notice of Allowance received for U.S. Appl. No. 16/987,275, dated May 16, 2022, 7 pages.
Notice of Allowance received for U.S. Appl. No. 17/031,543, dated May 11, 2022, 6 pages.
Notice of Allowance received for U.S. Appl. No. 17/192,161, dated May 27, 2022, 8 pages.
Office Action received for Danish Patent Application No. PA202070612, dated May 10, 2022, 2 pages.
Office Action received for Danish Patent Application No. PA202070613, dated May 10, 2022, 2 pages.
Summons to Attend Oral Proceedings received for European Patent Application No. 20721342.2, dated May 20, 2022, 11 pages.
Supplemental Notice of Allowance received for U.S. Appl. No. 17/030,321, dated May 27, 2022, 2 pages.
Supplemental Notice of Allowance received for U.S. Appl. No. 17/192,161, dated May 13, 2022, 2 pages.

\* cited by examiner

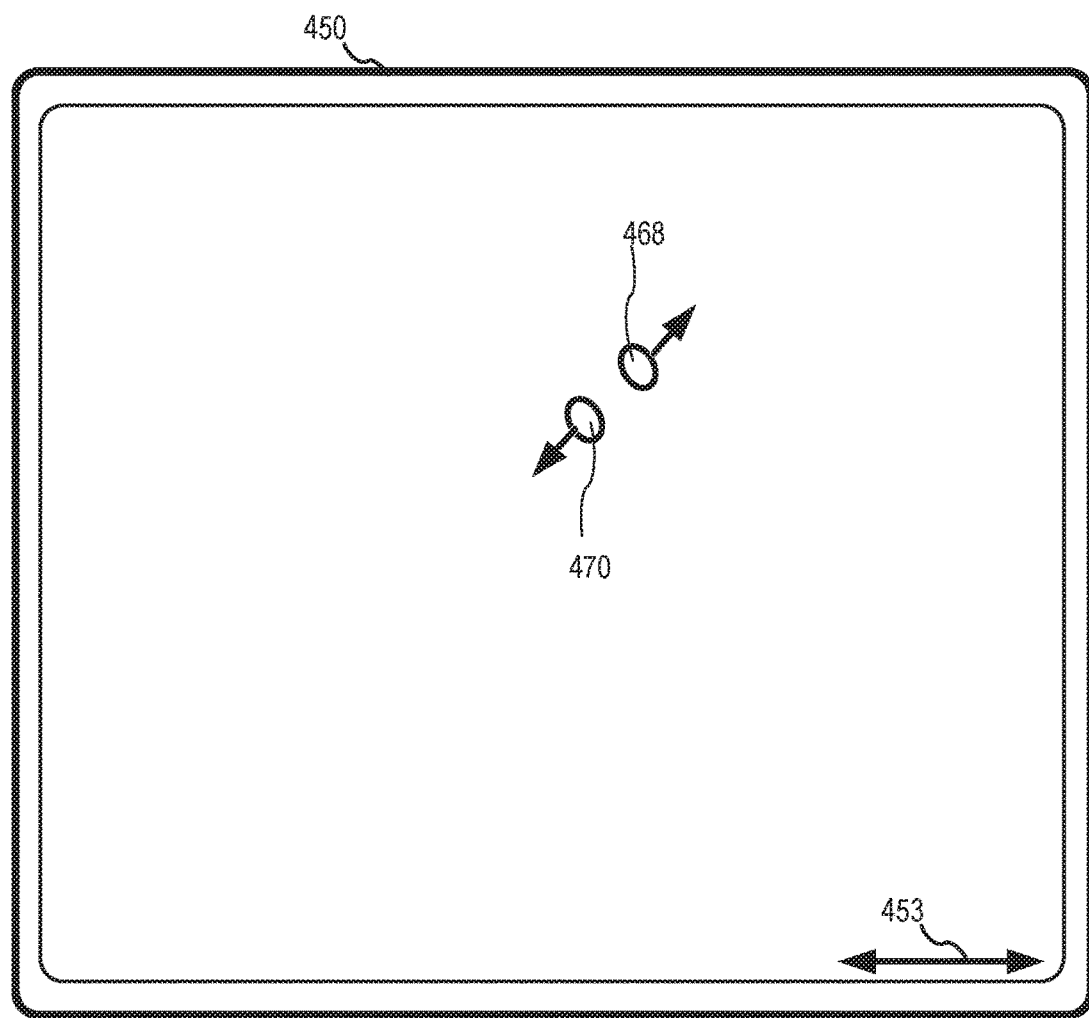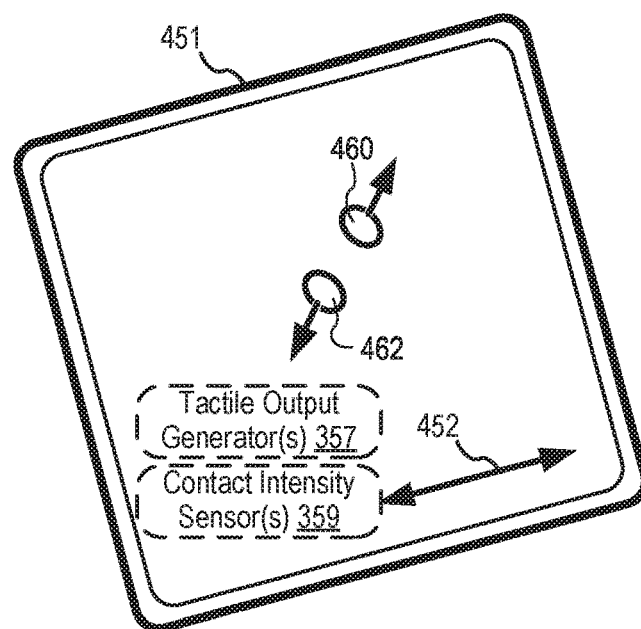
FIG. 4B

700

RECEIVE ACTIVITY DATA CORRESPONDING TO A FIRST ACTIVITY METRIC FOR A FIRST TIME PERIOD
702

RECEIVE ACTIVITY DATA CORRESPONDING TO THE FIRST ACTIVITY METRIC FOR A SECOND TIME PERIOD
704

RECEIVE A REQUEST TO DISPLAY A FIRST USER INTERFACE
706

IN RESPONSE TO RECEIVING THE REQUEST, DISPLAY THE FIRST USER INTERFACE, THE FIRST USER INTERFACE INCLUDING:
708

IN ACCORDANCE WITH A DETERMINATION THAT A RELATIONSHIP BETWEEN THE ACTIVITY DATA CORRESPONDING TO THE FIRST ACTIVITY METRIC FOR THE FIRST TIME PERIOD AND THE ACTIVITY DATA CORRESPONDING TO THE FIRST ACTIVITY METRIC FOR THE SECOND TIME PERIOD IS A FIRST TYPE, DISPLAY A REPRESENTATION OF THE FIRST ACTIVITY METRIC IN A FIRST PORTION
710

IN ACCORDANCE WITH A DETERMINATION THAT THE RELATIONSHIP BETWEEN THE ACTIVITY DATA CORRESPONDING TO THE FIRST ACTIVITY METRIC FOR THE FIRST TIME PERIOD AND THE ACTIVITY DATA CORRESPONDING TO THE FIRST ACTIVITY METRIC FOR THE SECOND TIME PERIOD IS A SECOND TYPE, DISPLAY THE REPRESENTATION OF THE FIRST ACTIVITY METRIC IN A SECOND PORTION
712

RECEIVE ACTIVITY DATA CORRESPONDING TO A THIRD ACTIVITY METRIC FOR THE FIRST TIME PERIOD
714

RECEIVE ACTIVITY DATA CORRESPONDING TO THE THIRD ACTIVITY METRIC FOR THE SECIND TIME PERIOD
716

THE FIRST USER INTERFACE INCLUDING:

IN ACCORDANCE WITH A DETERMINATION THAT A RELATIONSHIP BETWEEN THE ACTIVITY DATA CORRESPONDING TO THE THIRD ACTIVITY METRIC FOR THE FIRST TIME PERIOD AND THE ACTIVITY DATA CORRESPONDING TO THE THIRD ACTIVITY METRIC FOR THE SECOND TIME PERIOD IS THE FIRST TYPE, DISPLAY A REPRESENTATION OF THE THIRD ACTIVITY METRIC IN THE FIRST PORTION
718

IN ACCORDANCE WITH A DETERMINATION THAT THE RELATIONSHIP BETWEEN THE ACTIVITY DATA CORRESPONDING TO THE THIRD ACTIVITY METRIC FOR THE FIRST TIME PERIOD AND THE ACTIVITY DATA CORRESPONDING TO THE THIRD ACTIVITY METRIC FOR THE SECOND TIME PERIOD IS THE SECOND TYPE, DISPLAY THE REPRESENTATION OF THE FIRST ACTIVITY METRIC IN THE SECOND PORTION
720

THE FIRST USER INTERFACE INCLUDING:

A REPRESENTATION OF THE ACTIVITY DATA CORRESPONDING TO THE FIRST ACTIVITY METRIC FOR THE FIRST TIME PERIOD
810

A REPRESENTATION OF THE ACTIVITY DATA CORRESPONDING TO THE FIRST ACTIVITY METRIC FOR THE SECOND TIME PERIOD
812

A REPRESENTATION OF A COMPARISON OF THE ACTIVITY DATA CORRESPONDING TO THE FIRST ACTIVITY METRIC FOR THE FIRST TIME PERIOD AND THE ACTIVITY DATA CORRESPONDING TO THE FIRST ACTIVITY METRIC FOR THE SECOND TIME PERIOD
814

AN INDICATION FOR AN AVERAGE OF THE ACTIVITY DATA CORRESPONDING TO THE FIRST ACTIVITY METRIC FOR THE FIRST TIME PERIOD
816

AN INDICATION FOR AN AVERAGE OF THE ACTIVITY DATA CORRESPONDING TO THE FIRST ACTIVITY METRIC FOR THE SECOND TIME PERIOD
818

A PLURALITY OF FIRST-TIME-PERIOD REPRESENTATIONS FOR THE FIRST TIME PERIOD
820

A PLURALITY OF SECOND-TIME-PERIOD REPRESENTATIONS FOR THE SECOND TIME PERIOD
822

A REPRESENTATION OF A PERCENTAGE OF TIME PERIODS OF A PARTICULAR LENGTH OF THE ACTIVITY DATA CORRESPONDING TO THE FIRST ACTIVITY METRIC FOR THE FIRST TIME PERIOD FOR WHICH THE FIRST ACTIVITY METRIC MET A THREHSOLD ACTIVITY LEVEL
824

RECEIVE ACTIVITY DATA CORRESPONDING TO A FIRST ACTIVITY METRIC FOR A FIRST TIME PERIOD
902

RECEIVE ACTIVITY DATA CORRESPONDING TO THE FIRST ACTIVITY METRIC FOR A SECOND TIME PERIOD
904

RECEIVE A REQUEST TO DISPLAY A FIRST USER INTERFACE
906

IN RESPONSE TO RECEIVING THE REQUEST, DISPLAY THE FIRST USER INTERFACE, THE FIRST USER INTERFACE INCLUDING A REPRESENTATION
908

THE REPRESENTATION OF THE FIRST ACTIVITY METRIC INCLUDES, IN ACCORDANCE WITH A DETERMINATION THAT A RELATIONSHIP BETWEEN THE ACTIVITY DATA CORRESPONDING TO THE FIRST ACTIVITY METRIC FOR THE FIRST TIME PERIOD AND THE ACTIVITY DATA CORRESPONDING TO THE FIRST ACTIVITY METRIC FOR THE SECOND TIME PERIOD IS A FIRST TYPE, A FIRST COACHING INDICATION INCLUDING A PREDICTION CORRESPONDING TO WHEN THE RELATIONSHIP WILL TRANSITION FROM BEING OF THE FIRST TYPE TO BEING OF A SECOND TYPE FOR THE FIRST ACTIVITY METRIC
910

THE REPRESENTATION OF THE FIRST ACTIVITY METRIC INCLUDES, IN ACCORDANCE WITH A DETERMINATION THAT THE RELATIONSHIP IS A THIRD TYPE, A SECOND COACHING INDICATION THAT DOES NOT INCLUDE A PREDICTION CORRESPONDING TO WHEN THE RELATIONSHIP WILL TRANSITION FROM BEING OF THE THIRD TYPE TO BEING OF THE SECOND TYPE
912

FIG. 9

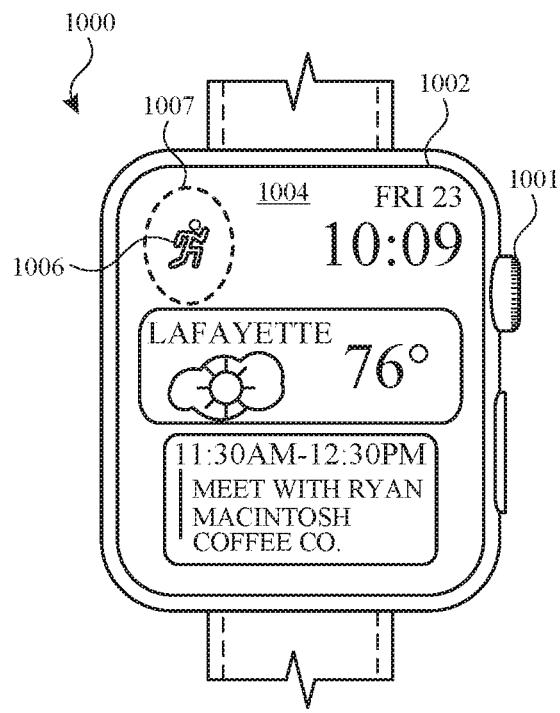
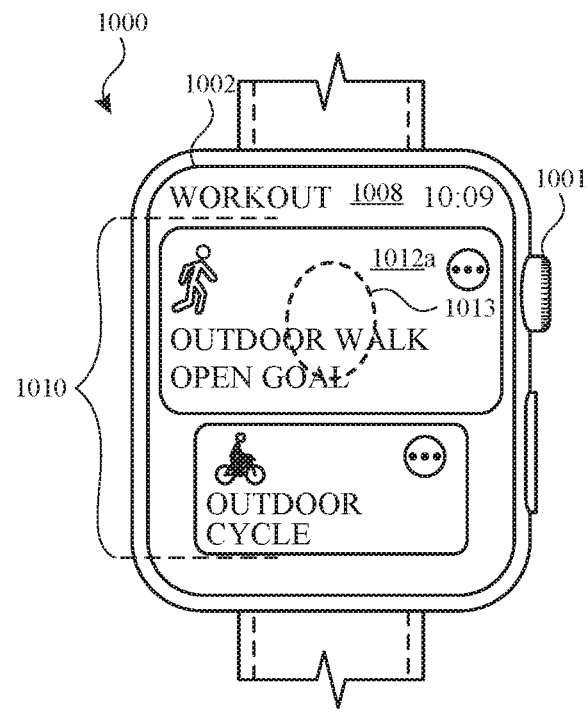
FIG. 10A FIG. 10B
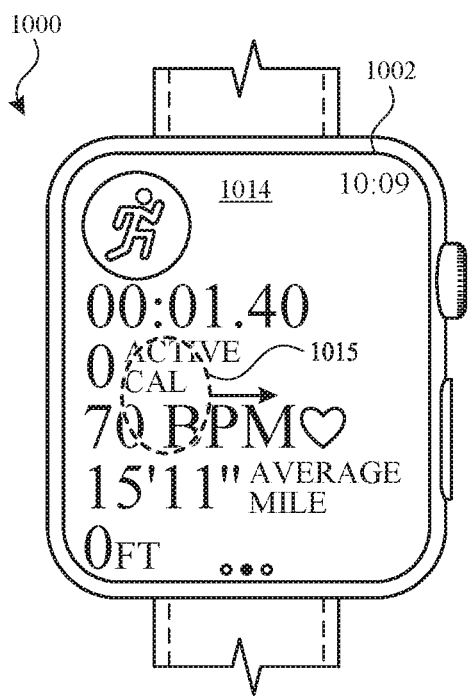
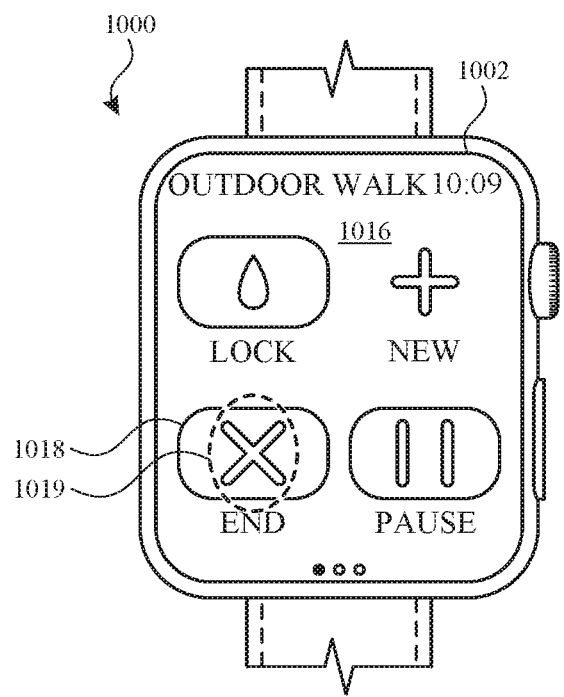
FIG. 10C FIG. 10D

1100

RECEIVE A SET OF ONE OR MORE INPUTS, THE SET OF ONE OR MORE INPUTS INCLUDING AN INPUT CORRESPONDING TO SELECTION OF THE THIRD AFFORDANCE
1110

IN RESPONSE TO RECEIVING THE SET OF ONE OR MORE INPUTS, DISPLAY A SECOND INSTANCE OF THE FIRST USER INTERFACE, WHEREIN: THE SECOND INSTANCE INCLUDES THE FIRST AFFORDANCE AND A FOURTH AFFORDANCE ASSOCIATED WITH THE SECOND PHYSICAL ACTIVITY TRACKING FUNCTION, AND THE FIRST INSTANCE DOES NOT INCLUDE AN AFFORDANCE ASSOCIATED WITH THE SECOND PHYSICAL ACTIVITY TRACKING FUNCTION
1112

RECEIVE AN INPUT CORRESPONDING TO SELECTING OF THE SECOND AFFORDANCE WITHIN THE SECOND INSTANCE OF THE FIRST USER INTERFACE
1114

IN RESPONSE TO RECEIVING THE INPUT CORRESPONDING TO SELECTION OF THE SECOND AFFORDANCE WITHIN THE SECOND INSTANCE OF THE FIRST USER INTERFACE, DISPLAY A SECOND INSTANCE OF THE SECOND USER INTERFACE THAT DOES NOT INCLUDE AN AFFORDANCE ASSOCIATED WITH THE SECOND PHYSICAL ACTIVITY TRACKING FUNCTION
1116

WHILE DISPLAYING THE SECOND INSTANCE OF THE FIRST USER INTERFACE, RECEIVE A SECOND SET OF ONE OR MORE INPUTS, THE SECOND SET INCLUDING AN INPUT CORRESPONDING TO THE FOURTH AFFORDANCE ASSOCIATED WITH THE SECOND PHYSICAL ACTIVITY TRACKING FUNCTION
1118

*FIG. 11B*

ACTIVITY TRENDS AND WORKOUTS

CROSS-REFERENCE TO RELATED APPLICATIONS

This application is a Continuation of U.S. non-Provisional application Ser. No. 16/588,950, entitled "ACTIVITY TRENDS AND WORKOUTS," filed on Sep. 30, 2019, which claims priority to U.S. Provisional Patent Application Ser. No. 62/844,063, entitled "ACTIVITY TRENDS AND WORKOUTS," filed on May 6, 2019, the contents of each of which are hereby incorporated by reference in their entirety.

FIELD

The present disclosure relates generally to computer user interfaces, and more specifically to techniques for presenting activity trends and managing workouts.

BACKGROUND

Users rely on portable multifunction devices for a variety of operations, including tracking activity. Such users may want to easily track the activity and view details related to the activity.

BRIEF SUMMARY

Some techniques for presenting activity trends and managing workouts using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for presenting activity trends and managing workouts. Such methods and interfaces optionally complement or replace other methods for presenting activity trends and managing workouts. Such methods and interfaces reduce the cognitive burden on a user and produce a more efficient human-machine interface. For battery-operated computing devices, such methods and interfaces conserve power and increase the time between battery charges.

In some examples, a method is provided for execution at an electronic device including a display device. The method comprises receiving: activity data corresponding to a first activity metric for a first time period, and activity data corresponding to the first activity metric for a second time period different from the first period of time. The method further comprises receiving a request to display a first user interface. The method further comprises, in response to receiving the request, displaying, via the display device, the first user interface including: in accordance with a determination that a relationship between the activity data corresponding to the first activity metric for the first time period and the activity data corresponding to the first activity metric for the second time period is a first type, displaying a representation of the first activity metric in a first portion of the first user interface; and in accordance with a determination that the relationship between the activity data corresponding to the first activity metric for the first time period and the activity data corresponding to the first activity metric for the second time period is a second type, displaying the representation of the first activity metric in a second portion of the first user interface different from the first portion.

In some examples, a non-transitory computer-readable storage medium storing one or more programs configured to be executed by one or more processors of an electronic device with a display device is provided. In some examples, the one or more programs include instructions for performing the method discussed above.

In some examples, an electronic device comprising: a display device; one or more processors; and memory storing one or more programs configured to be executed by the one or more processors is provided. In some examples, the one or more programs include instructions for performing the method discussed above.

In some examples, an electronic device comprising: a display device and means for performing the method discussed above.

In some examples, a non-transitory computer-readable storage medium storing one or more programs configured to be executed by one or more processors of an electronic device with a display device is provided. In some examples, the one or more programs include instructions for: receiving: activity data corresponding to a first activity metric for a first time period; and activity data corresponding to the first activity metric for a second time period different from the first period of time; receiving a request to display a first user interface; and in response to receiving the request, displaying, via the display device, the first user interface including: in accordance with a determination that a relationship between the activity data corresponding to the first activity metric for the first time period and the activity data corresponding to the first activity metric for the second time period is a first type, displaying a representation of the first activity metric in a first portion of the first user interface; and in accordance with a determination that the relationship between the activity data corresponding to the first activity metric for the first time period and the activity data corresponding to the first activity metric for the second time period is a second type, displaying the representation of the first activity metric in a second portion of the first user interface different from the first portion.

In some examples, a transitory computer-readable storage medium storing one or more programs configured to be executed by one or more processors of an electronic device with a display device is provided. In some examples, the one or more programs include instructions for: receiving: activity data corresponding to a first activity metric for a first time period; and activity data corresponding to the first activity metric for a second time period different from the first period of time; receiving a request to display a first user interface; and in response to receiving the request, displaying, via the display device, the first user interface including: in accordance with a determination that a relationship between the activity data corresponding to the first activity metric for the first time period and the activity data corresponding to the first activity metric for the second time period is a first type, displaying a representation of the first activity metric in a first portion of the first user interface; and in accordance with a determination that the relationship between the activity data corresponding to the first activity metric for the first time period and the activity data corresponding to the first activity metric for the second time period is a second type, displaying the representation of the first activity metric in a second portion of the first user interface different from the first portion.

In some examples, an electronic device, comprising: a display; one or more processors; and memory storing one or more programs configured to be executed by the one or more processors is provided. In some examples, the one or more programs include instructions for: receiving: activity data corresponding to a first activity metric for a first time period; and activity data corresponding to the first activity metric for a second time period different from the first period of time; receiving a request to display a first user interface; and in response to receiving the request, displaying, via the display device, the first user interface including: in accordance with a determination that a relationship between the activity data corresponding to the first activity metric for the first time period and the activity data corresponding to the first activity metric for the second time period is a first type, displaying a representation of the first activity metric in a first portion of the first user interface; and in accordance with a determination that the relationship between the activity data corresponding to the first activity metric for the first time period and the activity data corresponding to the first activity metric for the second time period is a second type, displaying the representation of the first activity metric in a second portion of the first user interface different from the first portion.

In some examples, an electronic device, comprising: a display is provided. In some examples, the electronic device includes: means for receiving: activity data corresponding to a first activity metric for a first time period; and activity data corresponding to the first activity metric for a second time period different from the first period of time; means for receiving a request to display a first user interface; and in response to receiving the request, means for displaying, via the display device, the first user interface including: in accordance with a determination that a relationship between the activity data corresponding to the first activity metric for the first time period and the activity data corresponding to the first activity metric for the second time period is a first type, means for displaying a representation of the first activity metric in a first portion of the first user interface; and in accordance with a determination that the relationship between the activity data corresponding to the first activity metric for the first time period and the activity data corresponding to the first activity metric for the second time period is a second type, means for displaying the representation of the first activity metric in a second portion of the first user interface different from the first portion.

In some examples, a method performed method at an electronic device including a display device is provided. In some examples, the method comprises: receiving: activity data corresponding to a first activity metric for a first time period; and activity data corresponding to the first activity metric for a second time period, wherein the first time period is a subset of the second time period; receiving a request to display a first user interface; and in response to receiving the request, displaying, via the display device, the first user interface including: representation of the activity data corresponding to the first activity metric for the first time period; a representation of the activity data corresponding to the first activity metric for the second time period; and representation of a comparison of the activity data corresponding to the first activity metric for the first time period and the activity data corresponding to the first activity metric for the second time period.

In some examples, a non-transitory computer-readable storage medium storing one or more programs configured to be executed by one or more processors of an electronic device with a display device is provided. In some examples, the one or more programs include instructions for performing the method described above.

In some examples, an electronic device comprising: a display device; one or more processors; and memory storing one or more programs configured to be executed by the one or more processors is provided. In some examples, the one or more programs include instructions for performing the method discussed above.

In some examples, an electronic device comprising: a display device and means for performing the method discussed above.

In some examples, a non-transitory computer-readable storage medium storing one or more programs configured to be executed by one or more processors of an electronic device with a display device is provided. In some examples, the one or more programs include instructions for: receiving: activity data corresponding to a first activity metric for a first time period; and activity data corresponding to the first activity metric for a second time period, wherein the first time period is a subset of the second time period; receiving a request to display a first user interface; and in response to receiving the request, displaying, via the display device, the first user interface including: a representation of the activity data corresponding to the first activity metric for the first time period; a representation of the activity data corresponding to the first activity metric for the second time period; and a representation of a comparison of the activity data corresponding to the first activity metric for the first time period and the activity data corresponding to the first activity metric for the second time period.

In some examples, a transitory computer-readable storage medium storing one or more programs configured to be executed by one or more processors of an electronic device with a display device is provided. In some examples, the one or more programs include instructions for: receiving: activity data corresponding to a first activity metric for a first time period; and activity data corresponding to the first activity metric for a second time period, wherein the first time period is a subset of the second time period; receiving a request to display a first user interface; and in response to receiving the request, displaying, via the display device, the first user interface including: a representation of the activity data corresponding to the first activity metric for the first time period; a representation of the activity data corresponding to the first activity metric for the second time period; and a representation of a comparison of the activity data corresponding to the first activity metric for the first time period and the activity data corresponding to the first activity metric for the second time period.

In some examples, an electronic device, comprising: a display device; one or more processors; and memory storing one or more programs configured to be executed by the one or more processors is provided. In some examples, the one or more programs include instructions for: receiving: activity data corresponding to a first activity metric for a first time period; and activity data corresponding to the first activity metric for a second time period, wherein the first time period is a subset of the second time period; receiving a request to display a first user interface; and in response to receiving the request, displaying, via the display device, the first user interface including: a representation of the activity data corresponding to the first activity metric for the first time period; a representation of the activity data corresponding to the first activity metric for the second time period; and a representation of a comparison of the activity data corresponding to the first activity metric for the first time period and the activity data corresponding to the first activity metric for the second time period.

In some examples, an electronic device, comprising: a display device is provided. In some examples, the electronic device includes: means for receiving: activity data corresponding to a first activity metric for a first time period; and activity data corresponding to the first activity metric for a second time period, wherein the first time period is a subset of the second time period; means for receiving a request to display a first user interface; and in response to receiving the request, means for displaying, via the display device, the first user interface including: a representation of the activity data corresponding to the first activity metric for the first time period; a representation of the activity data corresponding to the first activity metric for the second time period; and a representation of a comparison of the activity data corresponding to the first activity metric for the first time period and the activity data corresponding to the first activity metric for the second time period.

In some examples, a method to be performed at an electronic device including a display device is provided. In some examples, the method comprises: receiving: activity data corresponding to a first activity metric for a first time period; and activity data corresponding to the first activity metric for a second time period, different than the first period of time; receiving a request to display a first user interface; and in response to receiving the request, displaying, via the display device, the first user interface, the first user interface including a representation of the first activity metric, wherein the representation of the first activity metric includes: in accordance with a determination that a relationship between the activity data corresponding to the first activity metric for the first time period and the activity data corresponding to the first activity metric for the second time period is a first type, a first coaching indication including a prediction corresponding to when the relationship will transition from being of the first type to being of a second type, different from the first type, while maintaining a future level of activity for the first activity metric; and in accordance with a determination that the relationship is a third type different from the first type, a second coaching indication that does not include a prediction corresponding to when the relationship will transition from being of the third type to being of the second type.

In some examples, a non-transitory computer-readable storage medium storing one or more programs configured to be executed by one or more processors of an electronic device with a display device is provided. In some examples, the one or more programs include instructions for performing the method described above.

In some examples, an electronic device comprising: a display device; one or more processors; and memory storing one or more programs configured to be executed by the one or more processors is provided. In some examples, the one or more programs include instructions for performing the method discussed above.

In some examples, an electronic device comprising: a display device and means for performing the method discussed above.

In some examples, a non-transitory computer-readable storage medium storing one or more programs configured to be executed by one or more processors of an electronic device with a display device is provided. In some examples, the one or more programs include instructions for: receiving: activity data corresponding to a first activity metric for a first time period; and activity data corresponding to the first activity metric for a second time period, different than the first period of time; receiving a request to display a first user interface; and in response to receiving the request, displaying, via the display device, the first user interface, the first user interface including a representation of the first activity metric, wherein the representation of the first activity metric includes: in accordance with a determination that a relationship between the activity data corresponding to the first activity metric for the first time period and the activity data corresponding to the first activity metric for the second time period is a first type, a first coaching indication including a prediction corresponding to when the relationship will transition from being of the first type to being of a second type, different from the first type, while maintaining a future level of activity for the first activity metric; and in accordance with a determination that the relationship is a third type different from the first type, a second coaching indication that does not include a prediction corresponding to when the relationship will transition from being of the third type to being of the second type.

In some examples, a transitory computer-readable storage medium storing one or more programs configured to be executed by one or more processors of an electronic device with a display device is provided. In some examples, the one or more programs include instructions for: receiving: activity data corresponding to a first activity metric for a first time period; and activity data corresponding to the first activity metric for a second time period, different than the first period of time; receiving a request to display a first user interface; and in response to receiving the request, displaying, via the display device, the first user interface, the first user interface including a representation of the first activity metric, wherein the representation of the first activity metric includes: in accordance with a determination that a relationship between the activity data corresponding to the first activity metric for the first time period and the activity data corresponding to the first activity metric for the second time period is a first type, a first coaching indication including a prediction corresponding to when the relationship will transition from being of the first type to being of a second type, different from the first type, while maintaining a future level of activity for the first activity metric; and in accordance with a determination that the relationship is a third type different from the first type, a second coaching indication that does not include a prediction corresponding to when the relationship will transition from being of the third type to being of the second type.

In some examples, an electronic device, comprising: a display device; one or more processors; and memory storing one or more programs configured to be executed by the one or more processors is provided. In some examples, the one or more programs include instructions for: receiving: activity data corresponding to a first activity metric for a first time period; and activity data corresponding to the first activity metric for a second time period, different than the first period of time; receiving a request to display a first user interface; and in response to receiving the request, displaying, via the display device, the first user interface, the first user interface including a representation of the first activity metric, wherein the representation of the first activity metric includes: in accordance with a determination that a relationship between the activity data corresponding to the first activity metric for the first time period and the activity data corresponding to the first activity metric for the second time period is a first type, a first coaching indication including a prediction corresponding to when the relationship will transition from being of the first type to being of a second type, different from the first type, while maintaining a future level of activity for the first activity metric; and in accordance with a determination that the relationship is a third type different from the first type, a second coaching indication that does not include a prediction corresponding to when the relationship will transition from being of the third type to being of the second type.

In some examples, an electronic device, comprising a display device is provided. In some examples, the electronic device includes: means for receiving: activity data corresponding to a first activity metric for a first time period; and activity data corresponding to the first activity metric for a second time period, different than the first period of time; means for receiving a request to display a first user interface; and in response to receiving the request, means for displaying, via the display device, the first user interface, the first user interface including a representation of the first activity metric, wherein the representation of the first activity metric includes: in accordance with a determination that a relationship between the activity data corresponding to the first activity metric for the first time period and the activity data corresponding to the first activity metric for the second time period is a first type, a first coaching indication including a prediction corresponding to when the relationship will transition from being of the first type to being of a second type, different from the first type, while maintaining a future level of activity for the first activity metric; and in accordance with a determination that the relationship is a third type different from the first type, a second coaching indication that does not include a prediction corresponding to when the relationship will transition from being of the third type to being of the second type.

In some examples, a method performed at an electronic device including a display device is provided. The method comprises: displaying, via the display device, a first instance of a first user interface including a first set of affordances associated with physical activity tracking functions, wherein the first set of affordances includes a first affordance associated with a first physical activity tracking function; while displaying the first instance of the first user interface, receiving a user input; and in response to receiving the user input: in accordance with a determination that the user input is detected at the first affordance in the first set of affordances, launching the first physical activity tracking function; and in accordance with a determination that the user input is detected at a second affordance in the first set of affordances, displaying a second user interface that includes a third affordance associated with a second physical activity tracking function; receiving a set of one or more inputs, the set of one or more inputs including an input corresponding to selection of the third affordance; and in response to receiving the set of one or more inputs, displaying a second instance of first user interface, wherein: the second instance of the first user interface includes the first affordance and a fourth affordance associated with the second physical activity tracking function, and the first instance of the first user interface does not include an affordance associated with the second physical activity tracking function.

In some examples, a non-transitory computer-readable storage medium storing one or more programs configured to be executed by one or more processors of an electronic device with a display device is provided. In some examples, the one or more programs include instructions for performing the method described above.

In some examples, an electronic device comprising: a display device; one or more processors; and memory storing one or more programs configured to be executed by the one or more processors is provided. In some examples, the one or more programs include instructions for performing the method discussed above.

In some examples, an electronic device comprising: a display device and means for performing the method discussed above.

In some examples, a non-transitory computer-readable storage medium storing one or more programs configured to be executed by one or more processors of an electronic device with a display device is provided. The one or more programs include instructions for: displaying, via the display device, a first instance of a first user interface including a first set of affordances associated with physical activity tracking functions, wherein the first set of affordances includes a first affordance associated with a first physical activity tracking function; while displaying the first instance of the first user interface, receiving a user input; and in response to receiving the user input: in accordance with a determination that the user input is detected at the first affordance in the first set of affordances, launching the first physical activity tracking function; and in accordance with a determination that the user input is detected at a second affordance in the first set of affordances, displaying a second user interface that includes a third affordance associated with a second physical activity tracking function; receiving a set of one or more inputs, the set of one or more inputs including an input corresponding to selection of the third affordance; and in response to receiving the set of one or more inputs, displaying a second instance of first user interface, wherein: the second instance of the first user interface includes the first affordance and a fourth affordance associated with the second physical activity tracking function, and the first instance of the first user interface does not include an affordance associated with the second physical activity tracking function.

In some examples, a transitory computer-readable storage medium storing one or more programs configured to be executed by one or more processors of an electronic device with a display device is provided. The one or more programs include instructions for: displaying, via the display device, a first instance of a first user interface including a first set of affordances associated with physical activity tracking functions, wherein the first set of affordances includes a first affordance associated with a first physical activity tracking function; while displaying the first instance of the first user interface, receiving a user input; and in response to receiving the user input: in accordance with a determination that the user input is detected at the first affordance in the first set of affordances, launching the first physical activity tracking function; and in accordance with a determination that the user input is detected at a second affordance in the first set of affordances, displaying a second user interface that includes a third affordance associated with a second physical activity tracking function; receiving a set of one or more inputs, the set of one or more inputs including an input corresponding to selection of the third affordance; and in response to receiving the set of one or more inputs, displaying a second instance of first user interface, wherein: the second instance of the first user interface includes the first affordance and a fourth affordance associated with the second physical activity tracking function, and the first instance of the first user interface does not include an affordance associated with the second physical activity tracking function.

In some examples, an electronic device, comprising: a display device; one or more processors; and memory storing one or more programs configured to be executed by the one or more processors is provided. The one or more programs include instructions for: displaying, via the display device, a first instance of a first user interface including a first set of affordances associated with physical activity tracking functions, wherein the first set of affordances includes a first affordance associated with a first physical activity tracking function; while displaying the first instance of the first user interface, receiving a user input; and in response to receiving the user input: in accordance with a determination that the user input is detected at the first affordance in the first set of affordances, launching the first physical activity tracking function; and in accordance with a determination that the user input is detected at a second affordance in the first set of affordances, displaying a second user interface that includes a third affordance associated with a second physical activity tracking function; receiving a set of one or more inputs, the set of one or more inputs including an input corresponding to selection of the third affordance; and in response to receiving the set of one or more inputs, displaying a second instance of first user interface, wherein: the second instance of the first user interface includes the first affordance and a fourth affordance associated with the second physical activity tracking function, and the first instance of the first user interface does not include an affordance associated with the second physical activity tracking function.

In some examples, an electronic device, comprising a display device is provided. The electronic device further comprises: means displaying, via the display device, a first instance of a first user interface including a first set of affordances associated with physical activity tracking functions, wherein the first set of affordances includes a first affordance associated with a first physical activity tracking function; while displaying the first instance of the first user interface, means for receiving a user input; and in response to receiving the user input: in accordance with a determination that the user input is detected at the first affordance in the first set of affordances, means for launching the first physical activity tracking function; and in accordance with a determination that the user input is detected at a second affordance in the first set of affordances, means for displaying a second user interface that includes a third affordance associated with a second physical activity tracking function; means for receiving a set of one or more inputs, the set of one or more inputs including an input corresponding to selection of the third affordance; and in response to receiving the set of one or more inputs, means for displaying a second instance of first user interface, wherein: the second instance of the first user interface includes the first affordance and a fourth affordance associated with the second physical activity tracking function, and the first instance of the first user interface does not include an affordance associated with the second physical activity tracking function.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for presenting activity trends and managing workouts, thereby increasing the effectiveness, efficiency, and user satisfaction with such devices. Such methods and interfaces can complement or replace other methods for presenting activity trends and managing workouts.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIGS. 7A-7B are a flow diagram illustrating a method for presenting activity trends using an electronic device in accordance with some embodiments.

FIGS. 8A-8B are a flow diagram illustrating a method for presenting activity trends using an electronic device in accordance with some embodiments.

FIG. 9 is a flow diagram illustrating a method for presenting activity trends using an electronic device in accordance with some embodiments.

FIG. 10A depicts an electronic device displaying a watch face user interface via a display device.

FIG. 10B depicts an electronic device displaying a workout platter user interface via a display device.

FIG. 10C depicts an electronic device displaying a walk user interface via a display device.

FIG. 10D depicts an electronic device displaying a control user interface via a display device.

FIGS. 11A-11B are a flow diagram illustrating methods of organizing workouts in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

Figure 8A:
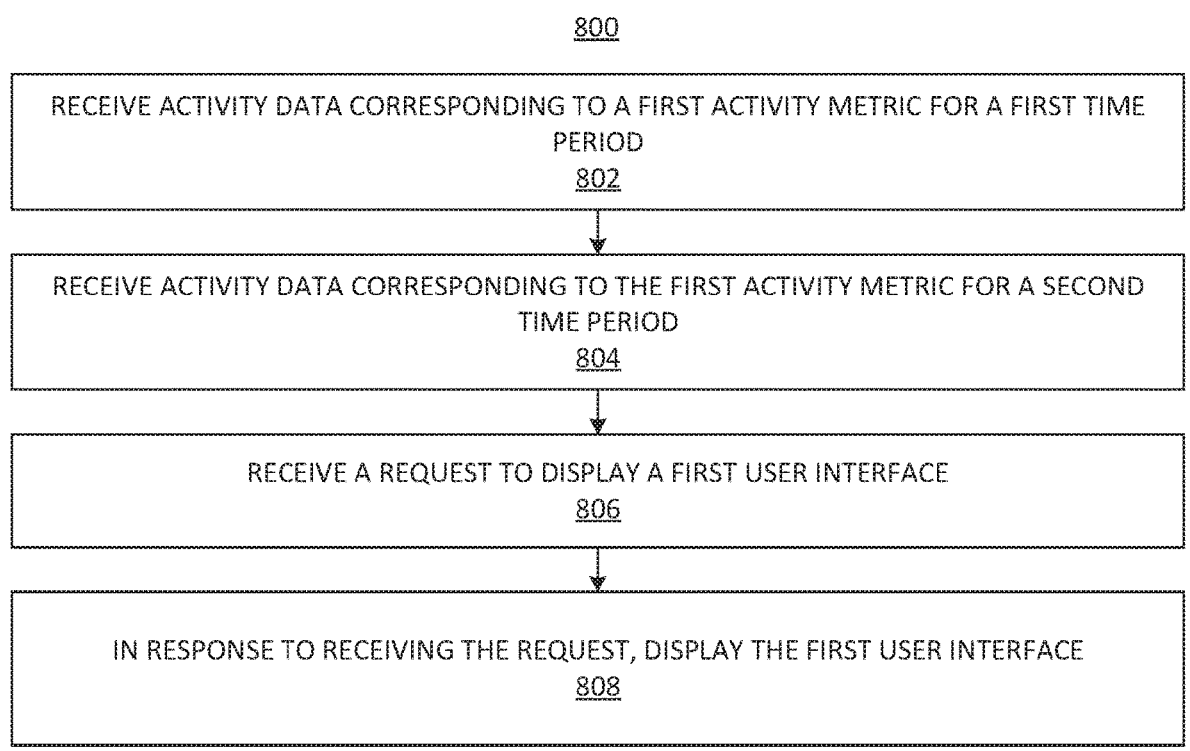

There is a need for electronic devices that provide efficient methods and interfaces for presenting activity trends and managing workouts. Below, FIGS. 1A-1B, 2, 3, 4A-4B, and 5A-5B provide a description of exemplary devices for performing the techniques for managing event notifications. FIGS. 6A-6I illustrate exemplary user interfaces for presenting activity trends. The user interfaces in FIGS. 6A-6I are used to illustrate the processes described below, including the processes in FIGS. 7A-7B, 8A-8B, and 9. FIGS. 7A-7B are a flow diagram illustrating methods of presenting activity trends in accordance with some embodiments. FIGS. 8A-8B are a flow diagram illustrating methods of presenting activity trends in accordance with some embodiments. FIG. 9 is a flow diagram illustrating methods of presenting activity trends in accordance with some embodiments. FIGS. 10A-10N illustrate exemplary user interfaces for managing workouts. The user interfaces in FIGS. 10A-ION are used to illustrate the processes described below, including the processes in FIGS. 11A-11B. FIGS. 11A-11B are a flow diagram illustrating methods of organizing workouts in accordance with some embodiments. FIGS. 12A-12F illustrate exemplary user interfaces for displaying awards.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
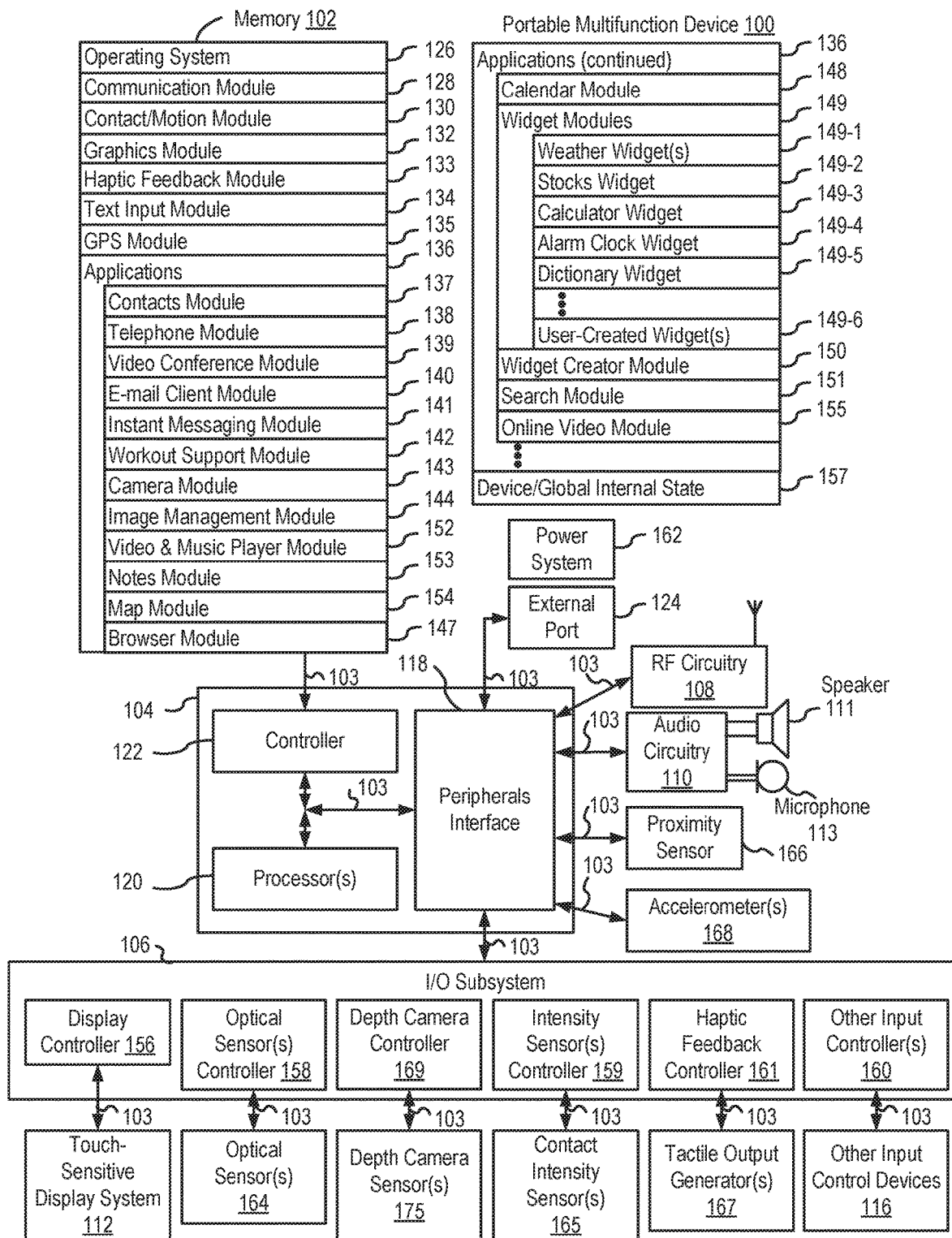
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
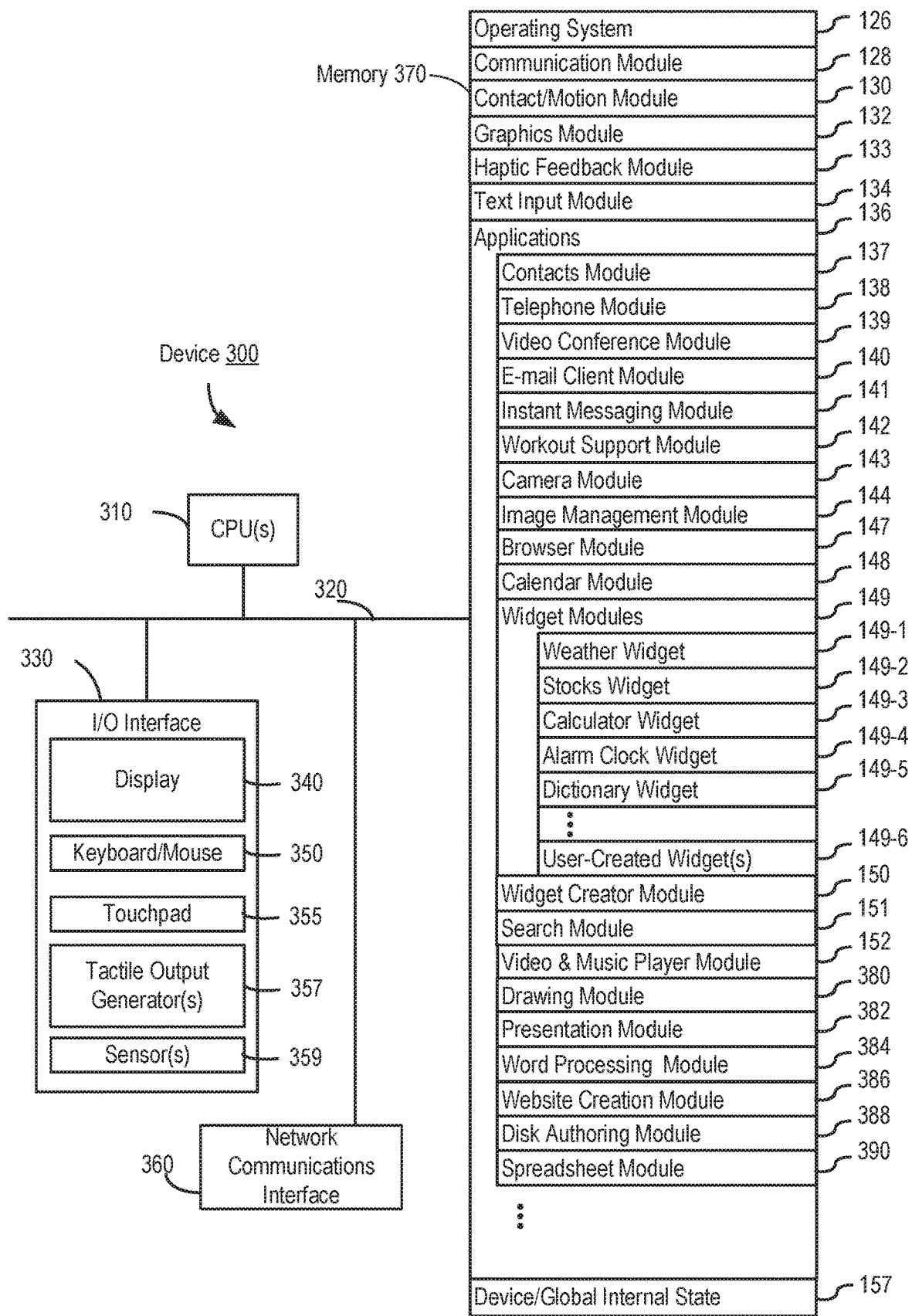
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116: and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo!Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
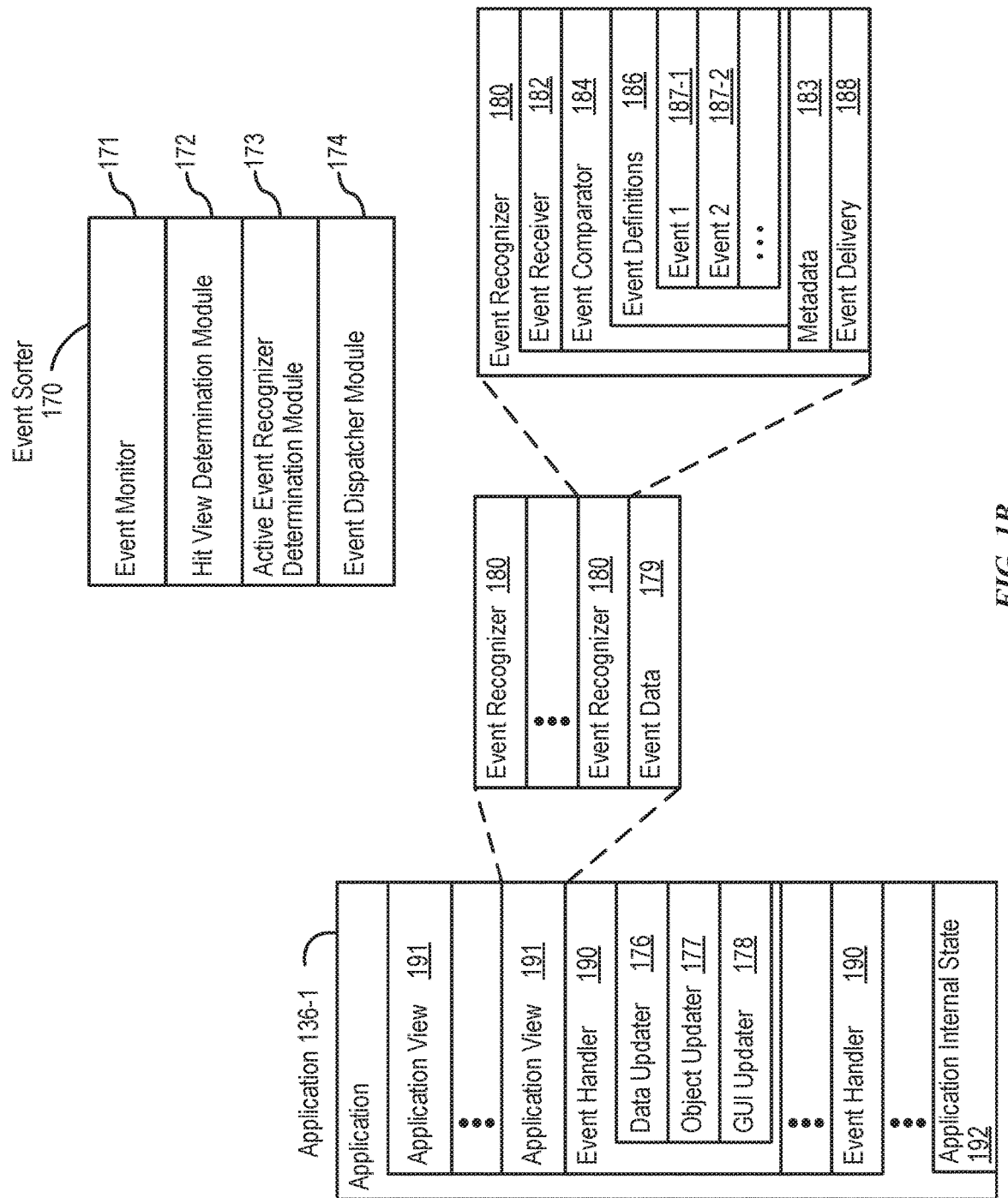
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
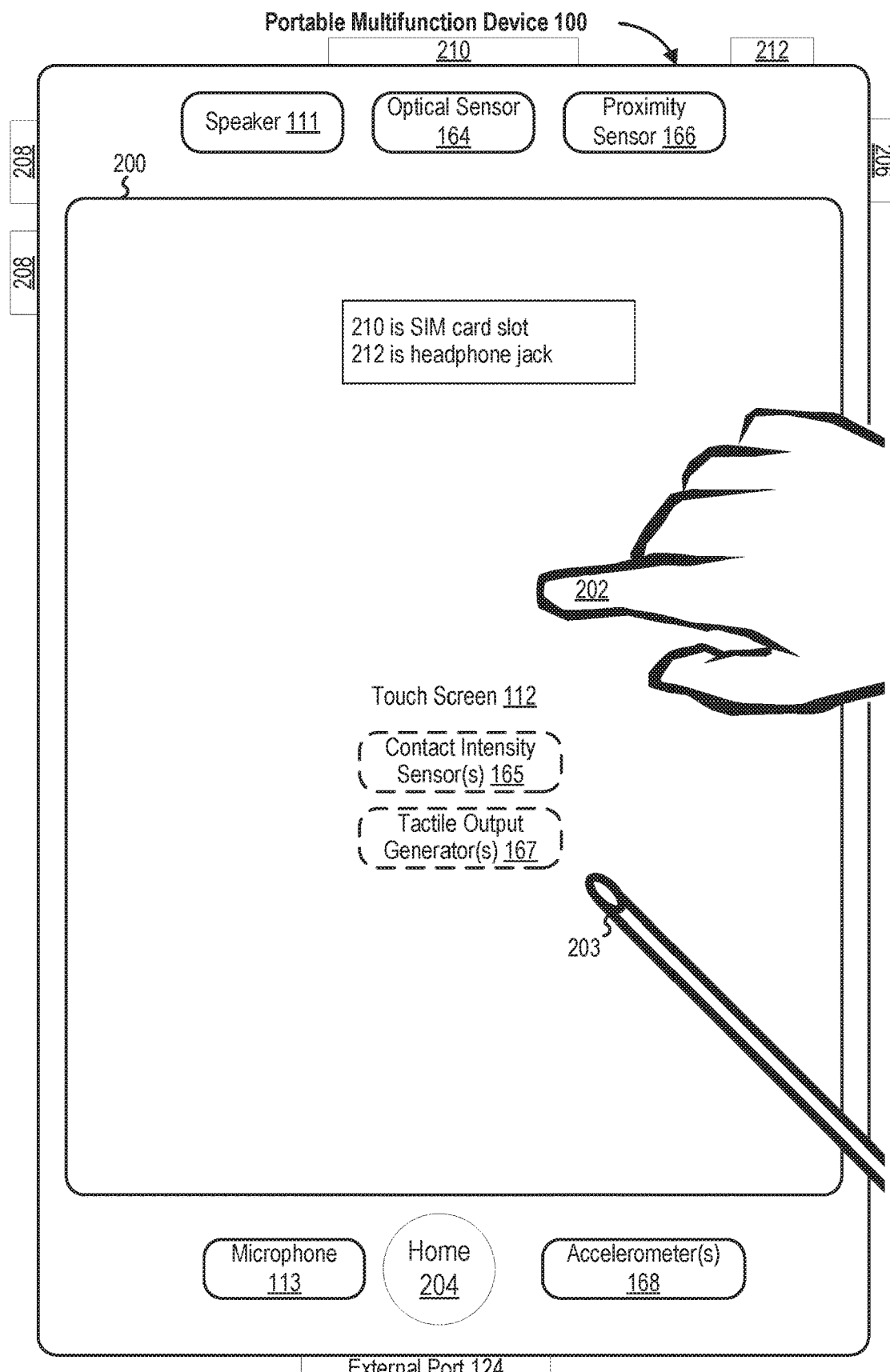
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
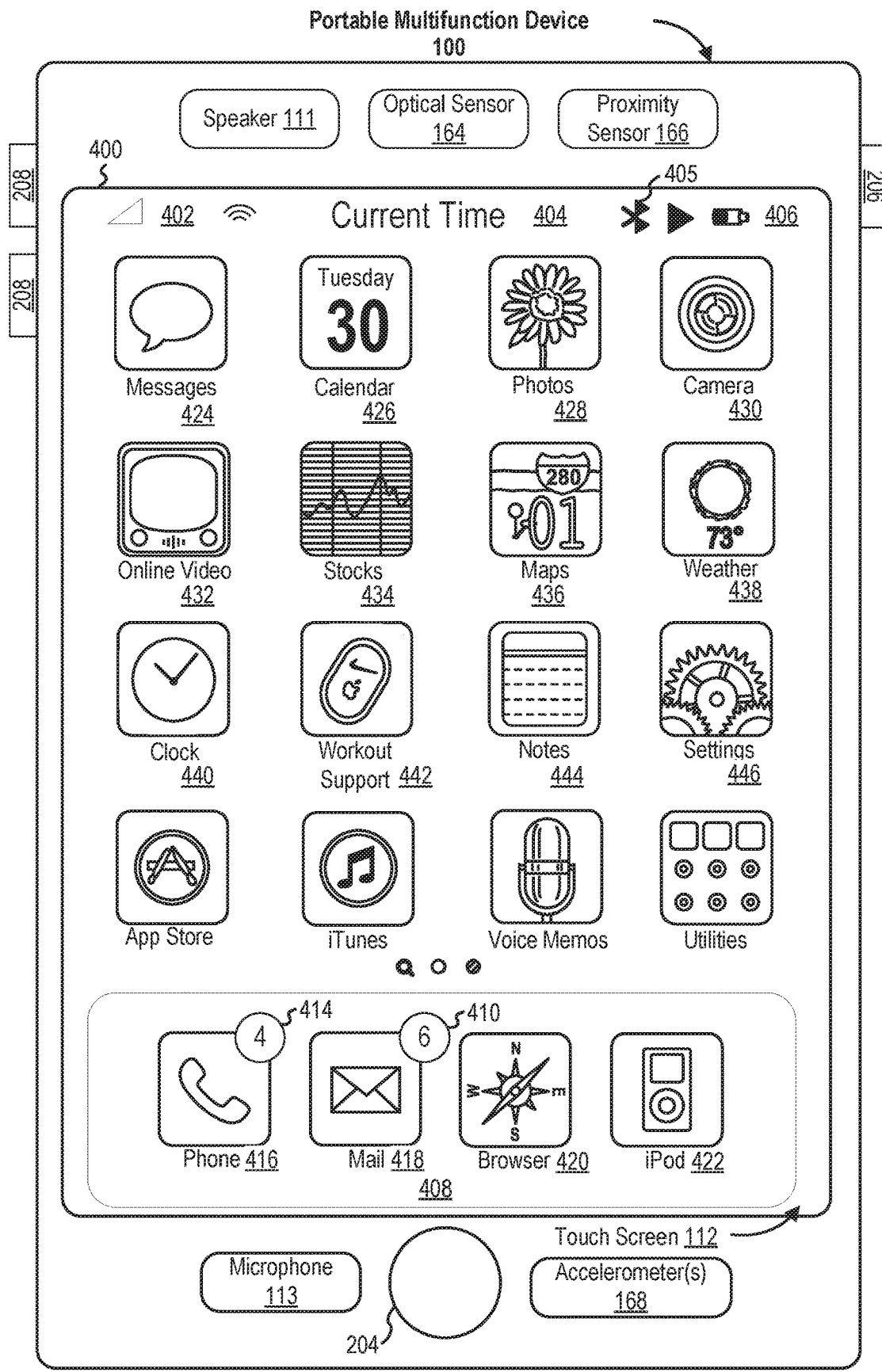
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
 Icon 416 for telephone module 138, labeled "Phone," which optionally includes an indicator 414 of the number of missed calls or voicemail messages;
 Icon 418 for e-mail client module 140, labeled "Mail," which optionally includes an indicator 410 of the number of unread e-mails;
 Icon 420 for browser module 147, labeled "Browser;" and
 Icon 422 for video and music player module 152, also referred to as iPod (trademark of Apple Inc.) module 152, labeled "iPod;" and
Icons for other applications, such as:
 Icon 424 for IM module 141, labeled "Messages;"
 Icon 426 for calendar module 148, labeled "Calendar;"
 Icon 428 for image management module 144, labeled "Photos;"
 Icon 430 for camera module 143, labeled "Camera;"
 Icon 432 for online video module 155, labeled "Online Video;"
 Icon 434 for stocks widget 149-2, labeled "Stocks;"
 Icon 436 for map module 154, labeled "Maps;"
 Icon 438 for weather widget 149-1, labeled "Weather;"
 Icon 440 for alarm clock widget 149-4, labeled "Clock;"
 Icon 442 for workout support module 142, labeled "Workout Support;"
 Icon 444 for notes module 153, labeled "Notes;" and
 Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
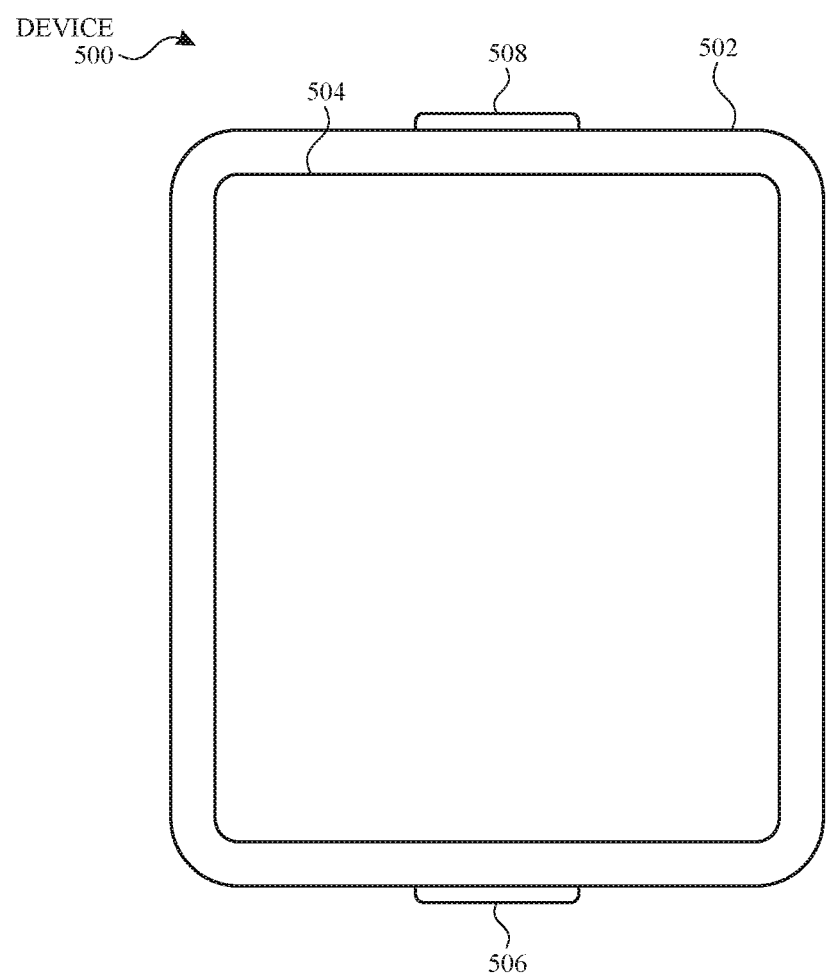
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications:

International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
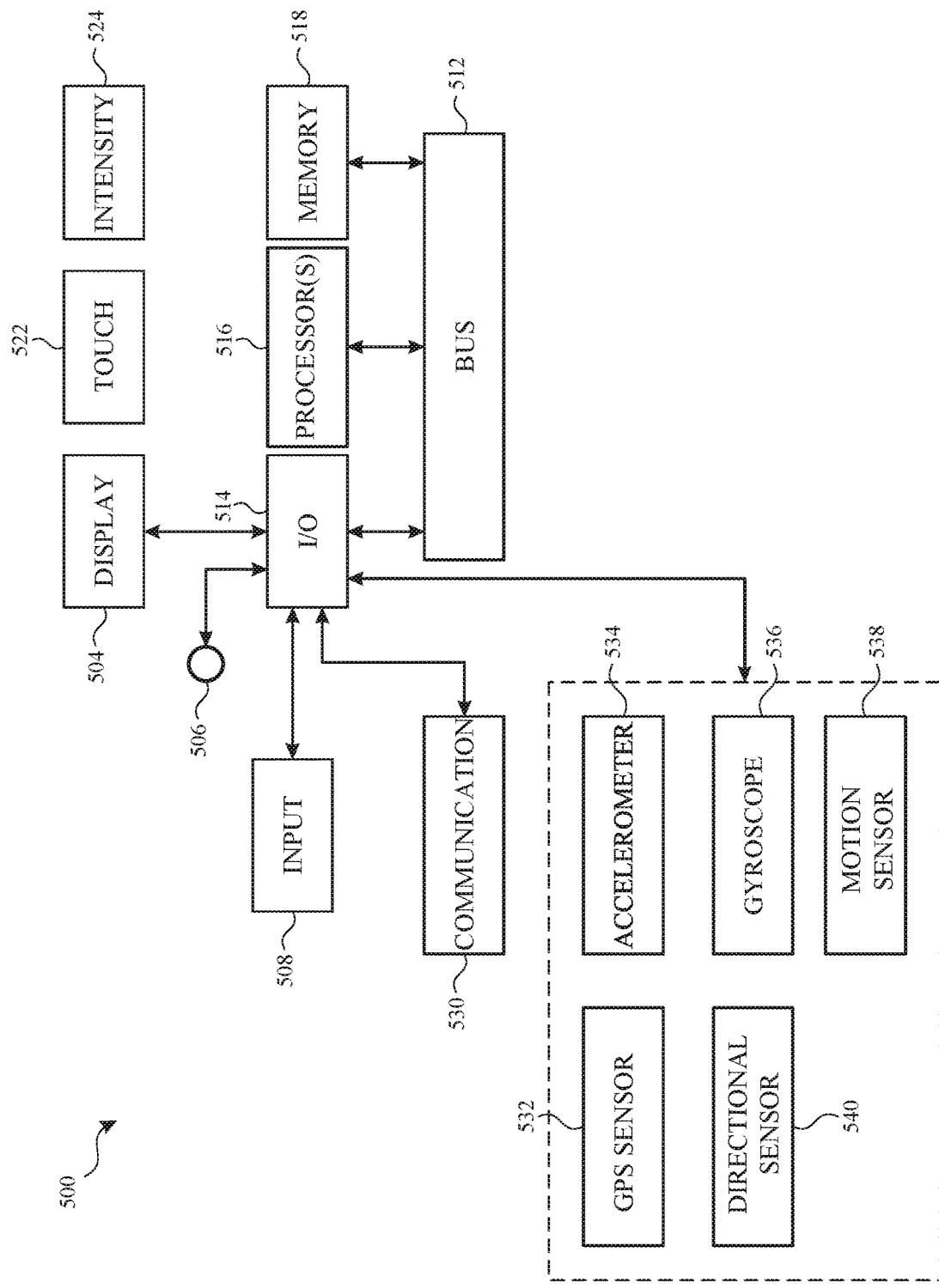
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 800, 900, and 1100 (FIGS. 7A, 7B, 8A, 8B, 9, 11A, and 11B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6I illustrate exemplary user interfaces for presenting activity trends, in accordance with some embodiments. The user interfaces in these figures are used to illustrate the processes described below, including the processes in FIGS. 7A, 7B, 8A, 8B, and 9.

Figure 6A:
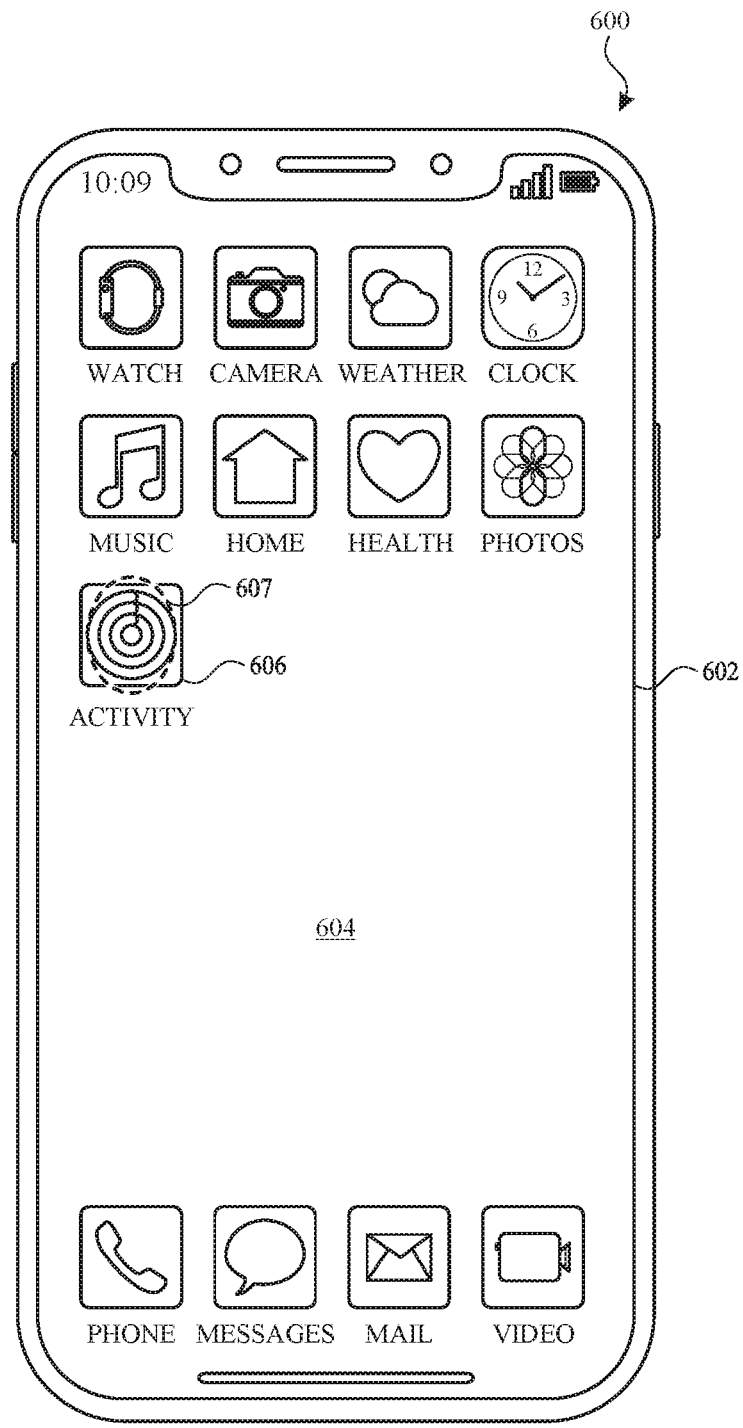
FIG. 6A depicts an electronic device displaying a home user interface via a display device.

FIG. 6A depicts electronic device 600 displaying home user interface 604 via display device 602. In some examples, electronic device 600 includes one or more features of devices 100, 300, or 500. Home user interface 604 includes multiple affordances, each affordance for initiating a different application. For example, the multiple affordances include activity affordance 606 for initiating an activity application (e.g., an application corresponding to physical activity performed by a user associated with electronic device 600).

As depicted in FIG. 6A, electronic device 600 receives user input 607 corresponding to selection of activity affordance 606. User input 607 can include a touch gesture, such as a tap gesture on activity affordance 606, causing the activity application to be initiated (e.g., display of a user interface of the activity application, such as information user interface 608 (depicted in FIG. 6B) or 90-day trends user interface 612 (depicted in FIGS. 6C-6F).

Figure 6B:
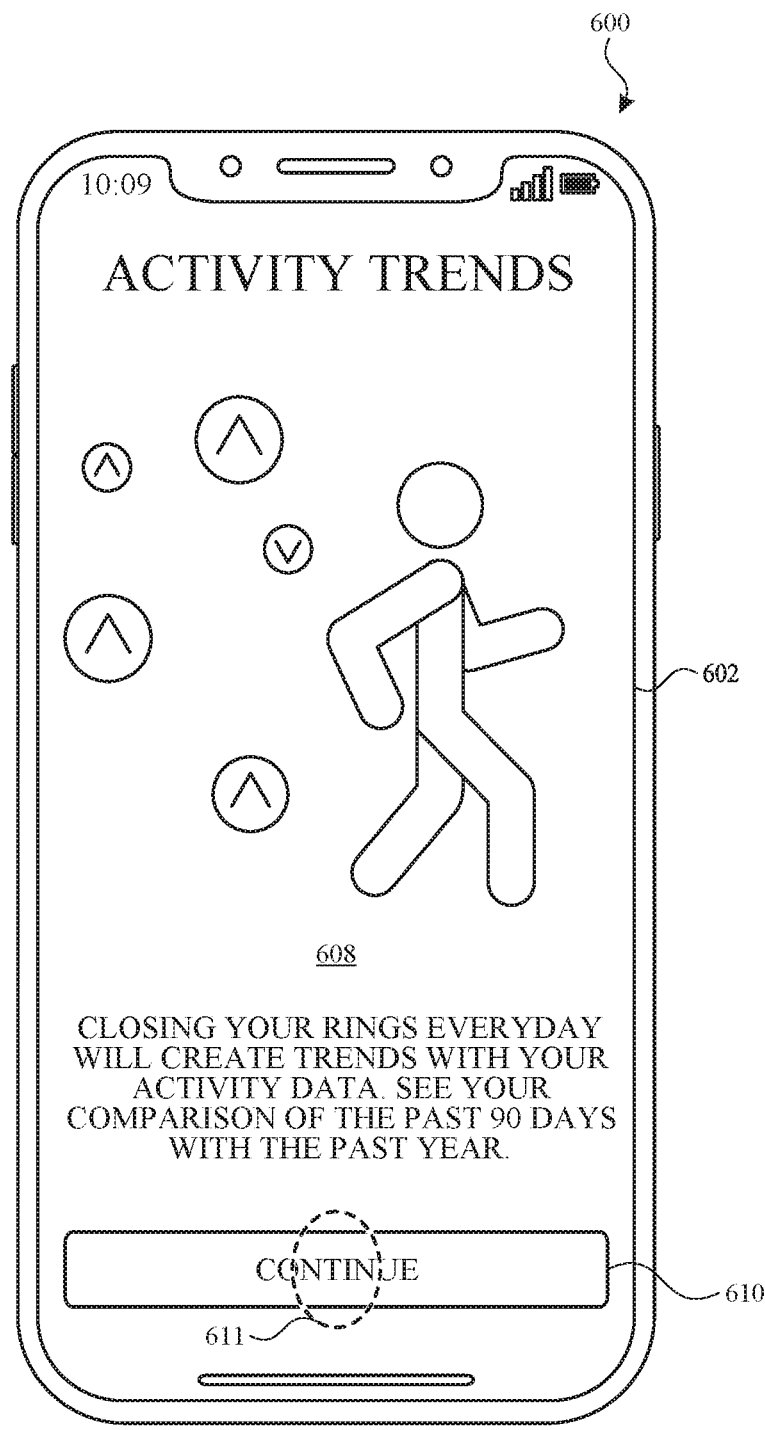
FIG. 6B depicts an electronic device displaying an information user interface for an activity application.

FIG. 6B depicts electronic device 600 displaying information user interface 608 for an activity application (e.g., the activity application discussed above for FIG. 6A). Information user interface 608 is an example of a first user interface displayed when initiating the activity application. In some examples, information user interface 608 is displayed at an initial time that a user navigates to the activity application after content to implement activity trends (e.g., techniques described in methods 700, 800, or 900) has been received by electronic device 600 (e.g., after an update or after an installation of the activity application at a time after the content has been added to the activity application).

Figure 6C:
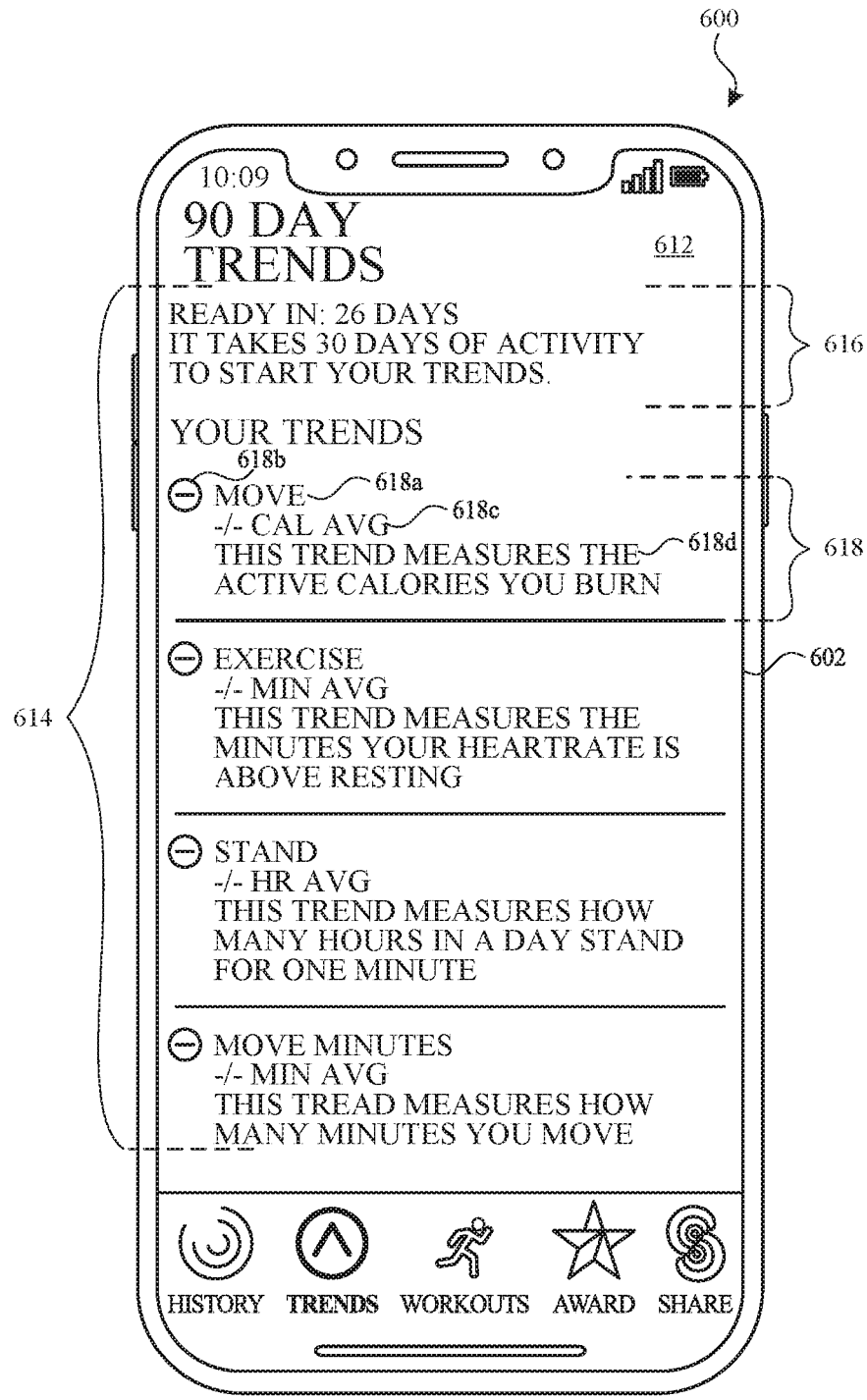
FIG. 6C depicts an electronic device displaying an instance of a 90-day trends user interface via a display device when an insufficient amount of data to identify a trend has been received for multiple activity metrics.

In some examples, information user interface 608 is displayed in response to receiving user input (e.g., user input 607) corresponding to selection of an activity affordance (e.g., activity affordance 606). It should be recognized that other user interfaces (e.g., 90-day trends user interface 612, as depicted in FIG. 6C) can be displayed when initiating the activity application, such as when information user interface 608 has been previously dismissed. In some examples, one or more user inputs must be received before displaying information user interface 608 and/or 90-day trends user interface 612.

Information user interface 608 provides information related to how activity trends in the activity application work. For example, FIG. 6B depicts information user interface 608 including text that states "Closing your rings everyday will create trends with your activity data. See your comparison of the past 90 days with the past year."

Information user interface 608 includes continue affordance 610. Selection of continue affordance 610 dismisses information user interface 608 and causes a different user interface to be displayed (e.g., 90-day trends user interface 612, as depicted in FIG. 6C). As depicted in FIG. 6B, electronic device 600 receives user input 611 corresponding to selection of continue affordance 610. User input 611 can include a touch gesture, such as a tap gesture on continue affordance 610.

FIG. 6C depicts electronic device 600 displaying an instance of 90-day trends user interface 612 via display device 602 when an insufficient amount of data to identify a trend has been received for multiple activity metrics. As used herein, a trend corresponds to a comparison of data within a first time period (e.g., 90 days) and data within a second time period (e.g., 365 days), where the first time period is included within the second time period. In some examples, a trend can be identified with less than a full time period. For example, instead of requiring 365 days of activity data for an activity metric, a trend for the activity metric can be identified when there is at least 180 days of activity data for the activity data, where (1) the remaining days without activity data are ignored when identifying the trend and (2) the shorter of the two time periods is potentially shortened to maintain a similar percentage between the two percentages (e.g., when 180 days is received, the shorter of the two time periods can be 45). As shown, FIG. 6C is a user interface shown after four days of activity is received for a user associated with electronic device 600. For clarity of the examples discussed herein, a table is provided below to provide examples of different trend classifications for different scenarios.

| 90 day average | 365 day average | Difference between 90 day average and 365 average | Trend Assessment |
|---|---|---|---|
| 90 | 100 | −10 | Negative |
| 100 | 100 | 0 | Neutral (in some examples herein, classified as positive) |
| 110 | 100 | 10 | Positive |

The instance of 90-day trends user interface 612 as depicted in FIG. 6C includes insufficient data portion 614 with header portion 616 and representations for multiple activity metrics, such as move representation 618. Header portion 616 includes a predicted amount of time before a sufficient amount of data will have been received. For example, header portion 616 includes text stating: "Ready in: 26 days." Such text indicates that it is estimated that the activity application will have enough data to present activity trends via 90-day trends user interface 612 in 26 days. The estimate can be calculated based on forecasting that sufficient information will be received each day for the next 26 days, satisfying an amount of activity data to provide activity trends after the 26 days. Header portion 616 includes information regarding why it will take 26 days to be ready (e.g., "It takes 30 days of activity to start your trends.").

As indicated above, insufficient data portion 614 includes move representation 618. Move representation 618 corresponds to activity data related to a move activity metric (e.g., an amount of movement that is determined for a user). Move representation 618 includes identification information 618a indicating that move representation 618 relates to the move activity metric (the "move" text), icon 618b indicating that there is insufficient activity data received for the move activity metric to determine an activity trend for the move activity metric (the "−" with a circle around it), placeholder information 618c indicating an average value for move representation 618 is unavailable (the "−/−cal avg" text), and description 618d (the "this trend measures the active calories you burn" text). Other examples of representations for activity metrics depicted in FIG. 6C include exercise, stand, and move minutes. Each of the other examples of representations include similar content as move representation 618.

Figure 6D:
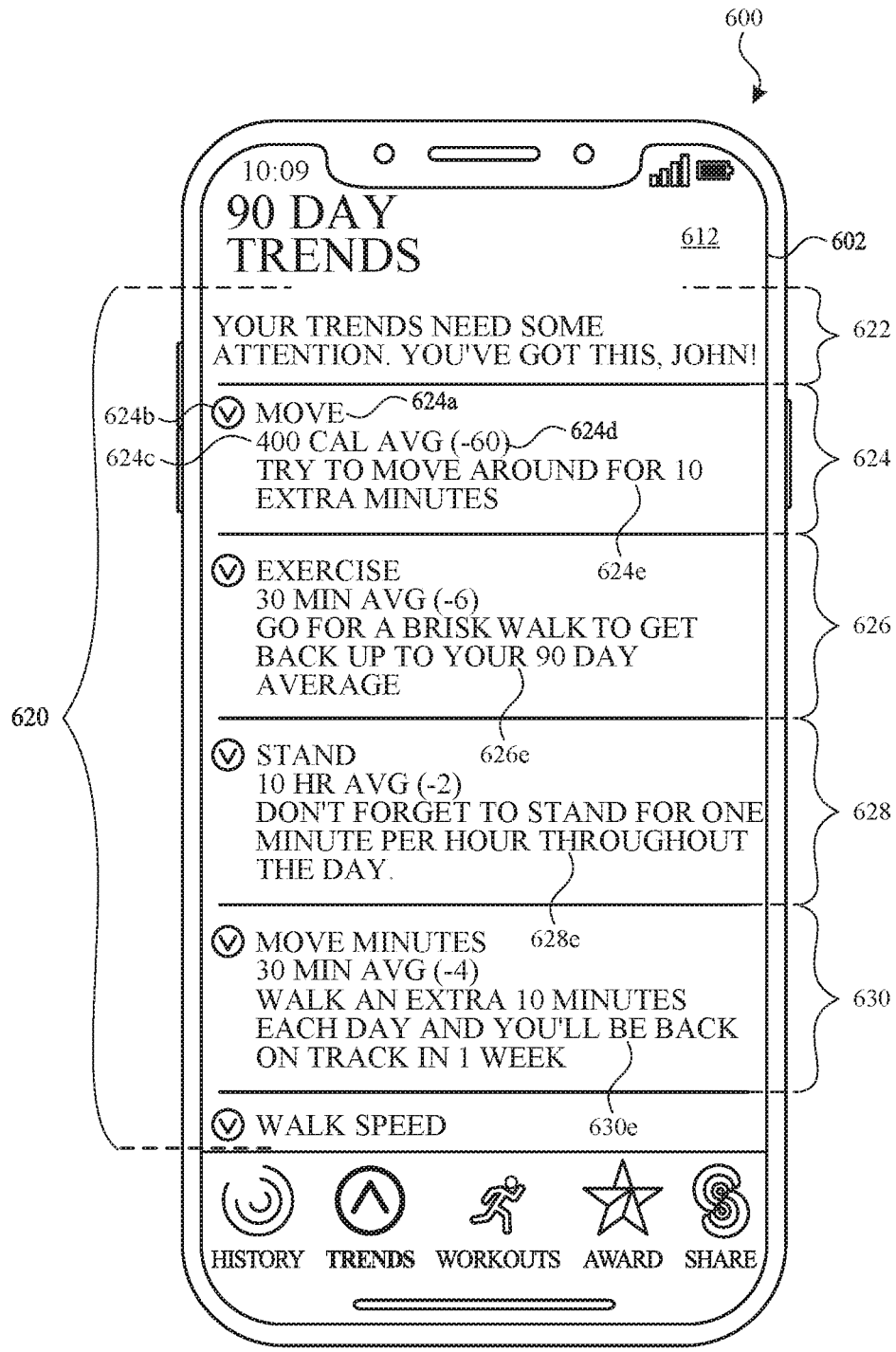
FIG. 6D depicts an electronic device displaying an instance of a 90-day trends user interface via a display device when all activity metrics have a negative trend within the last 90 days as compared to the last 365 days.

FIG. 6D depicts electronic device 600 displaying an instance of 90-day trends user interface 612 via display device 602 when all activity metrics have a negative trend within the last 90 days as compared to the last 365 days. It should be recognized that trends might be over different times from 90 days and 365 days (such as more or less than 90 days and/or more or less than 365 days). In some examples, the trends are based on rolling time periods. In some examples, a rolling time period means that, as a new day is added to a time period, an oldest day in the time period is removed. For example, a rolling time period of 90 days means that at day 90 the rolling time period equals day 1 to day 90 and at day 91 the rolling time period equals day 2 to day 91.

FIG. 6D depicts 90-day trends user interface 612 at least 30 days after at least 30 days of activity data is received. For example, the instance of 90-day trends user interface 612 depicted in FIG. 6D can be displayed 26 days after the instance of 90-day trends user interface 612 depicted in FIG. 6C is displayed. In some examples, activity trends (e.g., move representation 624) in 90-day trends user interface 612 are refreshed daily such that activity trends are updated each day. The instance of 90-day trends user interface 612 depicted in FIG. 6D includes negative trend portion 620 with overall coaching portion 622 and representations for multiple activity metrics, including move representation 624.

Overall coaching portion 622 includes text providing a summary of the included activity metrics. For example, overall coaching portion 622 includes text stating: "Your trends need some attention. You've got this, John!"

The representations for multiple activity metrics included in negative trend portion 620 each are associated with a different activity metric that has been determined to have a negative trend (e.g., an average of an activity metric for the past 90 days is less than an average of the activity metric for the past 365 days). For example, negative trend portion 620 includes move representation 624. Move representation 624 corresponds to activity data related to a move activity metric (e.g., an amount of movement that is determined for a user). Move representation 624 includes identification information 624a indicating that it relates to the move activity metric (the "move" text), icon 624b indicating that the move activity metric is trending down (the "V" with a circle around it), average value 624c indicating an average value for the move activity metric over the last 90 days (the "400 cal avg" text), comparison value 624d indicating the difference between the average value for the move activity metric over the last 90 days and an average value for the move activity metric over the last 365 days ("−60"), and coaching indication 624e (the "Try to move around for 10 extra minutes" text). Other examples of representations depicted in FIG. 6D include exercise, stand, and move minutes. Each of the other examples of presentations include similar content as move representation 618, including their own coaching indication (e.g., 626e, 628e, and 630e).

In some examples, coaching indications are only provided to representations corresponding to activity metrics with a negative trend over the last 90 days as compared to the last 365 days. In such examples, coaching indications include a prediction for when a negative trend will transition to a neutral or positive trend.

In some examples, coaching indications are modified based on an amount of time it would take for an average of the corresponding activity metric to transition to a neutral or positive trend when forecasting an estimated increase (e.g., 10% per day). In some examples, the estimated increase can be capped based on a threshold for the corresponding activity metric (e.g., an estimated increase for standing cannot cause a stand goal of greater than 14 hours). In some examples, the amount of time affects how the coaching indications are modified. For example: when the amount of time is less than a week, a coaching indication includes a prediction with the amount of time; when the amount of time is more than a week and less than two weeks, a coaching indication includes a prediction with the amount of time rounded to a single week; when the amount of time is more than two weeks, a coaching indication does not include a prediction of time. In some examples, different activity metrics use a different estimated increase.

In some examples, forecasting includes simulating the estimated increase by: (1) forming a histogram associated with activity data for each of a shorter time period (e.g., the last 90 days) and a longer time period (e.g., the last 365 days) (e.g., each bin in the histogram corresponding to an average of activity data for a particular activity metric for a different day); (2) removing an oldest bin from the histogram; (3) adding a new bin to the histogram for the next day with a value corresponding to a value of activity data for a particular activity metric for a current day and the estimated increase (e.g., if the value for the current day is 10 and the estimated increase is 1 (e.g., 10% of the value for the current day), the value for the new bin would be 11 instead of 10); and (4) repeating 2 and 3 until the corresponding activity metric transitions to a neutral or positive trend. In some examples, when repeating 3, the estimated increase can be the same for each additional day (e.g., based on example above, if the estimated increase is 1 and a value for a previous day is 11, the value for a current day would be 12), become zero after the first day (e.g., based on example above, if the estimated increase becomes 9 after the first day and a value for a previous day is 11, the value for a current day would be 11 instead of continuing to increase to 12), or change each day based on some function (e.g., f(x)=1/x).

In some examples, coaching indications are modified based on a recent trend within the last 90 days, such as the last 15 days. In one example, the recent trend is determined using the Mann-Kendall (MK) test to look at pairs of data in a given data set to identify whether a monotonic trend is present.

For clarity of the examples discussed above, a table is provided below to provide examples of different coaching indications for different scenarios with a description of why the coaching indication is what it is.

| Trend classification | Example coaching indication | Explanation of coaching indication |
|---|---|---|
| Positive trend for 90/365 and recently positive within 90 | "Getting better every day, keep it up!" | Based on having a positive trend and recently positive, a coaching indication should encourage similar behavior in the future. |
| Positive trend for 90/365 and recently negative within 90 | "While you are above average for the last 90 days, you are starting to lose some ground." | Based on having a positive trend but recently negative, a coaching indication should recognize the positive trend but be more cautionary due to the recent negative trend. |
| Negative trend for 90/365 but recently positive within 90 | "Keep doing what you are doing and you will be back to your yearly average in no time." | Based on having a negative trend but recently positive, a coaching indication should recognize that the user is improving. |
| Negative trend for 90/365 and recently negative within 90 | "Don't forget to stand for one minute per hour throughout the day, you are getting farther from your average lately." | Based on having a negative trend and recently negative, a coaching indication should identify that a user is falling farther behind. |
| Negative trend for 90/365 that can transition to a positive trend within a week if to maintain a 10% increase in average value as compared to the last 90 days | "Try to move around for 10 extra minutes for the next 3 days and you will be right back to your yearly average." | Based on being able to transition within a week, a coaching indication should identify a number of days it takes to transition to a positive trend with an estimated increase. |
| Negative trend for 90/365 that can transition to a positive trend longer than a week but within a few weeks if maintain a 10% increase in average value as compared to the last 90 days | "Walk an extra 10 minutes each day and you'll be back on track in 1 week." | Based on being able to transition longer than a week but within a few weeks, a coaching indication should identify a way for a user to reach the yearly average but round to the nearest week. |
| Negative trend for 90/365 that can transition to a positive trend over a few weeks if maintain a 10% increase in average value as compared to the last 90 days | "Let's get back to the swing of things and walk a couple of minutes each day," | Based on being able to transition longer than a few weeks, a coaching indication should not include any particular way to improve, such as a number of days or even an amount of activity per day. |

Figure 6E:
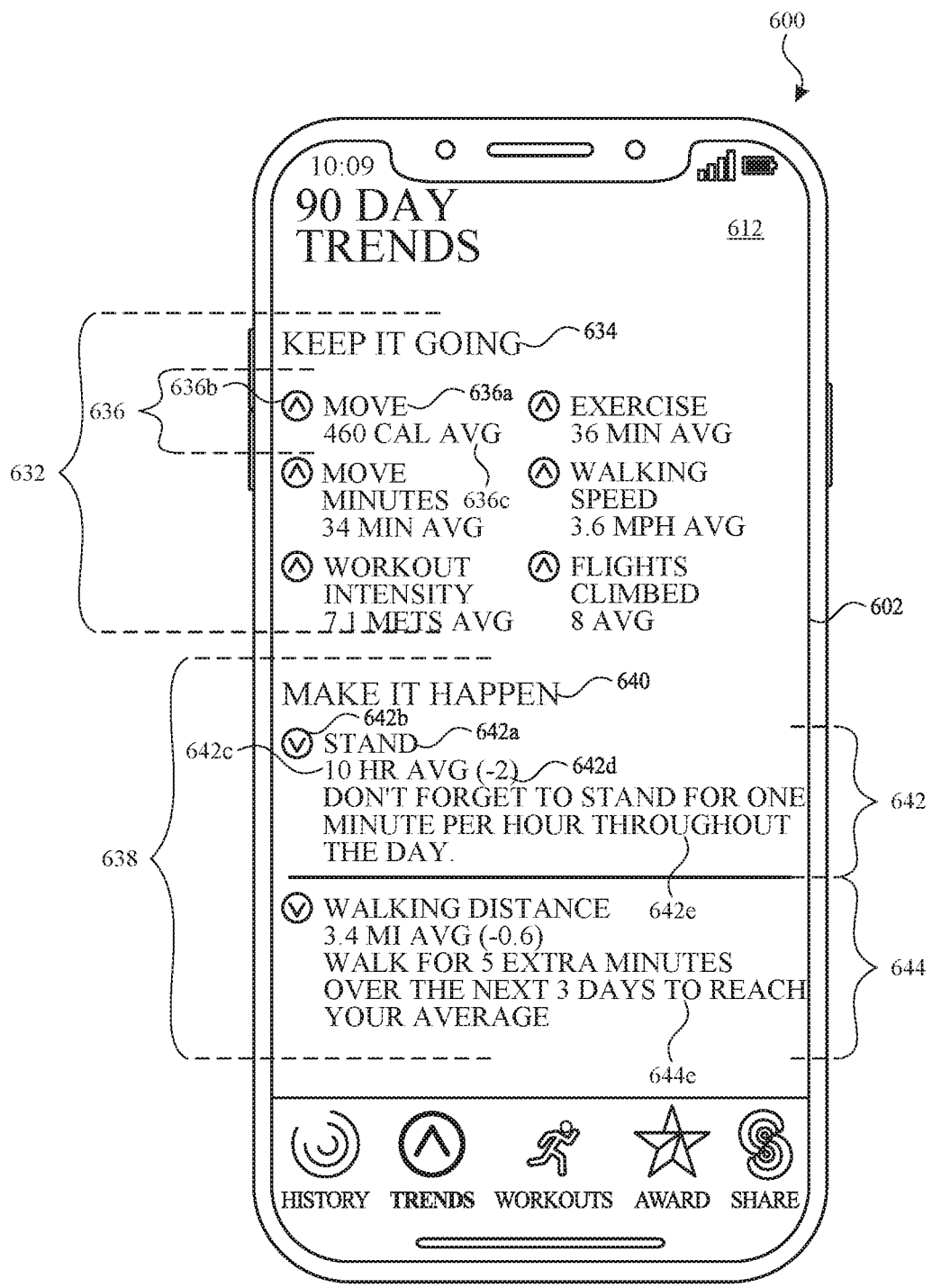
FIG. 6E depicts an electronic device displaying an instance of a 90-day trends user interface via a display device when some activity metrics have a positive trend and other activity metrics have a negative trend within the last 90 days as compared to the last 365 days.

FIG. 6E depicts electronic device 600 displaying an instance of 90-day trends user interface 612 via display device 602 when some activity metrics have a positive trend and other activity metrics have a negative trend within the last 90 days as compared to the last 365 days. FIG. 6E depicts 90-day trends user interface 612 at least 30 days after at least 30 days of activity data is received. The instance of 90-day trends user interface 612 depicted in FIG. 6E includes positive trend portion 632 and negative trend portion 638, each with an overall coaching indication for the respective portion (e.g., overall coaching indication 634 and overall coaching indication 640). In one example, overall coaching indication 634 for positive trend portion 632 includes the text "Keep it going" and overall coaching indication 640 for negative trend portion 638 includes the text "Make it happen"). In some examples, the instance of 90-day trends user interface 612 depicted in FIG. 6E (or any instances of 90-day trends user interface 612) includes an insufficient data portion (not illustrated, but similar to insufficient data portion 614 in the instance of 90-day trends user interface 612 depicted in FIG. 6C) for one or more activity metrics with an insufficient amount of corresponding data. In one example, the insufficient data portion is below negative trend portion 638.

As mentioned above, the instance of 90-day trends user interface 612 as depicted in FIG. 6E includes positive trend portion 632 with representations for multiple activity metrics that have each been determined to be trending up or neutral (e.g., an average of an activity metric for the past 90 days is equal to or greater than an average of the activity metric for the past 365 days). For example, positive trend portion 632 includes move representation 636. Move representation 636 corresponds to activity data related to a move activity metric (e.g., an amount of movement that is determined for a user). Move representation 636 includes identification information 636a indicating that it relates to the move activity metric (the "move" text), icon 636b indicating that the move activity metric has a positive trend over the last 90 days as compared to the last 365 days (the "^" with a circle around it), and average value 636c indicating that the move activity metric has averaged 460 calories over the last 90 days (the "460 cal avg" text).

It should be recognized that the move representation, when in positive trend portion 632, does not include a comparison value indicating the difference between the average value for the move activity metric over the last 90 days and an average value for the move activity metric over the last 365 days and/or a coaching indication while both such content is provided for activity metrics in negative trend portion 638. In some examples, only providing the difference and/or the coaching indication in negative trend portion 638 allows a system to not push users into thinking they need to keep increasing their trend. Similarly, classifying equal as positive, allows a system to not push users into thinking they need to keep increasing their trend.

Other examples of representations of activity metrics in positive trend portion 632 depicted in FIG. 6E include exercise, move minutes, walking speed, workout intensity, and flights climbed. While each of the other examples of representations of activity metrics in positive trend portion 632 include similar content as move representation 636, it should be recognized that different representations sometimes have different units of measure. For example, an exercise activity representation, as depicted in FIG. 6E, includes text indicating that exercise activity metric averaged 36 minutes per day for the last 90 days.

As mentioned above, the instance of 90-day trends user interface 612 as depicted in FIG. 6E includes negative trend portion 638 with representations for multiple activity metrics that are each associated with a different activity metric that has been determined to have a negative trend (e.g., an average of an activity metric for the past 90 days is less than an average of the activity metric for the past 365 days). For example, negative trend portion 638 includes stand representation 642. Stand representation 642 corresponds to activity data related to a stand activity metric (e.g., a number of hours per day where a user has determined to have stood for at least one hour). Stand representation 642 includes identification information 642a indicating that it relates to the stand activity metric (the "stand" text), icon 642b indicating that the stand activity metric has a negative trend over the last 90 days as compared to the last 365 days (the "V" with a circle around it), average value 642c indicating that the stand activity metric has averaged 10 hours per day over the last 90 days (the "10 hr avg" text), comparison value 642d indicating the difference between the average value for the stand activity metric over the last 90 days and an average value for the stand activity metric over the last 365 days ("−2"), and coaching indication 642e (the "Don't forget to stand for one minute per hour throughout the day" text). The other example of a representation in negative trend portion 638 depicted in FIG. 6E is walking distance representation 644. Walking distance representation 644 includes similar content as stand representation 642, including its own coaching indication (644e).

It should be recognized that the order within each portion (e.g., positive trend portion 632 and negative trend portion 638) maintains the order of representations as provided in instances discussed above. A representation not included in one of the portions continues the order in another portion. For example, the order in FIG. 6D is move, exercise, stand, and move minutes and the order in positive trend portion 632 is move, exercise, and move minutes, with stand missing from positive trend portion 632 because move minutes did not have a positive trend. In FIG. 6D, it can be seen that stand is the first representation in negative trend portion 638.

In some examples, one or more icons in positive trend portion 632 (e.g., 636b) (e.g., in some examples, all of the icons in positive trend portion 632, either sequentially or at the same time) are animated (e.g., bounce in an upward direction) in response to displaying the instance of 90-day trends user interface 612 depicted in FIG. 6E. After a time threshold (e.g., zero or more; in some examples, non-zero) after animating the one or more icons in positive trend portion 632 has passed, one or more icons in negative trend portion 638 (e.g., 642b) (e.g., in some examples, all of the icons in negative trend portion 638, either sequentially or at the same time) are animated (e.g., bounce in a downward direction). By animating icons associated with negative trend portion 638 after animating icons associated with positive trend portion 632, the instance of 90-day trends user interface 612 as depicted in FIG. 6E can draw emphasis to representations in negative trend portion 638.

Figure 6F:
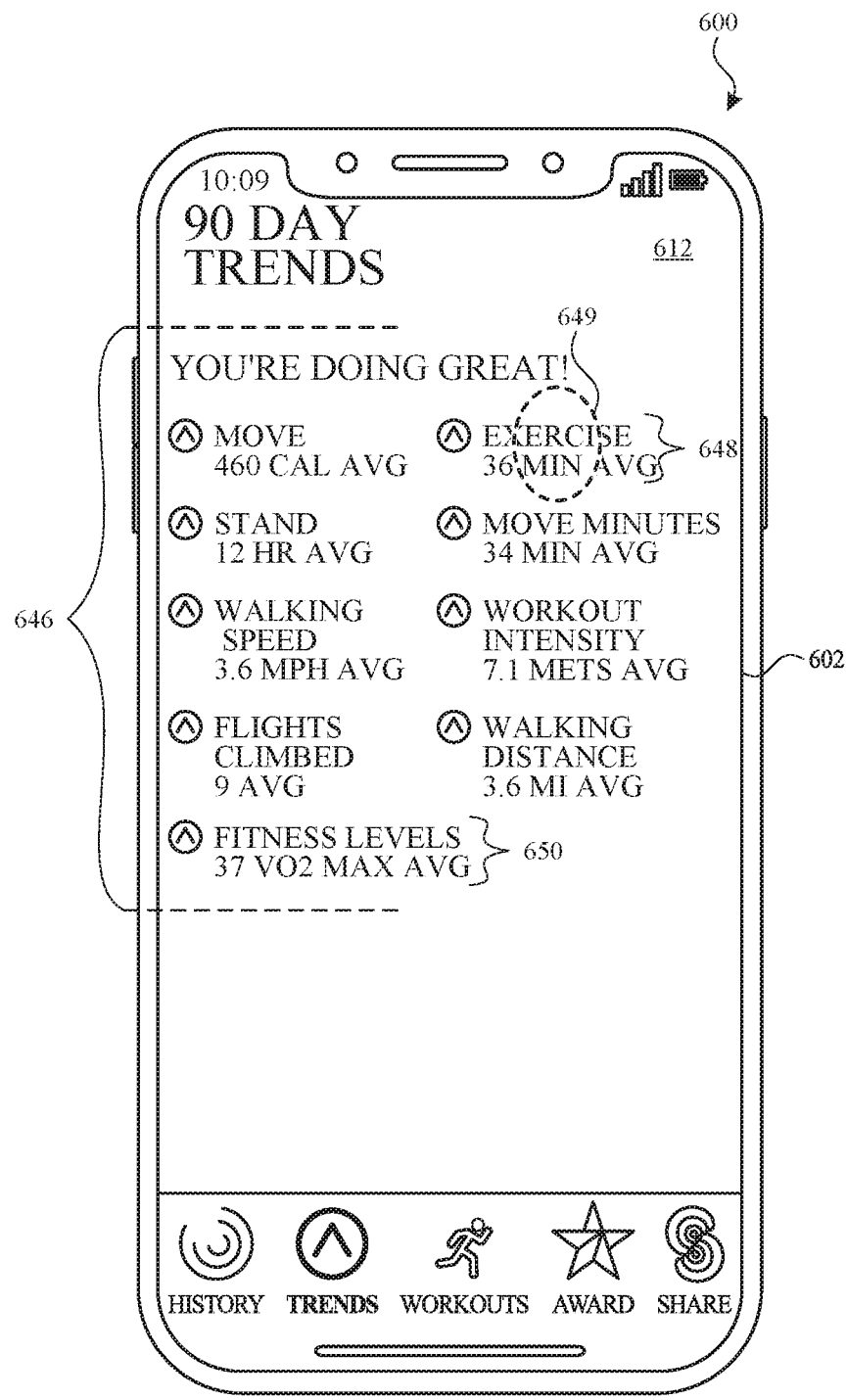
FIG. 6F depicts an electronic device displaying an instance of a 90-day trends user interface via a display device when all activity metrics have a positive trend within the last 90 days as compared to the last 365 days.

FIG. 6F depicts electronic device 600 displaying an instance of 90-day trends user interface 612 via display device 602 when all activity metrics have a positive trend within the last 90 days as compared to the last 365 days. FIG. 6F depicts 90-day trends user interface 612 at least 30 days after at least 30 days of activity data is received. The instance of 90-day trends user interface 612 depicted in FIG. 6F includes positive trend portion 646 and an overall coaching indication stating "You're doing great!"

Positive trend portion 646 includes representations for multiple activity metrics that have each been determined to be neutral or positive (e.g., an average of an activity metric for the past 90 days is equal to or greater than an average of the activity metric for the past 365 days). For example, positive trend portion 646 includes exercise representation 648 and fitness levels representation 650. Exercise representation 648 corresponds to activity data related to an exercise activity metric (e.g., an amount of time for which a user has been detected exercising). Fitness levels representation 650 corresponds to activity data related to a different exercise metric (e.g., a determined workout intensity for a user). It should be recognized that fitness levels representation 650 has not been displayed in other instances of 90-day trends user interface 612 described above. This is illustrating that some representations might only be displayed when there is at least some activity data received for a respective activity metric or there is enough activity data received for the respective activity metric to identify a trend (e.g., 37 $VO_2$ max avg). This allows for metrics that are often used to always show some representation (e.g., sometimes a null value) and other metrics that are not often used (or that require special equipment) to only show when either some activity data has been received or enough activity data has been received to provide a trend.

As depicted in FIG. 6F, electronic device 600 receives user input 649 corresponding to selection of exercise representation 648. User input 649 can include a touch gesture, such as a tap gesture on exercise representation 648, causing a detailed activity metric user interface corresponding to exercise representation 648 to be displayed (e.g., detailed exercise user interface 652, as depicted in FIG. 6G).

Figure 6G:
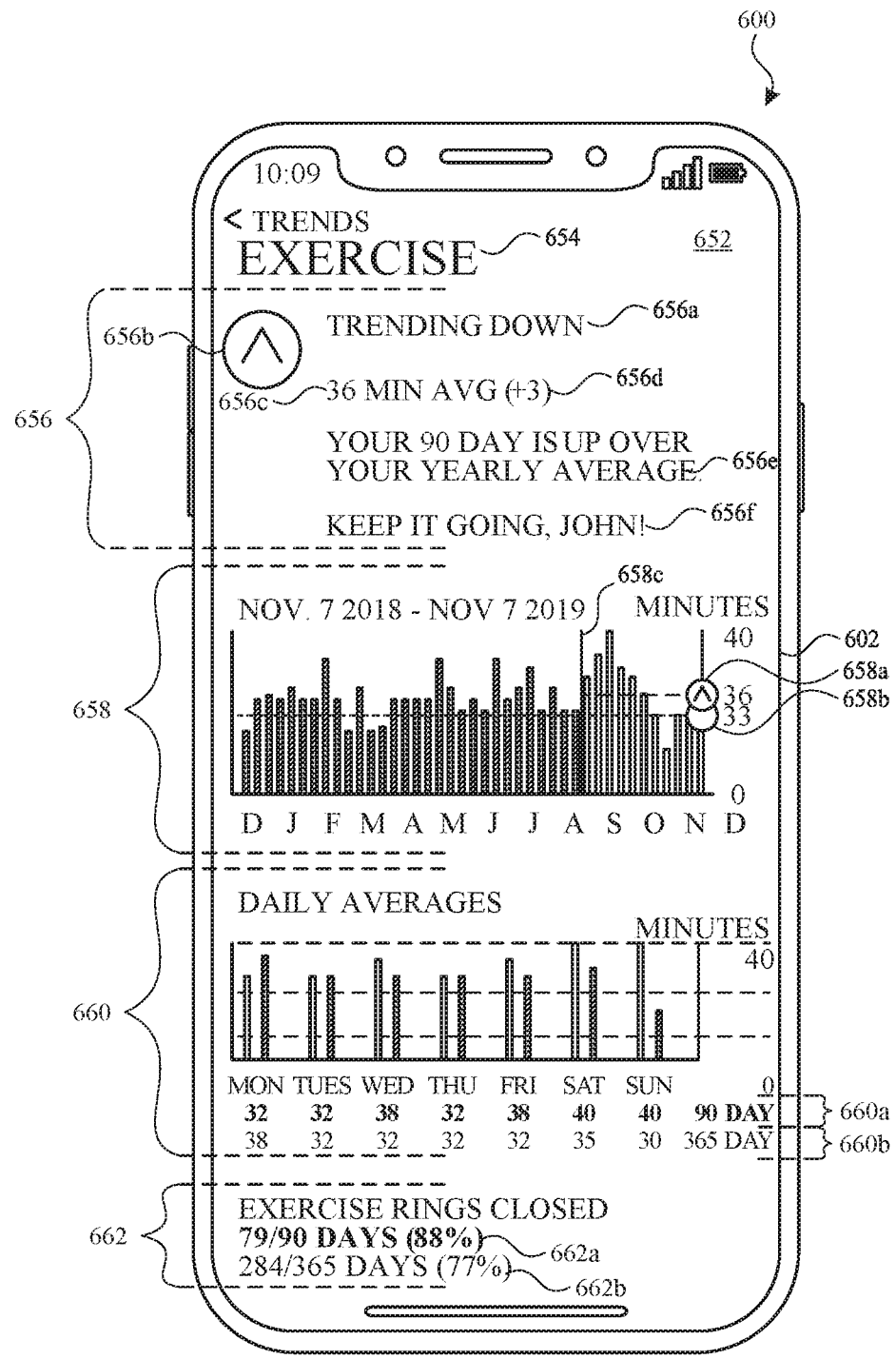
FIG. 6G depicts an electronic device displaying a detailed exercise user interface.

FIG. 6G depicts electronic device 600 displaying detailed exercise user interface 652. In some examples, detailed exercise user interface 652 is displayed in response to receiving user input (e.g., user input 649) corresponding to selection of exercise representation 648. In some examples, one or more user inputs must be received before displaying detailed exercise user interface 652. It should be recognized that other detailed activity metric user interfaces can be displayed when other activity metric representations are selected, the other detailed activity metric user interfaces corresponding to whichever activity metric representation is selected.

Detailed exercise user interface 652 includes identification information 654, indicating the activity metric that detailed exercise user interface 652 corresponds. For example, identification information 654 states that detailed exercise user interface 652 corresponds to an exercise activity metric.

Detailed exercise user interface 652 includes summary portion 656. Summary portion 656 includes textual representation 656a indicating whether the exercise activity metric is trending down (e.g., an average of the last 90 days is less than an average of the last 365 days) (where textual representation would be "trending down," as illustrated), trending up (e.g., an average of the last 90 days is more than an average of the last 365 days) (where textual representation would be "trending up"), or trending neutral (e.g., an average of the last 90 days is equal to an average of the last 365 days) (where textual representation would be "staying consistent"). It should be recognized that trending neutral and trending up can be grouped together such that a system does not distinguish between the two, and instead uses the trending up for when the trend is up or neutral. Summary portion 656 includes icon 656b indicating that the exercise activity metric has a positive trend over the last 90 days as compared to the last 365 days (the "^" with a circle around it). Summary portion 656 includes average value 656c indicating that the exercise activity metric has averaged 36 minutes per day over the last 90 days (the "36 min avg" text). Summary portion 656 includes difference indicator 656d indicating a difference between an average of the last 90 days and an average of the last 365 days ("+3"). Summary portion 656 includes summary information 656e with a textual equivalent of icon 656b. Summary portion 656 includes coaching indication 656f indicating a suggestion for the exercise activity metric going forward. As depicted in FIG. 6G, coaching indication 656f states "Keep it going, John!," reflecting that the exercise activity metric is trending upward. It should be recognized that summary portion 656 can include a subset of what was described above (e.g., summary portion 656 might not include textual representation 656a).

Detailed exercise user interface 652 includes weekly representation 658 to visually represent activity data for the exercise activity metric over the last 365 days. In some examples, such as depicted in FIG. 6G, weekly representation 658 is a bar graph with x-axis corresponding to time (e.g., weeks over the last 365 days) and y-axis corresponding to an average value for the exercise activity metric over either the last 90 days or the last 365 days. In such examples, weekly representation 658 is divided into weeks using a bar for each week (e.g., 52 bars). In some examples, the x-axis of weekly representation 658 is labeled by month and the range of the y-axis is from 0 to a maximum average value over the last 365 days (e.g., 40, as depicted in FIG. 6G).

As depicted in FIG. 6G in weekly representation 658, bars associated with time periods within the last 90 days are visually distinguished (e.g., different patterns or different colors) from bars associated with time periods within the last 365 days. In one example, the bars associated with the last 90 days are green while the bars associated with the last 365 days are gray. When a week does not have any corresponding activity data, a bar is not displayed for the week (e.g., 51 bars will be displayed instead of 52). In some examples, weekly representation 658 includes an additional indication to separate representations corresponding to the last 90 days and representations corresponding to the last 365 days but not the last 90 days. For example, in FIG. 6G, vertical line 658c is inserted separating the two groups of bars.

Weekly representation 658 includes 90-day average representation 658a and 365-day average representation 658b, where 90-day average indication 658a indicates an average for the last 90 days and 365-day average representation 658b indicates an average for the last 365 days (including the last 90 days). As depicted in FIG. 6G, each of 90-day average representation 658a and 365-day average representation 658b is a visually distinct line at a vertical location corresponding to a value of the corresponding average (e.g., because the average for the last 90 days is greater than the average for the last 365 days, 90-day average representation 658a is arranged at a vertical location higher than 365-day average representation 658b). In some examples, 90-day average representation 658a includes an indication regarding whether the average for the last 90 days is equal to or greater than the average for the last 365 days. For example, as depicted in FIG. 6G, 90-day average representation 658a includes "^," indicating that the average for the last 90 days is equal to or greater than the average for the last 365 days. Similarly, if the average for the last 90 days is lower than the average for the last 365 days, 90-day average representation 658a can include "V."

Detailed exercise user interface 652 includes daily averages representation 660 to compare activity data for the exercise activity metric for particular days of a week over the last 90 days and the last 365 days. In some examples, such as depicted in FIG. 6G, daily averages representation 660 includes a visual representation for comparing the activity data (e.g., a bar graph with x-axis corresponding to different days of the week and y-axis corresponding to an average value for the exercise activity metric over the last 90 days and the last 365 days). In such examples, the range of the y-axis is from 0 to a maximum average value over the last 365 days (e.g., 40, as depicted in FIG. 6G).

As depicted in FIG. 6G in daily averages representation 660, bars associated with time periods corresponding to the last 90 days are visually distinguished (e.g., different patterns or different colors) from bars associated with time periods corresponding to the last 365 days. In one example, the bars corresponding to the last 90 days are green while the bars corresponding to the last 365 days are gray. As depicted in FIG. 6G in weekly representation 658, bars associated with time periods (e.g., days within a week or hours within a day) within the last 90 days are paired (e.g., adjacent with no intervening representations) with bars associated with corresponding time periods within the last 365 days (e.g., a bar associated with Mondays within the last 90 days is paired with a bar associated with Mondays within the last 365 days.

Daily averages representation 660 includes textual representations (e.g., 660*a* and 660*b*) to correspond to the visual representation. For example, as depicted in FIG. 6A, daily averages representation 660 includes a table under the visual representation, with numbers corresponding to the bar graph, such as 32 and 38 being located such as to appear to corresponding to the Monday section of the bar graph. In some examples, numbers corresponding to the last 90 days are on a first line of the table and numbers corresponding to the last 365 days are on a second line, under the first line. In some examples, numbers corresponding to the last 90 days are visually distinct (e.g., different patterns or different colors) from numbers corresponding to the last 365 days. In one example, the numbers for the last 90 days are green while the numbers for the last 365 days are gray.

It should be recognized that some detailed activity metric user interfaces might not include a daily averages representation, such as detailed activity metric user interfaces corresponding to an action not often performed every day (e.g., running speed). For example, an action related to exercising can, instead of a daily averages representation, include a representation to compare activity data for an activity metric for a particular time period (other than days of a week) over the last 90 days and the last 365 days, such as hour, week, or month.

Detailed exercise user interface 652 includes exercise rings closed representation 662 to compare an activity metric associated with but different from the exercise activity metric. For example, exercise rings closed representation 662 relates to exercise rings closed, which is an activity metric corresponding to a predefined or user-defined threshold of an amount of exercise per day. In one example, exercise rings closed is associated with the exercise activity metric because an exercise ring closes based on the exercise activity metric exceeding a threshold in a given day.

Exercise rings closed representation 662 includes 90 days representation 662*a* and 365 days representation 662*b*. 90 days representation 662*a* includes a textual representation of a number of days out of the last 90 days that a user closed their exercise rings (e.g., "79/90 Days") and a percentage for the number of days out of the last 90 days (e.g., "88%"). 365 days representation 662*b* includes a textual representation of a number of days out of the last 365 days that a user closed their exercise rings (e.g., "284/365 Days") and a percentage for the number of days out of the last 365 days (e.g., "77%"). In some examples, 90 days representation 662*a* is visually distinguished from 365 days representation 662*b* (e.g., 90 days representation 662*a* is green and 365 days representation 662*b* is gray).

Figure 6H:
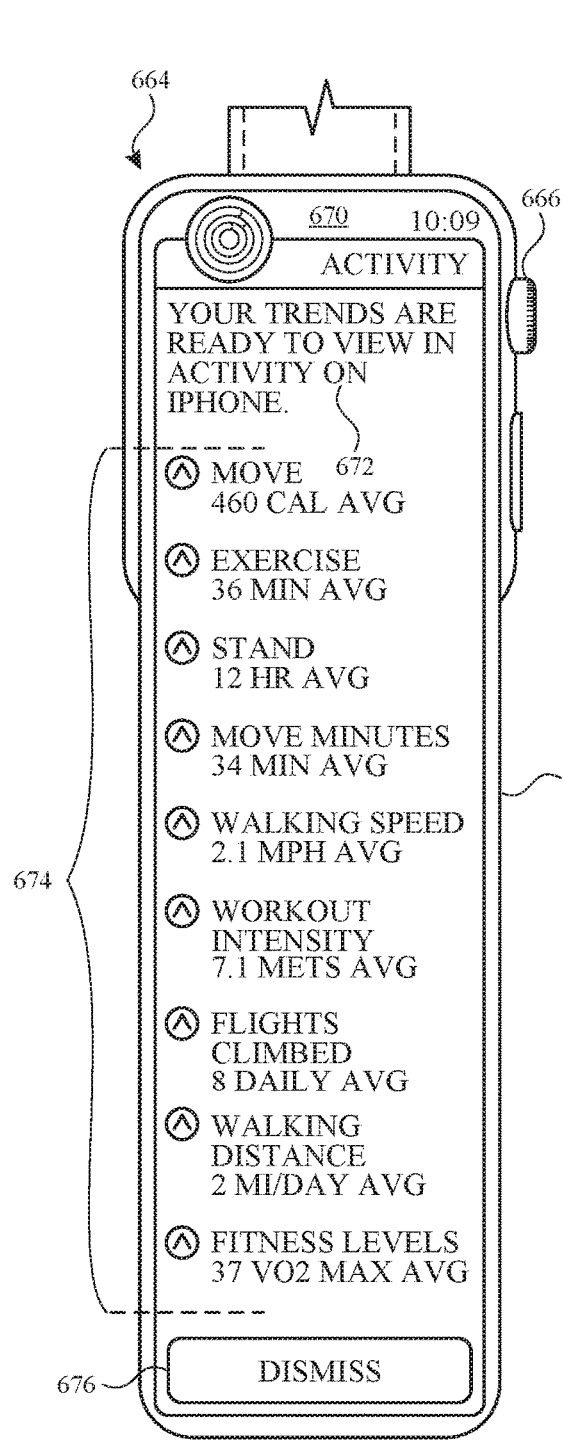
FIG. 6H depicts an electronic device displaying a ready-to-user user interface via a display device when activity trends are ready to be viewed on a second device.

FIG. 6H depicts electronic device 664 displaying ready-to-user user interface 670 via display device 668 when activity trends (e.g., such as depicted in FIG. 6D) are ready to be viewed on a second device (e.g., electronic device 600). In some examples, electronic device 664 includes one or more features of devices 100, 300, 500, or 600. In some examples, ready-to-user user interface 670 includes positive trend portion 674, with display of multiple representations for different activity metrics (e.g., move representation or exercise representation). As depicted in FIG. 6H, each representation includes an identification of an activity metric corresponding to the representation (e.g., "Move"), an icon corresponding to a comparison of the activity metric for the last 90 days as compared to the activity metric for the last 365 days (e.g., icon with "^"), and a value corresponding to a summary of the activity metric for the last 90 days (e.g., "460 cal avg"). In ready-to-user user interface 670 as depicted in FIG. 6H, all activity metrics have a positive trend within the last 90 days as compared to the last 365 days. It should be recognized that this is just an example and other combinations of all negative trends or a mix of some positive trends and some negative trends are possible.

Figure 6I:
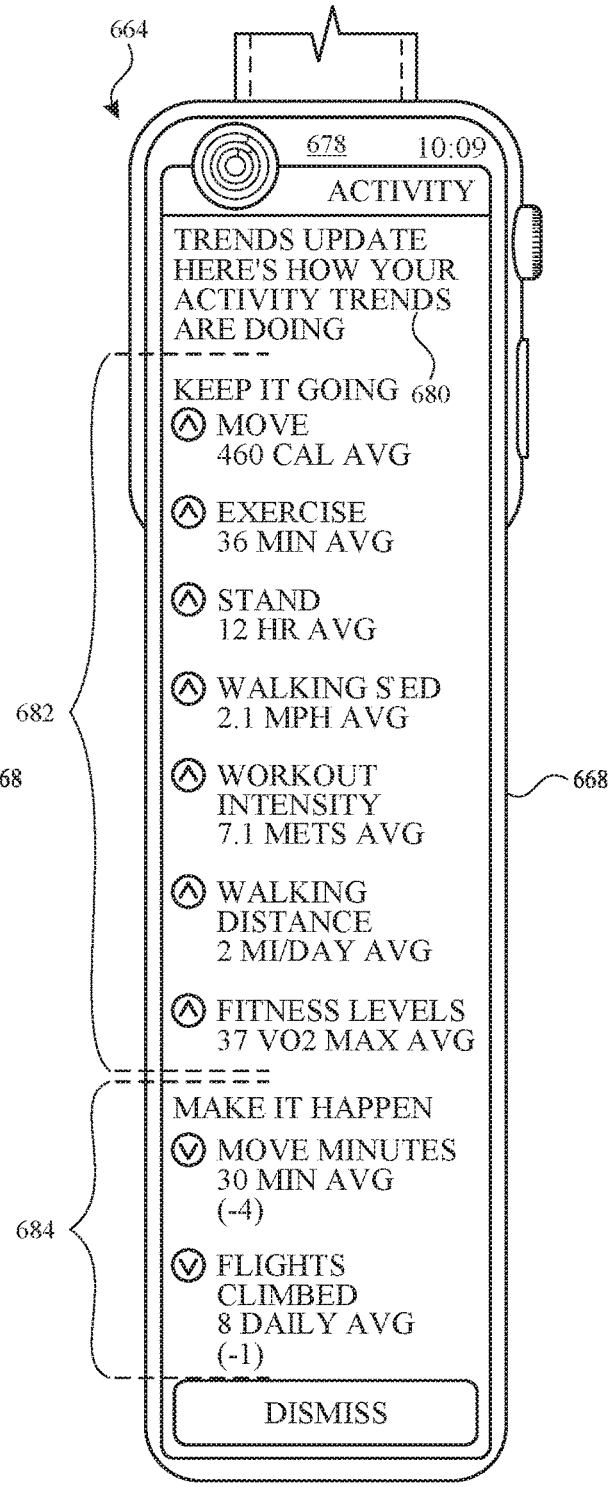
FIG. 6I depicts an electronic device displaying a mid-month-update user interface via a display device when activity trends are available to be viewed on a second device.

FIG. 6I depicts electronic device 664 displaying mid-month-update user interface 678 via display device 668 when activity trends (e.g., such as depicted in FIG. 6D) are available to be viewed on a second device (e.g., electronic device 600). In some examples, mid-month-update user interface 678 is pushed to be displayed via display device 668 (e.g., from electronic device 600) once per a particular time period (e.g., a month). However, it should be recognized that mid-month-update user interface 678 can be caused to be displayed at a different rate.

In some examples, mid-month-update user interface 678 includes positive trend portion 682 and negative trend portion 684, each with display of multiple representations for different activity metrics (e.g., move representation or exercise representation). As depicted in FIG. 6, each representation in positive trend portion 682 includes an identification of an activity metric corresponding to the representation (e.g., "Move"), an icon corresponding to a comparison of the activity metric for the last 90 days as compared to the activity metric for the last 365 days (e.g., icon with "^"), and a value corresponding to the comparison (e.g., "460 cal avg"). As depicted in FIG. 6I, each representation in negative trend portion 684 includes an identification of an activity metric corresponding to the representation (e.g., "Move minutes"), an icon corresponding to a comparison of the activity metric for the last 90 days as compared to the activity metric for the last 365 days (e.g., icon with "V"), a value corresponding to a summary of the activity metric for the last 90 days (e.g., "30 min avg"), and a difference between the summary of the activity metric for the last 90 days and a summary of the activity metric for the last 365 days (e.g., ("−4").

In mid-month-update user interface 678 as depicted in FIG. 6I, some activity metrics have a positive trend and other activity metrics have a negative trend within the last 90 days as compared to the last 365 days. It should be recognized that this is just an example and other combinations of all positive trends or all negative trends are possible.

FIGS. 7A-7B are a flow diagram illustrating method 700 for presenting activity trends (e.g., organizing activity metrics by trends (e.g., upwards/downwards) over time) using an electronic device in accordance with some embodiments. Method 700 relates to displaying a user interface (e.g., 90-day trend home page) with trend representation(s), each representation corresponding to a different activity metric, where placement of a trend representation is based on whether the trend representation is determined to currently be a first classification (e.g., no change or positive) or a second classification (e.g., negative). Method 700 is performed at a device (e.g., 100, 300, 500, 600, 664) with a display device. Some operations in method 700 are, optionally, combined, the orders of some operations are, optionally, changed, and some operations are, optionally, omitted.

As described below, method 700 provides an intuitive way for presenting activity trends. The method reduces the cognitive burden on a user for presenting activity trends, thereby creating a more efficient human-machine interface. For battery-operated computing devices, enabling a user to identify activity trends faster and more efficiently conserves power and increases the time between battery charges.

At 702, the device (e.g., 600, 664) receives activity data corresponding to a first activity metric (e.g., data corresponding to a measured level of activity for a user of the electronic device (e.g., data for activity performed by the user while wearing the electronic device)) for a first time period (e.g., 3 months).

At 704, the device receives activity data corresponding to the first activity metric for a second time period (e.g., 1 year) different from the first period of time.

At 706, the devices receives a request (e.g., 607 or 611) to display a first user interface (e.g., 612) (e.g., user interface that includes comparisons of activity data for a plurality of activity metrics).

At 708, the device, in response to receiving the request, displays, via the display device, the first user interface.

At 710, the first user interface includes, in accordance with a determination that a relationship (e.g., a mathematical relationship; a mathematical comparison) between the activity data corresponding to the first activity metric for the first time period and the activity data corresponding to the first activity metric for the second time period is a first type (e.g., the activity data (e.g., an average value of the activity data) for the first time period reflects no change or a positive change relative to the activity data (e.g., an average value of the activity data) for the second time period), displaying a representation (e.g., 636) (e.g., a graphical or textual indication of the first activity metric) of the first activity metric in a first portion (e.g., 626) of the first user interface.

At 712, the first user interface includes, in accordance with a determination that the relationship between the activity data corresponding to the first activity metric for the first time period and the activity data corresponding to the first activity metric for the second time period is a second type (e.g., the activity data for the first time period reflects a negative change relative to the activity data for the second time period) (e.g., negative), displaying the representation (e.g., 642) (e.g., up arrow or down arrow) of the first activity metric in a second portion (e.g., 636) of the first user interface different from the first portion (in some examples, representations determined to be of the first type are visually grouped within the user interface to be separate from representations determined to be of the second type). Dynamically placing a representation of an activity metric (e.g., in a first portion or a second portion of a user interface) based on a relationship between activity data associated with the activity metric over different time periods provides a user with visual feedback about a current state of the activity metric and data stored on a device. For example, such placement allows a user to quickly identify activity metrics for which the user has a negative trend recently. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, the relationship between the activity data corresponding to the first activity metric for the first time period and the activity data corresponding to the first activity metric for the second time period is the first type when an activity value (e.g., average, slope of a linear fit) determined (e.g., calculated) for the activity data corresponding to the first activity metric for the first time period is equal to or greater than an activity value (e.g., the same activity value determined for the first time period) determined for the activity data corresponding to the first activity metric for the second time period. In some examples, the relationship between the activity data corresponding to the first activity metric for the first time period and the activity data corresponding to the first activity metric for the second time period is the second type when the activity value determined for the activity data corresponding to the first activity metric for the first time period is less than the activity value determined for the activity data corresponding to the first activity metric for the second time period.

In some examples, the representation of the first activity metric includes a visual indication (e.g., a graphical indication (up or down arrow); a textual indication)) (e.g., 636b) of whether the relationship is the first type or the second type.

In some examples, displaying the first user interface includes, in accordance with a determination that the representation of the first activity metric is displayed in the first portion of the first user interface, animating the visual indication at a first time point (e.g., immediately on display, 0.5 seconds after display) after initially displaying the first user interface (e.g., automatically upon display of the first user interface). In some examples, displaying the first user interface includes, in accordance with a determination that the representation of the first activity metric is displayed in the second portion of the first user interface, animating the visual indication at a second time point (e.g., 1 second, a time point selected to be after the completion of the animation based on the first time point) after initially displaying the first user interface that is after the first time point. Animating visual indications (associated with activity metrics) such that visual indications associated with a first portion of a user interface are animated after visual indications associated with a second portion of the user interface (thereby highlighting such visual indications associated with the first behavior) provides a user with visual feedback about a current state of the activity metrics. For example, animating in such a way allows a user to quickly identify activity metrics for which the user has a negative trend recently. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, displaying the first user interface includes, in accordance with a determination that the activity data corresponding to the first activity metric meets a first set of data insufficiency criteria (e.g., data is not available for the first time period and/or the second time period) that includes a criterion that is met when the first activity metric is a first metric type (e.g., a metric that is infrequently provided for a percentage of users; a metric that is not directly measured by one or more sensors of the electronic device) and a criterion that is met when the first the activity data corresponding to the first activity metric is below a data sufficiency threshold (e.g., data for the first and/or second time period does not exist or exists, but does not meet a threshold amount requirement), forgoing display of the representation of the first activity metric in the first user interface (e.g., in the first portion and the second portion) (e.g., irrespective of a relationship between the activity data corresponding to the first activity metric for the first time period and the activity data corresponding to the first activity metric for the second time period is a first type).

In some examples, displaying the first user interface includes, in accordance with a determination that the activity data corresponding to the first activity metric meets a second set of data insufficiency criteria (e.g., data is not available for the first time period and/or the second time period) that includes a criterion that is met when the first activity metric is a second metric type (e.g., a metric that is frequently provided for a percentage of users, a metric that is directly measured by one or more sensors of the electronic device) and a criterion that is met when the activity data corresponding to the first activity metric is below the data sufficiency threshold (e.g., data for the first and/or second time period does not exist or exists, but does not meet a threshold amount requirement), displaying the representation of the first activity metric in a third portion (e.g., 618 or in a position in 612 as depicted in FIG. 6E other than positive trend portion 632 and negative trend portion 638)) of the user interface that is different from the first portion and the second portion with an indication (e.g., a graphical indication, a textual indication) that the activity data corresponding to the first activity metric is insufficient (e.g., irrespective of a relationship between the activity data corresponding to the first activity metric for the first time period and the activity data corresponding to the first activity metric for the second time period is a first type). Providing indications of whether a sufficient amount of data has been received for a particular activity metric provides a user with visual feedback about a current state of activity data stored on a device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, displaying the representation of the first activity metric in a third portion of the user interface includes displaying an indication of a predicted length of time remaining for the first activity data corresponding to the first activity metric to meet the data sufficiency threshold (e.g., 616) (in some examples, the predicted length of time is based on an assumption that a sufficient amount of activity data for the second activity metric will be received for the length of time). Indicating a predicted length of time needed to display a particular activity metric provides a user with visual feedback about a current state of activity data stored on a device and an indication regarding how the user needs to use the device in the future to be provided particular metrics. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, the first time period is a first predetermined period of time (e.g., the previous 90 days) prior to the current time (e.g., selected based on the current time (e.g., current day/date)). In some examples, the second time period is a second predetermined period of time (e.g., the previous 365 days) prior to the current time that is different from the first predetermined time period.

In some examples, displaying the representation of the first activity metric in a second portion (e.g., 642) of the first user interface includes displaying a first coaching indication (e.g., 642*e*) (e.g., "Let's get to walking 1 more mile per day") including a prediction corresponding to when (e.g., a period of time (e.g., 1 day, 5 days, 2 weeks) the relationship will transition from being of the second type (e.g., negative) to being of the first type (e.g., even or positive trend) while maintaining a future level (e.g., a predicted future level) of activity (e.g., 10% more walking per day) for the first activity metric. In some examples, displaying the representation of the first activity metric in a first portion of the first user interface includes forgoing display of the first coaching indication (in some examples, the representation displayed in the first portion includes a second coaching indication (e.g., "keep it up!"), different than the first coaching indication). Selectively providing a prediction regarding a user's activity level assists the user in performing a technical task of providing additional activity data, thereby providing the user with visual feedback about a current state of activity data stored on a device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, the electronic device includes a sensor device (e.g., an accelerometer, a GPS, a heart rate monitor). In such examples, the activity data corresponding to the first activity metric includes activity data received (e.g., detected) via the sensor device.

In some examples, the activity data corresponding to the first activity metric includes activity data received from a second electronic device (e.g., an external electronic device).

At 714, the device receives activity data corresponding to a third activity metric (e.g., data corresponding to a measured level of activity for a user of the electronic device (e.g., data for activity performed by the user while wearing the electronic device)) for the first time period (e.g., 3 months).

At 716, the device receives activity data corresponding to the third activity metric for the second time period (e.g., 1 year).

At 718, displaying the first user interface includes, in accordance with a determination that a relationship (e.g., a mathematical relationship; a mathematical comparison) between the activity data corresponding to the third activity metric for the first time period and the activity data corresponding to the third activity metric for the second time period is the first type (e.g., no change or positive), displaying a representation (e.g., a graphical or textual indication of the first activity metric) of the third activity metric in the first portion of the first user interface.

At 720, displaying the first user interface includes, in accordance with a determination that the relationship between the activity data corresponding to the third activity metric for the first time period and the activity data corresponding to the third activity metric for the second time period is the second type (e.g., negative), displaying a representation (e.g., up arrow or down arrow) of the third activity metric in the second portion of the first user interface.

In some examples, the representation of the first activity metric includes an indication in a first unit of measurement (e.g., calories, steps). In such examples, the representation of the third activity metric includes an indication in a second unit of measurement (e.g., minutes, miles) that is different than the first unit of measurement.

In some examples, the first time period (e.g., preceding 90 days) is a subset of the second time period (e.g., preceding 365 days).

In some examples, the relationship between the activity data corresponding to the first activity metric for the first time period and the activity data corresponding to the first activity metric for the second time period includes a comparison of an average of the activity data corresponding to the first activity metric for the first time period with an average of the activity data corresponding to the first activity metric for the second time period.

In some examples, the activity data corresponding to the first activity metric for the first time period is selected from a group consisting of one or more of: a number of calories burned, an amount of time for which a user has been detected exercising, a number of hours for which a user has been detected to be standing for at least one minute, an amount of time for which a user has moved, an amount of time for which a user has stood, a walking speed, an identified fitness level for a given time for a user, a number of flights of stairs climbed, a distanced walked, and a determined workout intensity for a user.

In some examples, the device displays a user interface with all positive (e.g., FIG. 6G) or all negative trends (e.g., FIG. 6D), where a user interface with all positive trends is different from a user interface with all negative trends and a user interface with a mix of positive and negative trends (e.g., FIG. 6E), and where a user interface with all negative trends is different from a user interface with a mix of positive and negative trends. In some examples, the order of trend representations is consistent between different views (e.g., all positive, all negative, or different combinations of mixes of positives and negatives). For example, in FIG. 6D, it can be seen that the order is move, exercise, stand, move minutes, and walk speed. Then, in FIG. 5E, while some of the representations for activity metrics have transitioned from negative to positive, the order within positive and the order within negative is maintained such that it keeps the order of move, exercise, stand, move minutes, and walk speed for each activity metric represented in each portion (e.g., in positive, the order is move, exercise, and move minutes, with stand missing because it is in the second portion). In some examples, the device displays a user interface with 10 different trends: move, exercise, stand, move minutes, stand minutes, walk speed, fitness levels, flights climbed, walking distance, and workout intensity. In some examples, negative trends include coaching information while positive trends do not include coaching information (e.g., 636 and 642).

Note that details of the processes described above with respect to method 700 (e.g., FIGS. 7A-7B) are also applicable in an analogous manner to the methods described below. For example, methods 800 and 900 optionally includes one or more of the characteristics of the various methods described above with reference to method 700. For example, selection of an activity representation in the first user interface described in method 700 can cause display of the first user interface described in method 800. For another example, one or more coaching indications described in method 900 can be included in the first user interface described in method 700. For brevity, these details are not repeated below.

FIGS. 8A-8B are a flow diagram illustrating method 800 for presenting activity trends (e.g., comparing an activity metric over two different lengths of time) using an electronic device in accordance with some embodiments. Method 800 relates to displaying a user interface (e.g., detailed page) with activity metric representations for a particular activity metric, comparing a first amount of time (e.g., 90 days) with a second amount of time (e.g., 365 days). Method 800 is performed at a device (e.g., 100, 300, 500, 600, 664) with a display device. Some operations in method 800 are, optionally, combined, the orders of some operations are, optionally, changed, and some operations are, optionally, omitted.

As described below, method 800 provides an intuitive way for presenting activity trends. The method reduces the cognitive burden on a user for presenting activity trends, thereby creating a more efficient human-machine interface. For battery-operated computing devices, enabling a user to identify activity trends faster and more efficiently conserves power and increases the time between battery charges.

At 802, the device (e.g., 600) receives activity data corresponding to a first activity metric (e.g., data corresponding to a measured level of activity for a user of the electronic device (e.g., data for activity performed by the user while wearing the electronic device)) for a first time period (e.g., 3 months).

At 804, the device receives activity data corresponding to the first activity metric for a second time period (e.g., 1 year), wherein the first time period is a subset of the second time period (e.g., the second time period includes the first time period). In some examples, at least some of the activity data is detected by a sensor of the electronic device. For example, the device includes a sensor device (e.g., an accelerometer, a GPS, a heart rate monitor) and the activity data corresponding to the first activity metric includes activity data received (e.g., detected) via the sensor device. In some examples, the activity data is received from a second electronic device. For example, the activity data corresponding to the first activity metric includes activity data received from a second electronic device (e.g., an external electronic device).

At 806, the device receives a request to display a first user interface (e.g., user interface with details for a specific activity metric) (e.g., 649).

At 808, the device, in response to receiving the request, displays, via the display device, the first user interface (e.g., 652).

At 810, the first user interface includes a representation (e.g., bars in 658 that are right of 658c) (e.g., a graphical or textual representation of a numerical value) (in some examples, the representation is a bar graph showing user activity data for the particular activity metric on each day within the first time period) of the activity data corresponding to the first activity metric for the first time period.

At 812, the first user interface includes a representation (e.g., bars in 658 that are left of 658c) (e.g., a graphical or textual representation of a numerical value) (in some examples, the representation is a bar graph showing user activity data for the particular activity metric on each day within the second time period) of the activity data corresponding to the first activity metric for the second time period.

In some examples, the representation of the activity data corresponding to the first activity metric for the first time period is visually distinct (e.g., includes a visual characteristic (e.g., a color, a border, a shape) that is not present in the representation for the second time period or lacks a visual characteristic that is present in the representation for the second time period) from the representation of the activity data corresponding to the first activity metric for the second time period.

At 814, the first user interface includes a representation (e.g., 656*a*, 656*b*, 656*d*, 656*e*, 658*a*) (e.g., a graphical or textual representation of a numerical value) of a comparison (e.g., a mathematical comparison) of the activity data corresponding to the first activity metric for the first time period and the activity data corresponding to the first activity metric for the second time period. Displaying representations regarding different activity metrics with a comparison of activity data over different time periods provides a user with visual feedback about a current state of activity data stored on a device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, at 816, displaying the first user interface includes displaying an indication (e.g., 658*a*) (e.g., a textual or graphical indication) for an average of the activity data corresponding to the first activity metric for the first time period. In such an example, at 818, displaying the first user interface includes displaying an indication (e.g., 658*b*) (e.g., a textual or graphical indication) for an average of the activity data corresponding to the first activity metric for the second time period.

In some examples, the representation of the activity data corresponding to the first activity metric for the first time period is divided into a first number of representations (e.g., a number of representations corresponding to a unit (e.g., days) of the time period). In such an example, the representation of the activity data corresponding to the first activity metric for the second time period is divided into a second number of representations different from the first number of representations.

In some examples, the representation of the comparison indicates a difference between the activity data (e.g., a difference between an activity value (e.g., average, slope of a linear fit) determined (e.g., calculated) for the first and second time periods for the activity data) corresponding to the first activity metric for the first time period and the activity data corresponding to the first activity metric for the second time period (in some examples, the representation of the comparison indicates a difference only when the activity data for the first time period is less than the activity data for the second time period).

In some examples, at 820, displaying the first user interface includes displaying a plurality of first-time-period representations for the first time period (e.g., empty bars in 660) (e.g., bars in a graph for each day of the week corresponding to 90 day period), wherein: a first first-time-period representation (e.g., Monday bar for 90 day period) corresponds to a length of time (e.g., a day), a second first-time-period representation (e.g., Tuesday bar for 90 day period) corresponds to the length of time, the first first-time-period representation corresponds to a third time period (e.g., each Monday within the 90 day period) within the first time period, and the second first-time-period representation corresponds to a fourth time period (e.g., each Tuesday within the 90 day period) within the first time period. In such an example, at 822, displaying the first user interface includes displaying a plurality of second-time-period representations for the second time period (e.g., bars with diagonal lines in 660) (e.g., bars in a graph for each day of the week corresponding to 365 day period), wherein: a first second-time-period representation (e.g., Monday bar for 365 day period) corresponds to the length of time, a second second-time-period representation (e.g., Tuesday bar for 365 day period) corresponds to the length of time, the first second-time-period representation corresponds to a fifth time period (e.g., each Monday within the 365 day period) within the second time period, the second second-time-period representation corresponds to a sixth time period (e.g., each Tuesday within the 365 day period) within the second time period, the third time period corresponds to the fifth time period (e.g., both are Mondays within their respective time periods), the fourth time period corresponds to the sixth time period (e.g., both are Tuesdays within their respective time periods), the first first-time-period representation is visually paired with (e.g., displayed adjacent to (e.g., without any other intervening representations)) the first second-time-period representation, and the second first-time-period representation is visually paired with the second second-time-period representation. Visually depicting a user's activity over time using a comparison of two different time periods provides a user with visual feedback about a current state of activity data stored on a device and information regarding how the user uses the device over time. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, at 824, displaying the first user interface includes displaying a representation (e.g., 662*a*) of a percentage of time periods of a particular length (e.g., a day) of the activity data corresponding to the first activity metric (e.g., calories burned) for the first time period for which (e.g., during which) the first activity metric met a threshold activity level (e.g., 500 calories/day) (in some examples, the user interface includes a percentage of days during a 90 day period in which the value of a activity metric (e.g., calories burned) met a threshold value (e.g., 85% of the days logged a calories burned metric of greater than 500 calories). Linking an activity metric with a particular threshold and tracking a user's past ability to meet the threshold provides a user with visual feedback about how the user uses the device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, at 824, displaying the first user interface includes displaying an icon (e.g., 656*b*) indicating whether a relationship (e.g., a mathematical relationship; a mathematical comparison) between the activity data corresponding to the first activity metric for the first time period and the activity data corresponding to the first activity metric for the second time period is a first type (e.g., the activity data (e.g., an average value of the activity data) for the first time period reflects no change or a positive change relative to the activity data (e.g., an average value of the activity data) for the second time period) or a second type (e.g., the activity data for the first time period reflects a negative change relative to the activity data for the second time period).

Note that details of the processes described above with respect to method 800 (e.g., FIGS. 8A-8B) are also applicable in an analogous manner to the methods described below. For example, methods 700 and 900 optionally includes one or more of the characteristics of the various methods described above and below with reference to method 800. For example, selection of a back affordance in the first user interface described in method 900 can cause display of the first user interface described in method 700. For another example, one or more coaching indications described in method 900 can be included in the first user interface described in method 800. For brevity, these details are not repeated below.

FIG. 9 is a flow diagram illustrating method 900 for presenting activity trends (e.g., providing different coaching depending on relationship between data of time periods; coaching includes a prediction of when relationship will change, if certain activity level is maintained) using an electronic device in accordance with some embodiments. Method 900 is performed at a device (e.g., 100, 300, 500, 600, 664) with a display device. Some operations in method 900 are, optionally, combined, the orders of some operations are, optionally, changed, and some operations are, optionally, omitted.

As described below, method 900 provides an intuitive way for presenting activity trends. The method reduces the cognitive burden on a user for presenting activity trends, thereby creating a more efficient human-machine interface. For battery-operated computing devices, enabling a user to identify activity trends faster and more efficiently conserves power and increases the time between battery charges.

At 902, the device (e.g., 600) receives activity data corresponding to a first activity metric (e.g., data corresponding to a measured level of activity for a user of the electronic device (e.g., data for activity performed by the user while wearing the electronic device)) for a first time period (e.g., 3 months).

At 904, the device receives activity data corresponding to the first activity metric for a second time period (e.g., 1 year), different than the first period of time.

At 906, the device receives a request (e.g., 607, 611, 649) to display a first user interface (e.g., 612, 652) (e.g., user interface that includes comparisons of activity data for a plurality of activity metrics or user interface with details for a specific activity metric).

At 908, the device, in response to receiving the request, displays, via the display device, the first user interface, the first user interface including a representation (e.g., 642, or 656) (e.g., a graphical or textual indication of the first activity metric) of the first activity metric.

At 910, the representation of the first activity metric includes, in accordance with a determination that a relationship (e.g., a mathematical relationship; a mathematical comparison) between the activity data corresponding to the first activity metric for the first time period and the activity data corresponding to the first activity metric for the second time period is a first type (e.g., negative trend for which can be remedied within 1 day), displaying a first coaching indication (e.g., 628e) (e.g., "Don't forget to stand for one minute per hour throughout the day") including a prediction (e.g., "the day" the 628) corresponding to when (e.g., a period of time (e.g., 1 day, 5 days, 2 weeks) the relationship will transition from being of the first type to being of a second type (e.g., even or positive trend), different from the first type, while maintaining a future level of activity (e.g., 10% more walking per day) for the first activity metric.

At 912, the representation of the first activity metric includes, in accordance with a determination that the relationship is a third type (e.g., negative trend for which can be remedied more than a week but within 1 month) different from the first type, a second coaching indication (e.g., 624e) (e.g., "Try to move around for 10 extra minutes") that does not include a prediction corresponding to when (e.g., a period of time (e.g., 1 day, 5 days, 2 weeks) the relationship will transition from being of the third type to being of the second type. Dynamically modifying activity-related information provided to a user based on classifying the user's activity provides a user with visual feedback about a current state of activity data stored on a device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, the first type requires that the relationship between the activity data (e.g., relationship between an activity value (e.g., average, slope of a linear fit) determined (e.g., calculated) for the activity data corresponding to the first activity metric for the first time period and the second time period)) corresponding to the first activity metric for the first time period and the activity data corresponding to the first activity metric for the second time period is negative (e.g., the average value for the first time period is 50 calories burned/day and the average value for the second time period is 75 calories burned/day with a difference in the values being −25 calories burned/day)).

In some examples, the representation of the first activity metric includes: while the relationship between the activity data corresponding to the first activity metric for the first time period and the activity data corresponding to the first activity metric for the second time period is the first type (this in accordance means that the trend is negative): in accordance with a determination that a relationship between the activity data corresponding to the first activity metric for the second time period and the activity data corresponding to the first activity metric for a subset of the first time period (e.g., the last 7 days in a 90 day period) is a fourth type (e.g., recently positive), displaying a third coaching indication (e.g., "You have been improving lately, but let's get to walking 1 more mile per day to reach your yearly average"; a coaching indication in addition to the first coaching indication); and in accordance with a determination that a relationship between the activity data corresponding to the first activity metric for the second time period and the activity data corresponding to the first activity metric for the subset of the first time period (e.g., the last 7 days in a 90 day period) is a fifth type (e.g., recently negative), displaying a fourth coaching indication that is different from the third coaching indication (e.g., "let's get to walking 1 more mile per day to reach your yearly average"). Dynamically modifying activity-related information provided to a user based on a user's recent behavior as compared to less recent behavior provides a user with visual feedback about a recent state of activity data stored on a device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, the representation of the first activity metric includes: while the relationship between the activity data corresponding to the first activity metric for the first time period and the activity data corresponding to the first activity metric for the second time period is the first type: in accordance with a determination that the prediction exceeds a first time threshold (e.g., >1 day) and is less than a second time threshold (e.g., <7 days), displaying a fifth coaching indication (e.g., a coaching indication in addition to the first coaching indication); and in accordance with a determination that the prediction exceeds the second time threshold (e.g., >7 days), displaying a sixth coaching indication (e.g., a coaching indication in addition to the first coaching indication) that is different from the fifth coaching indication. Dynamically modifying activity-related information provided to a user based on a link of time predicted for the activity data to be similar to the past provides a user with visual feedback about a current state of activity data stored on a device. Providing improved visual feedback to the user enhances the operability of the device and makes the user-device interface more efficient (e.g., by helping the user to identify what type of data the user needs to provide a device to change the user interface and reducing user mistakes when operating/interacting with the device) which, additionally, reduces power usage and improves battery life of the device by enabling the user to use the device more quickly and efficiently.

In some examples, at 914, the device, while the relationship between the activity data corresponding to the first activity metric for the first time period and the activity data corresponding to the first activity metric for the second time period is the first type (this in accordance means that the trend is negative): in accordance with a determination that the prediction is a first classification (e.g., requiring a level of activity that exceeds threshold (e.g., an unreasonably high requirement)), displaying a fifth coaching indication (e.g., "Do better") without a prediction corresponding to when the relationship between the activity data corresponding to the first activity metric for the first time period and the activity data corresponding to the first activity metric for the second time period will be of the second type (e.g., even or positive trend) while maintaining the future level of activity (e.g., 10% more walking per day) for the first activity metric.

In some examples, the prediction is determined by: removing old data from the activity data corresponding to the first activity metric for the first time period, removing old data from the activity data corresponding to the first activity metric for the second time period, and until the relationship between the activity data corresponding to the first activity metric for the first time period and the activity data corresponding to the first activity metric for the second time period is the second type, adding predicted data to the activity data corresponding to the first activity metric for the first time period, and adding the old data from the activity data corresponding to the first activity metric for the first time period to the activity data corresponding to the first activity metric for the second time period (in some examples, trend reverses in 1 day, which only requires taking the last actual 89/364 days of data and adding one predicted day).

Note that details of the processes described above with respect to method 900 (e.g., FIG. 9) are also applicable in an analogous manner to the methods described below. For example, methods 700 and 800 optionally includes one or more of the characteristics of the various methods described above with reference to method 900.

FIGS. 10A-10N illustrate exemplary user interfaces for managing workouts, in accordance with some embodiments. The user interfaces in these figures are used to illustrate the processes described below, including the processes in FIGS. 11A-11B.

FIG. 10A depicts electronic device 1000 displaying watch face user interface 1004 via display device 1002. Electronic device 1000 includes various input mechanisms that receive user input, such as rotatable input mechanism 1001, which is able to receive a rotatable input (and, in some examples, can also receive a push input). In some examples, electronic device 1000 includes one or more features of devices 100, 300, or 500. Watch face user interface 604 includes workout affordance 1006 for initiating a workout application (e.g., an application to track workouts performed by a user associated with electronic device 1000).

Referring to FIG. 10A, electronic device 1000 receives user input 1007 corresponding to selection of workout affordance 1006. User input 1007 can include a touch gesture, such as a tap gesture on workout affordance 1006, causing the workout application to be initiated (e.g., display of a user interface of the workout application, such as workout platter user interface 1008 as depicted in FIG. 10B).

FIG. 10B depicts electronic device 1000 displaying workout platter user interface 1008 via display device 1002. Workout platter user interface 1008 includes scrollable list of affordances 1010, which are each associated with a respective physical activity tracking function for a physical activity. For example, scrollable list of affordances 1010 includes walk affordance 1012a, which corresponds to a physical activity tracking function for an outdoor walk.

It is noted that scrollable list of affordances 1010 includes additional affordances corresponding to other physical activity tracking functions that are not currently displayed but can be displayed in response to a scrolling input (e.g., rotation of rotational mechanism 1001). In some embodiments, scrollable list of affordances 1010 includes more workouts affordance, which will be described in further detail below (see at least FIG. 10F).

Referring to FIG. 10B, electronic device 1000 receives user input 1013 corresponding to selection of walk affordance 1012a. User input 1013 can include a touch gesture, such as a tap gesture on walk affordance 1012a, causing a physical activity tracking function associated with walk affordance 1012a to be launched (e.g., display of one or more user interfaces of the workout application, with a final user interface corresponding to the physical activity tracking function associated with walk affordance 1012a (e.g., walk user interface 1014 as depicted in FIG. 10C).

FIG. 10C depicts electronic device 1000 displaying walk user interface 1014 via display device 1002. Walk user interface 1014 displays a set of tracked metrics (e.g., "00: 01.40," "0 active cal," "70 BPM," "15'11"average mile," and "0 ft") (which are tracked by the physical activity tracking function associated with walk affordance 1012a.

In some examples, tracking of the set of tracked metrics is performed by one or more tracking sensors of electronic device 1000. For example, electronic device 1000 tracks physical activity via tracking sensors (or workout sensors) that communicate with workout support module 142 (as depicted in FIG. 3).

Referring to FIG. 10C, electronic device 1000 receives user input 1015 corresponding to a swipe gesture. User input 1015 can include a touch gesture, causing a control user interface of the workout application to be displayed (e.g., control user interface 1016 as depicted in FIG. 10D).

FIG. 10D depicts electronic device 1000 displaying control user interface 1016 via display device 1002. In some examples, device 1000 displays control user interface 1016 in response to a user input (e.g., user input 1015) while displaying walk user interface 1014. Control user interface 1016 includes affordances to control various functionalities of the workout application. For example, control user interface 1016 includes end workout affordance 1018 (configured to, when selected, end a currently running workout).

Figure 10E:
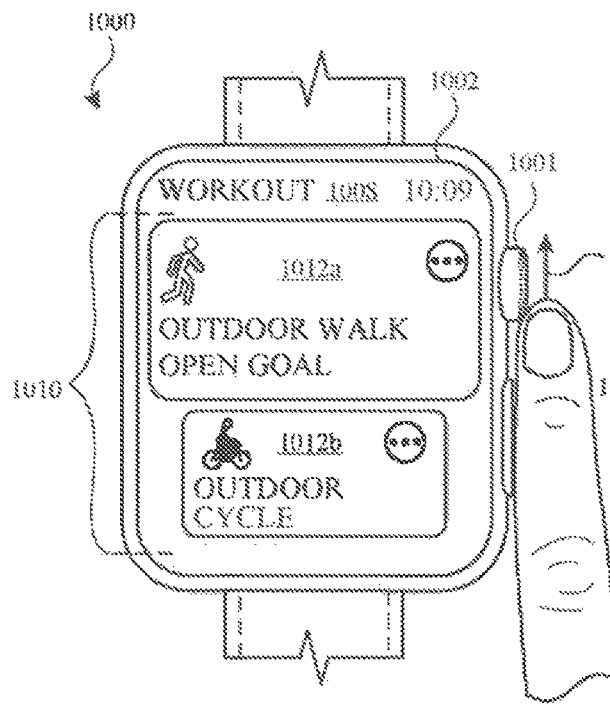
FIG. 10E depicts an electronic device displaying a workout platter user interface via a display device 1002 and performing a scrolling operation.
Figure 11A:
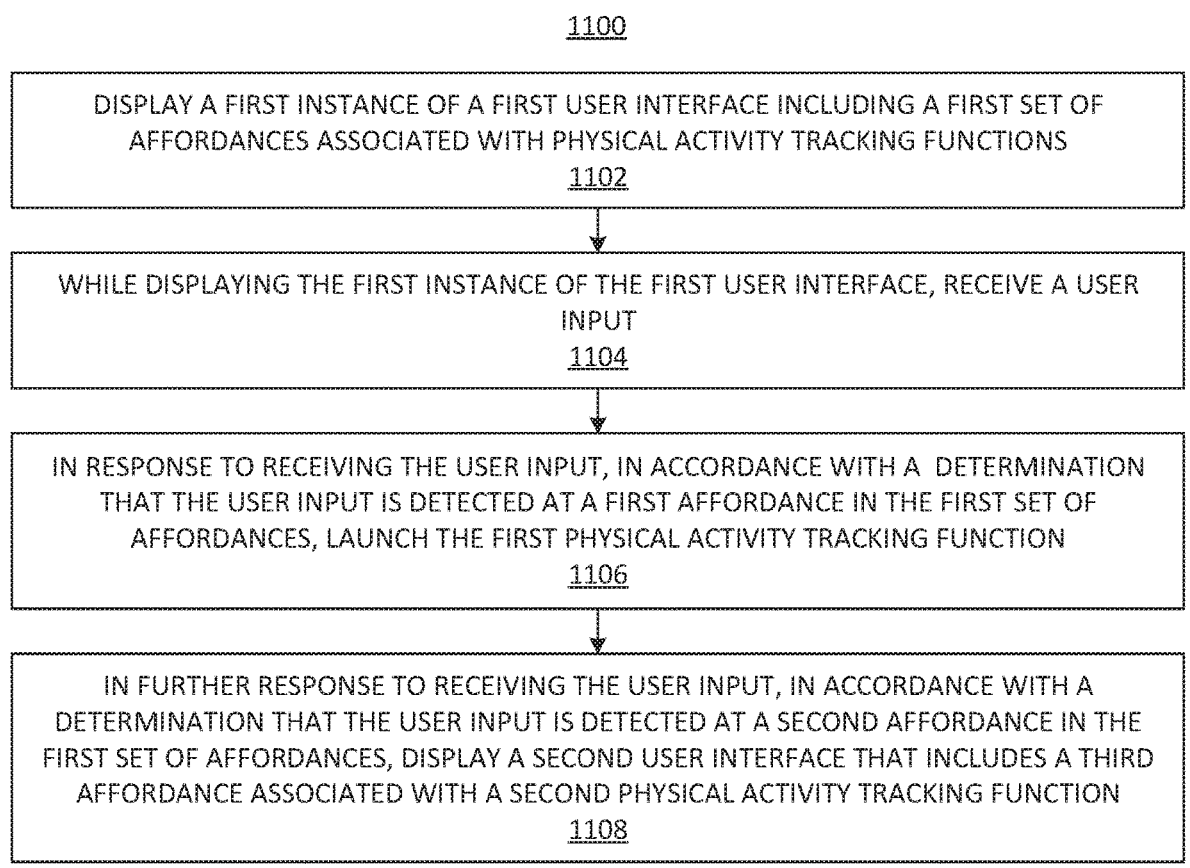

Referring to FIG. 10D, electronic device 1000 receives user input 1019 corresponding to selection of end workout affordance 1018. User input 1019 can include a touch gesture, such as a tap gesture on end workout affordance 1018, causing the currently running workout (associated with outdoor walk) to end and workout platter user interface 1008 to be displayed, as depicted in FIG. 10E.

FIG. 10E depicts electronic device 1000 displaying, once again, workout platter user interface 1008 via display device 1002 and performing a scrolling operation. For example, rotational input 1021 is received at rotatable input mechanism 1001. In response to rotational input 1021, as depicted in FIG. 10F, scrollable list of affordances 1010 is scrolled in an upward direction such that more workouts affordance 1022 are displayed.

Figure 10F:
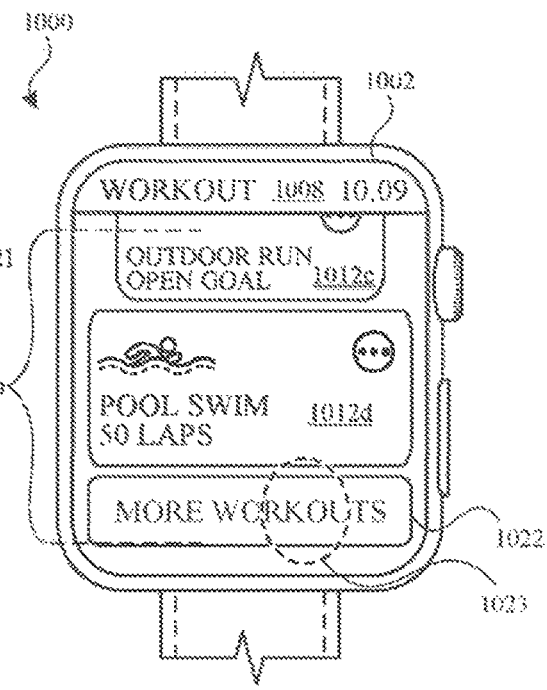
FIG. 10F depicts an electronic device receiving user input corresponding to selection of a more workouts affordance.

Referring to FIG. 10F, electronic device 1000 receives user input 1023 corresponding to selection of more workouts affordance 1022. User input 1023 can include a touch gesture, such as a tap gesture on more workouts affordance 1022, causing a user interface with a list of available workouts to be displayed (e.g., workout list user interface 1024 as depicted in 10G).

Figure 10G:
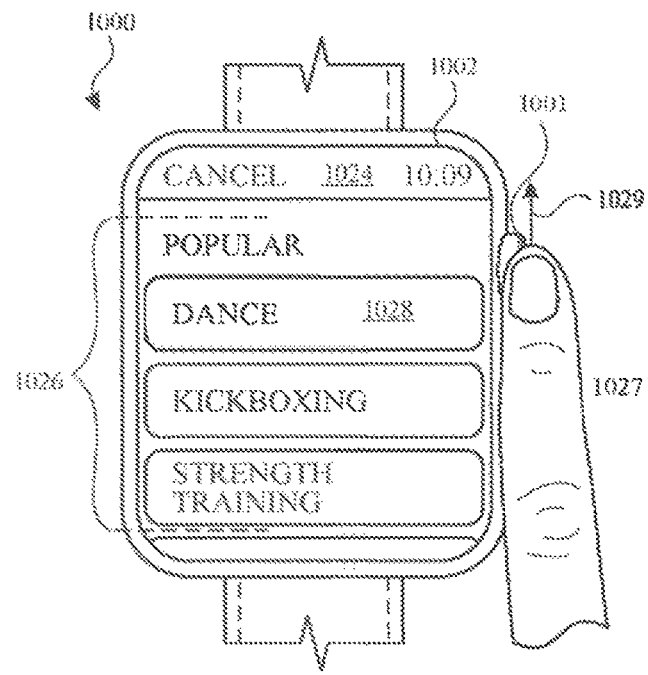
FIG. 10G depicts an electronic device displaying a workout list user interface via a display device.

FIG. 10G depicts electronic device 1000 displaying workout list user interface 1024 via display device 1002. In some examples, workout list user interface 1024 includes a scrollable list of affordances with popular portion 1026 (as depicted in FIG. 10G) and alphabetical portion 1027 (as depicted in FIG. 10H).

Referring to FIG. 10G, popular portion 1026 includes multiple workout affordances, each workout affordance determined to be most relevant (e.g., popular among users, most frequently used by a user associated with electronic device 1000, etc.). For example, the multiple workout affordances in popular portion 1026 includes dance affordance 1028. Selection of a particular workout affordance of the multiple workout affordances causes (1) a workout affordance corresponding to the particular workout affordance to be added to workout platter user interface 1008 such that the workout affordance can be selected in the future when a user navigates to workout platter user interface 1008 and/or (2) a physical activity tracking function corresponding to the workout affordance to be launched.

Figure 10H:
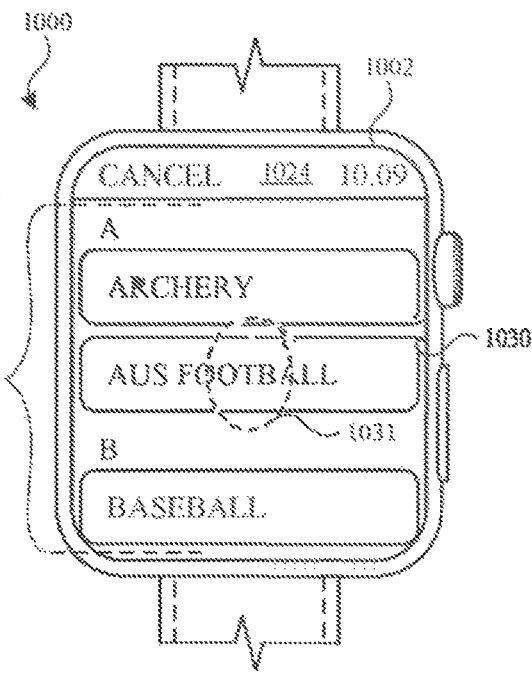
FIG. 10H depicts an electronic device receiving user input corresponding to selection of an AUS football affordance.

Referring to FIG. 10H, alphabetical portion 1027 includes a list of workout affordances in alphabetical order, including AUS football affordance 1030 (e.g., an affordance corresponding to function for tracking activity associated with Australian rules football). It should be recognized that the list of workout affordances can be ordered in a different manner. Similar to popular portion 1026, selection of a particular workout affordance in the list of workout affordances causes (1) a workout affordance corresponding to the particular workout affordance to be added to workout platter user interface 1008 such that the workout affordance can be selected in the future when a user navigates to workout platter user interface 1008 and/or (2) a physical activity tracking function corresponding to the workout affordance to be launched.

Similar to as described above for FIG. 10E, FIG. 10F depicts electronic device 1000 receiving rotational input 1029 at rotatable input mechanism 1001. In response to rotational input 1029, the scrollable list of affordances of workout list user interface 1024 is scrolled in an upward direction such that more workout affordances are displayed (e.g., other workout affordances in popular portion 1026 (not depicted) or workout affordances in alphabetical portion 1021 (as depicted in FIG. 10H)).

FIG. 10H depicts electronic device 1000 receiving user input 1031 corresponding to selection of AUS football affordance 1030. User input 1031 can include a touch gesture, such as a tap gesture on AUS football affordance 1030, causing a workout affordance corresponding to AUS football affordance 1030 to be added to workout platter user interface 1008 (e.g., AUS football affordance 1034 as depicted in FIG. 10I).

Similar as described above for FIGS. 10B-10D, FIGS. 10I-10K depict user interfaces involved in beginning and ending a workout. For example, FIG. 10I depicts electronic device 1000 displaying workout platter user interface 1008 via display device 1002. Workout platter user interface 1008 depicted in FIG. 10I includes AUS football affordance 1034, showing that workout platter user interface 1008 depicted in FIG. 10I is in a state after AUS football affordance 1034 has been added to workout platter user interface 1008 (e.g., after FIG. 10H) (see FIG. 10F, which does not include AUS football affordance 1034). AUS football affordance 1034 corresponds to a physical activity tracking function for Australian football.

Figure 10I:
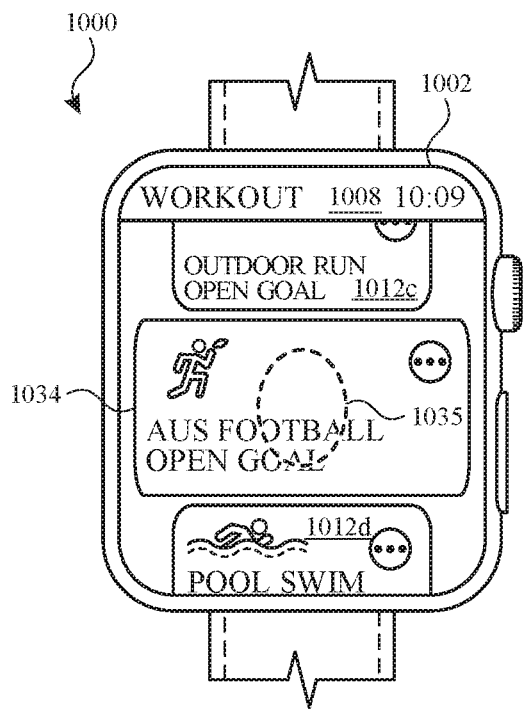
FIG. 10I depicts an electronic device displaying a workout platter user interface via a display device.

Referring to FIG. 10I, electronic device 1000 receives user input 1035 corresponding to selection of AUS football affordance 1034. User input 1035 can include a touch gesture, such as a tap gesture on AUS football affordance 1034, causing a physical activity tracking function associated with AUS football affordance 1034 to be launched (e.g., display of one or more user interfaces of the workout application, with a final user interface corresponding to the physical activity tracking function associated with AUS football affordance 1034 (e.g., AUS football user interface 1036 as depicted in FIG. 10J).

Figure 10J:
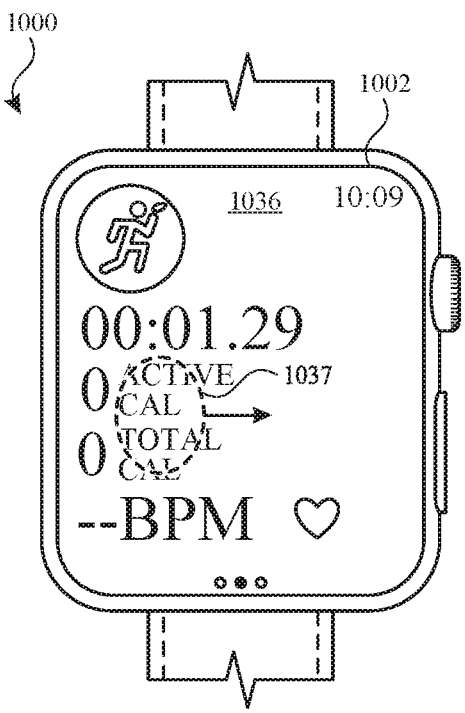
FIG. 10J depicts an electronic device displaying an AUS football interface via a display device 1002.

FIG. 10J depicts electronic device 1000 displaying AUS football interface 1036 via display device 1002. AUS football interface 1036 displays a set of tracked metrics (e.g., "00:01.29," "0 active cal," "0 total cal," and "—BPM") (which are tracked by the physical activity tracking function associated with AUS football affordance 1034).

In some examples, tracking of the set of tracked metrics is performed by one or more tracking sensors of electronic device 1000. For example, electronic device 1000 tracks physical activity via tracking sensors (or workout sensors) that communicate with workout support module 142 (as depicted in FIG. 3).

Referring to FIG. 10J, electronic device 1000 receives user input 1037 corresponding to a swipe gesture. User input 1037 can include a touch gesture, causing a control user interface of the workout application to be displayed (e.g., control user interface 1038 as depicted in FIG. 10K).

Figure 10K:
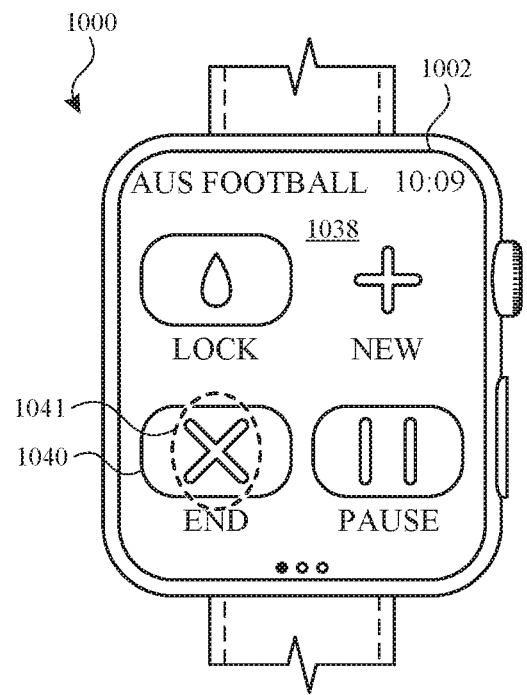
FIG. 10K depicts an electronic device displaying a control user interface via a display device.

FIG. 10K depicts electronic device 1000 displaying control user interface 1038 via display device 1002. Control user interface 1038 includes affordances to control various functionalities of the workout application. For example, control user interface 1038 includes end workout affordance 1040 (configured to, when selected, end a currently running workout).

Referring to FIG. 10K, electronic device 1000 receives user input 1041 corresponding to selection of end workout affordance 1040. User input 1041 can include a touch gesture, such as a tap gesture on end workout affordance 1040, causing the currently running workout (associated with Australian football) to end and workout platter user interface 1008 to be displayed, as depicted in FIG. 10L.

Figure 10L:
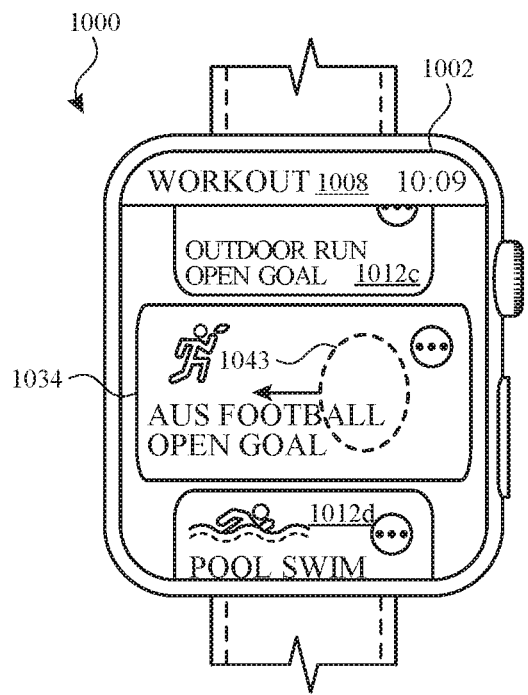
FIG. 10L depicts an electronic device displaying a workout platter user interface via a display device.

FIG. 10L depicts electronic device 1000 displaying workout platter user interface 1008 via display device 1002. Workout platter user interface 1008 depicted in FIG. 10L includes AUS football affordance 1034, showing that workout platter user interface 1008 depicted in FIG. 10L is in a state after AUS football affordance 1034 has been added to workout platter user interface 1008 (e.g., after FIG. 10H) (see FIG. 10F, which does not include AUS football affordance 1034).

Referring to FIG. 10L, electronic device 1000 receives user input 1043 corresponding to a swipe gesture associated with (e.g., at least partially on top of) AUS football affordance 1034. User input 1043 can include a touch gesture, causing (1) AUS football affordance 1034 to move to the left and (2) delete affordance 1044 to be displayed in a position that was at least partially previously occupied by AUS football affordance 1034 prior to moving (as depicted in FIG. 10M).

Figure 10M:
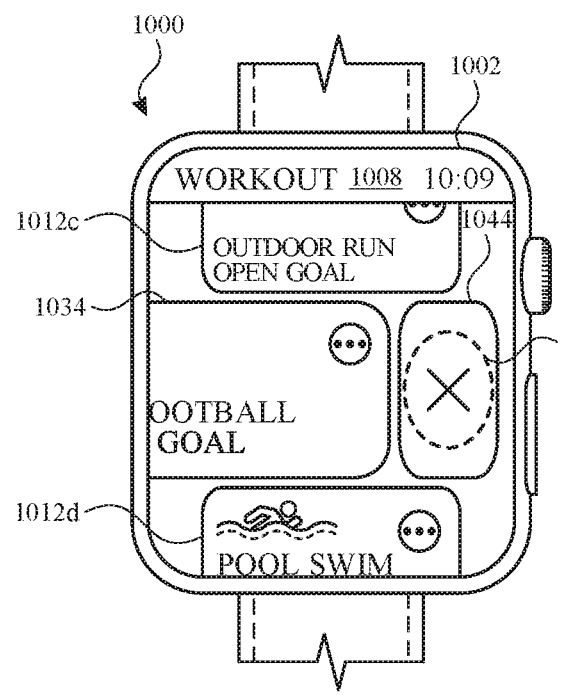
FIG. 10M depicts an electronic device displaying a workout platter user interface via a display device with an AUS football affordance moved to the left and a delete affordance displayed in a location that was at least partially covered up by the AUS football affordance prior to being moved to the left.
Figure 10N:
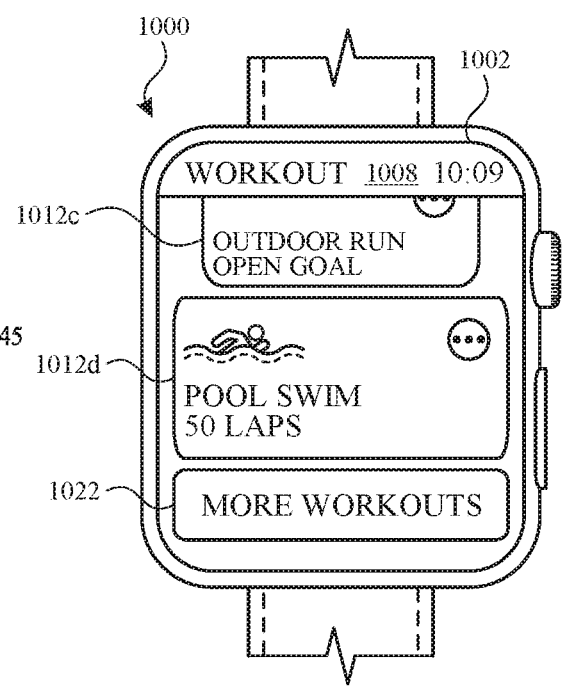
FIG. 10N depicts an electronic device displaying a workout platter user interface via a display device without an AUS football affordance.

FIG. 10M depicts electronic device 1000 displaying workout platter user interface 1008 via display device 1002 with AUS football affordance 1034 moved to the left and delete affordance 1044 displayed in a location that was at least partially covered up by AUS football affordance 1034 prior to being moved to the left. Referring to FIG. 10L, electronic device 1000 receives user input 1045 corresponding to selection of delete affordance 1040. User input 1041 can include a touch gesture, such as a tap gesture on end workout affordance 1044, causing AUS football affordance 1034 to be removed from workout platter user interface 1008 (as depicted in FIG. 10N) until AUS football affordance 1034 is added again using the process described in FIGS. 10F-10H. FIG. 10N depicts electronic device 1000 displaying workout platter user interface 1008 via display device 1002 without AUS football affordance 1034.

FIGS. 1A-11B are a flow diagram illustrating method 1100 for managing workouts (e.g., more-workouts option for workout platters, allowing user to view a list of workouts to add to workout platters) using an electronic device in accordance with some embodiments. Method 1100 is performed at a device (e.g., 100, 300, 500, 600, 664, 1000) with a display device. Some operations in method 1100 are, optionally, combined, the orders of some operations are, optionally, changed, and some operations are, optionally, omitted.

As described below, method 1100 provides an intuitive way for managing workouts. The method reduces the cognitive burden on a user for managing workouts, thereby creating a more efficient human-machine interface. For battery-operated computing devices, enabling a user to add and delete workout affordances associated with physical activity tracking functions faster and more efficiently conserves power and increases the time between battery charges.

At 1102, the device (e.g., 1000) displays, via the display device, a first instance of a first user interface (e.g., 1008 as depicted in FIGS. 10B, 10E, and 10F) including a first set of affordances (e.g., 1012a, 1012b) (e.g., workout platters) associated with physical activity tracking functions (in some examples, different affordances in a plurality of the scrollable list of affordances correspond to different physical activities), wherein the first set of affordances includes a first affordance (e.g., 1012a) associated with a first physical activity tracking function.

At 1104, while displaying the first instance of the first user interface, the device receives a user input (e.g., 1013) (e.g., a tap in the user interface).

At 1106, in response to receiving the user input, in accordance with a determination that the user input is detected at the first affordance (e.g., run option) in the first set of affordances, the device launches (e.g., activating, starting) the first physical activity tracking function (e.g., 1014) (e.g., running).

At 1108, in further response to receiving the user input, in accordance with a determination that the user input is detected at a second affordance (e.g., 1022) (e.g., more-workouts option) in the first set of affordances, the device displays a second user interface (e.g., 1024) (e.g., more-workouts interface) that includes a third affordance (e.g., 1030) associated with a second physical activity tracking function (e.g., walking option).

At 1110, the device receives a set of one or more inputs (e.g., 1031), the set of one or more inputs including an input corresponding to selection of the third affordance.

At 1112, in response to receiving the set of one or more inputs, the device displays a second instance (e.g., 1008 as depicted in FIG. 10I) of first user interface, wherein: the second instance of the first user interface includes the first affordance and a fourth affordance (e.g., 1034) associated with the second physical activity tracking function (e.g., an affordance that, when selected, launches the second physical activity tracking function), and the first instance of the first user interface does not include an affordance (e.g., any affordance) associated with the second physical activity tracking function. Updating a list of physical activity tracking functions shown to a user on an initial user interface provides the user with more control of the device by helping the user avoid unintentionally executing physical activity tracking functions and simultaneously reducing the number of steps that a user must take to reach desired physical activity tracking functions. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the first set of affordances includes a fifth affordance (e.g., 1012b) associated with a third physical activity tracking function (e.g., golfing option) different from the first physical activity tracking function and the second physical activity tracking function.

In some examples, the input corresponding to selection of the third affordance causes the second instance of the first user interface to be displayed (in some examples, the input corresponding to selection of the third affordance is the terminal input (e.g., the only input) in the set of one or more inputs).

In some examples, the second instance of the first user interface includes the second affordance.

In some examples, at 1114, the device receives an input (e.g., 1031) corresponding to selection of the second affordance within the second instance of the first user interface.

In some examples, at 1116, in response to receiving the input corresponding to selection of the second affordance within the second instance of the first user interface, the device displays a second instance of the second user interface (e.g., 1024) (e.g., more-workouts interface) that does not include an affordance associated with the second physical activity tracking function.

In some examples, at 1118, while displaying the second instance of the first user interface, the device receives a second set of one or more inputs, the second set of one or more inputs including an input (e.g., 1043) corresponding to the fourth affordance associated with the second physical activity tracking function (e.g., an affordance corresponding to an activity tracking function that was previously added to the user interface) (e.g., a set of inputs corresponding to a request to remove the fourth affordance from the first user interface).

In some examples, in response to receiving the second set of one or more inputs, the device displays a third instance of the first user interface (e.g., 1008 as depicted in FIG. 10N), wherein the third instance of the first user interface does not include an affordance associated with the second physical activity tracking function. Allowing a user to quickly and efficiently remove physical activity tracking functions from a list of physical activity tracking functions provides the user with more control of the device by helping the user avoid unintentionally executing physical activity tracking functions and simultaneously reducing the number of steps that a user must take to reach desired physical activity tracking functions. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, receiving the second set of one or more inputs includes: receiving a swipe gesture (e.g., 1043) corresponding to the fourth affordance and a tap gesture (e.g., 1045) corresponding to a delete affordance (e.g., 1044) associated with the fourth affordance (e.g., a delete affordance that is displayed in response to receiving the swipe gesture).

Note that details of the processes described above with respect to method 1100 (e.g., FIGS. 7A-7B) are also applicable in an analogous manner to the methods described above. For example, methods 700, 800, and 900 optionally includes one or more of the characteristics of the various methods described above with reference to method 1100. For example, deletion of a representation as described in methods 700, 800, and 900 can be performed as described in method 1100.

Figure 12A:
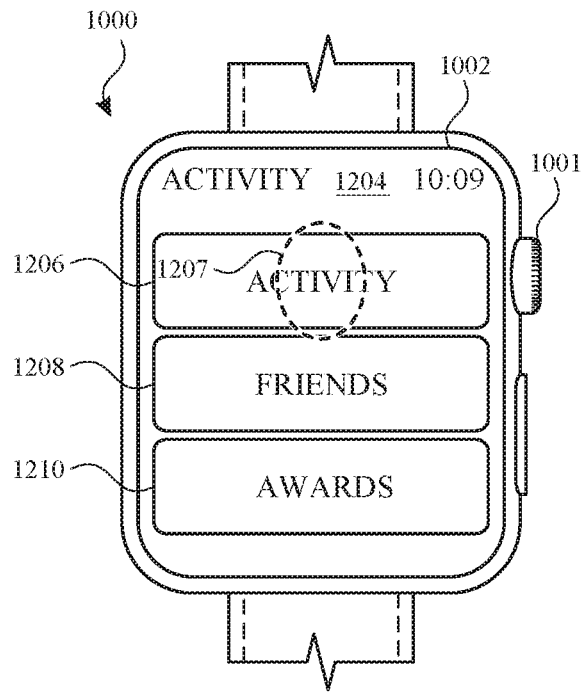
FIG. 12A depicts an electronic device displaying an activity application user interface via a display device 1002.

FIGS. 12A-12F illustrate exemplary user interfaces for displaying awards, in accordance with some embodiments. FIG. 12A depicts electronic device 1000 displaying activity application user interface 1204 via display device 1002. Activity application user interface 1204 includes activity affordance 1206, friends affordance 1208, and awards affordance 1210.

Figure 12B:
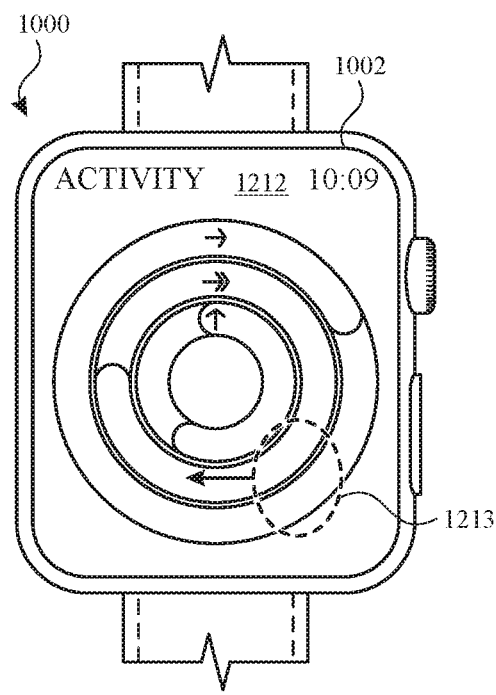
FIG. 12B depicts an electronic device displaying an activity user interface via a display device.
Figure 12C:
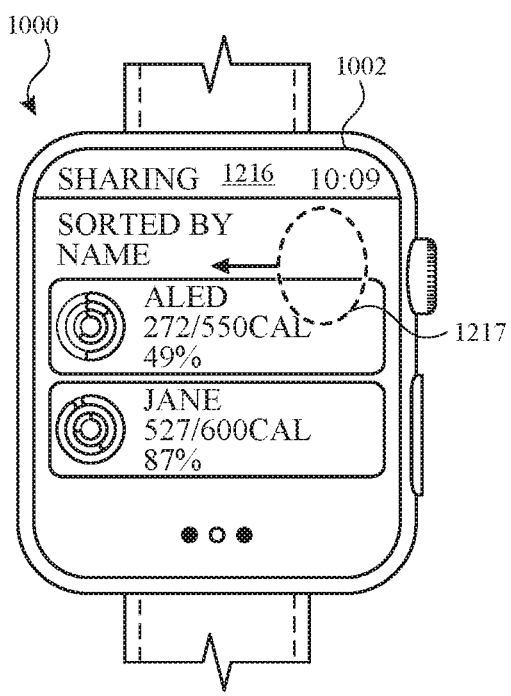
FIG. 12C depicts an electronic device displaying a friends user interface via a display device.
Figure 12D:
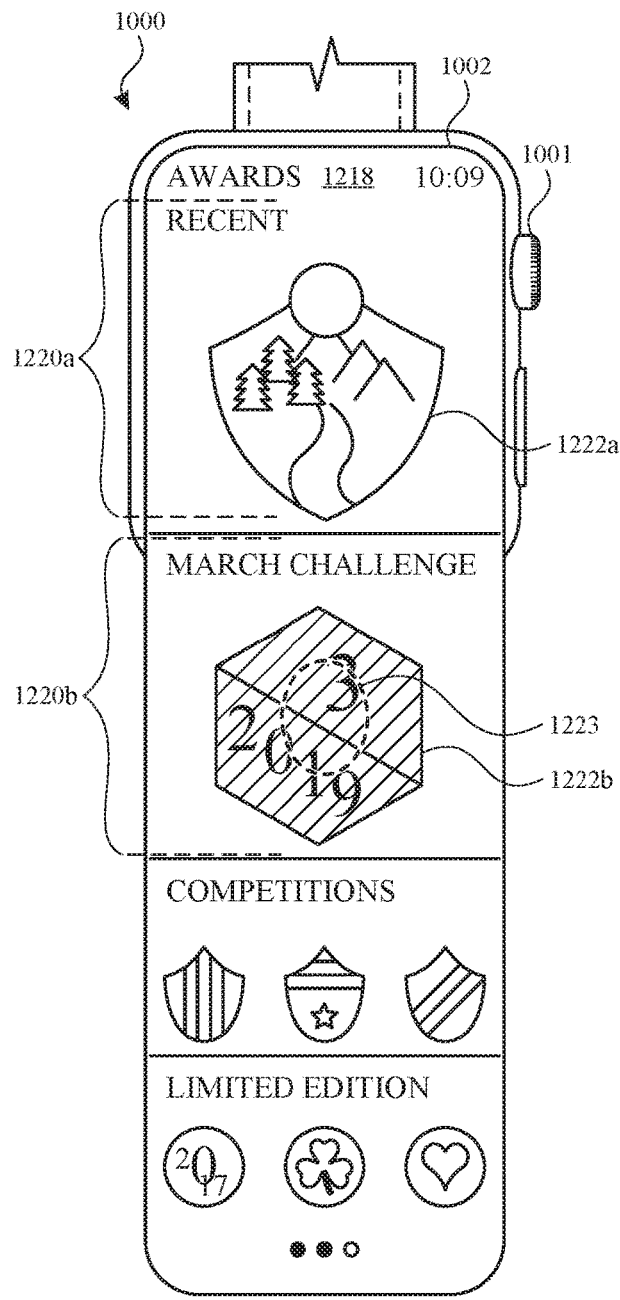
FIG. 12D depicts an electronic device displaying an awards user interface via a display device.

Each of these affordances are configured, when selected, to cause electronic device 1000 to display a user interface corresponding to the respective affordance. For example, activity affordance 1206 corresponds to a user interface for displaying information related to activity of a user associated with electronic device 1000 (as depicted in FIG. 12B). Friends affordance 1208 corresponds to a user interface for managing friends (e.g., users for which are sending data to and/or receiving data from the user associated with electronic device (e.g., sharing)) of the user associated with electronic device 1000 (as depicted in FIG. 12C). Awards affordance 1210 corresponds to a user interface for displaying awards of the user associated with electronic device 1000 (as depicted in FIG. 12D).

Referring to FIG. 12A, electronic device 1000 receives user input 1207 corresponding to selection of activity affordance 1206. User input 1207 can include a touch gesture, such as a tap gesture on activity affordance 1206, causing a user interface associated with activity affordance 1206 to be displayed (e.g., activity user interface 1212).

FIG. 12B depicts electronic device 1000 displaying activity user interface 1212 via display device 1002. Activity user interface 1212 includes information related to activity of a user associated with electronic device 1000 (e.g., three rings, which each ring representing an amount of a different activity metric that the user has completed during a current day).

Referring to FIG. 12B, electronic device 1000 receives user input 1213 corresponding to a swipe gesture. User input 1213 can include a touch gesture, causing a user interface for managing friends to be displayed (e.g., friends user interface 1216 as depicted in FIG. 12C).

FIG. 12C depicts electronic device 1000 displaying friends user interface 1216 via display device 1002. Friends user interface 1212 includes multiple affordances, each affordance corresponding to a user for which the user associated with electronic device 1000 is sharing with.

Referring to FIG. 12C, electronic device 1000 receives user input 1217 corresponding to a swipe gesture. User input 1217 can include a touch gesture, causing a user interface for displaying awards to be displayed (e.g., awards user interface 1218 as depicted in FIG. 12D). In some examples, the swipe gesture depicted in FIG. 12C is determined to be the same direction as the swipe gesture depicted in FIG. 12B. In such examples, if a swipe gesture on friends user interface 1216 is determined to be the opposite direction as the swipe gesture depicted in FIG. 12B, the swipe gesture causes activity user interface 1212 to be displayed.

FIG. 12D depicts electronic device 1000 displaying awards user interface 1218 via display device 1002. Awards user interface 1212 includes multiple sections (e.g., 1220a-1220d), each section including one or more representations of awards corresponding to the respective section. For example, recent section 1220a includes one or more representations of awards that were recently received by the user of electronic device 1000 (e.g., representation 1222a). For another example, March challenge section 1220b includes one or more representations of awards that are associated with a March challenge (e.g., representation 1222b).

A representation of an award can include one or more visual attributes indicating that the award have been awarded to the user of electronic device 1000. For example, representation 1222a can be a first set of one or more colors while representation 1222b can be a second set of one or more colors, the first set of one or more colors indicating that an award corresponding to representation 1222a has been awarded to the user and the second set of one or more colors indicating that an award corresponding to representation 1222b has not been awarded to the user.

Referring to FIG. 12D, electronic device 1000 receives user input 1223 corresponding to selection of representation 1222b. User input 1223 can include a touch gesture, such as a tap gesture on representation 1222*b*, causing a user interface associated with representation 1222*b* to be displayed (e.g., 1224 or 1228).

Figure 12E:
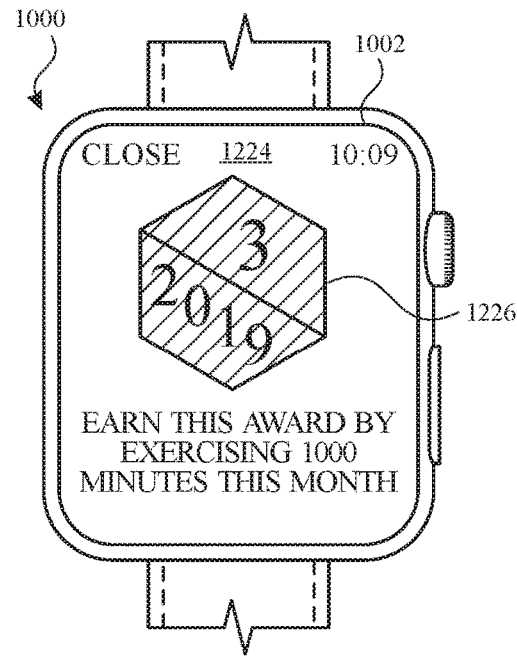
FIG. 12E depicts an electronic device displaying a non-awarded detailed user interface via a display device.

FIG. 12E depicts electronic device 1000 displaying non-awarded detailed user interface 1224 via display device 1002. Non-awarded detailed user interface 1224 corresponds to representation 1222*b* based on user input 1223 corresponding to selection of representation 1222*b*. Non-awarded detailed user interface 1224 includes a representation of representation 1222*b* (e.g., representation 1226). In some examples, representation 1226 is larger than representation 1222*b* (not illustrated). Non-awarded detailed user interface 1224 includes text indicating how the user can earn an award corresponding to representation 1226 ("Earn this award by exercising 1000 minutes this month").

Figure 12F:
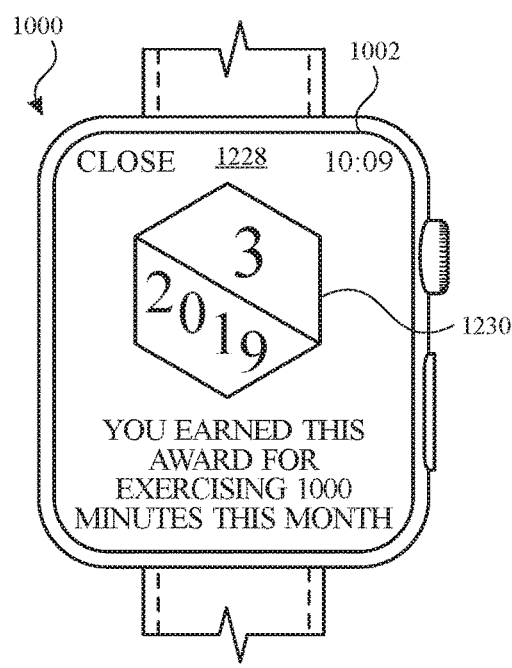
FIG. 12F depicts an electronic device displaying an awarded detailed user interface via a display device.

FIG. 12F depicts electronic device 1000 displaying awarded detailed user interface 1228 via display device 1002. Once an award has been given to the user, a representation corresponding to the award can change. For example, FIG. 12F depicts representation 1230, which corresponds to representation 1226 except that the appearance of representation 1230 is different from representation 1226. In some examples, the different appearance corresponds to representation 1226 being a first set of one or more colors and representation 1230 being a second set of one or more colors different from the first set of one or more colors, the difference indicating that an award corresponding to representation 1230 has been awarded and an award corresponding to representation 1226 has not been awarded.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve tracking of activity and viewing of details related to the activity. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to track activity and view details related to the activity. Accordingly, use of such personal information data enables improved tracking of activity and improved viewing of details related to the activity. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of activity services, the present technology can be configured to allow users to select to "opt in" or "opt out" of participation in the collection of personal information data during registration for services or anytime thereafter. In another example, users can select not to provide activity data for targeted activity services. In yet another example, users can select to limit the length of time activity data is maintained or entirely prohibit the development of trend data. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, activity can be tracked and details related to the activity viewed by inferring preferences based on non-personal information data or a bare minimum amount of personal information, such as the content being requested by the device associated with a user, other non-personal information available to the activity services, or publicly available information.

What is claimed is:

1. An electronic device, comprising:
   a display device;
   one or more processors; and
   memory storing one or more programs configured to be executed by the one or more processors, the one or more programs including instructions for:
      receiving:
         activity data corresponding to a first activity metric for a first time period; and
         activity data corresponding to the first activity metric for a second time period, wherein the first time period is a subset of the second time period;
      receiving a request to display a first user interface; and
      in response to receiving the request, displaying, via the display device, the first user interface including:
         a representation of the activity data corresponding to the first activity metric for the first time period;
         a representation of the activity data corresponding to the first activity metric for the second time period; and
         a representation of a comparison of the activity data corresponding to the first activity metric for the first time period and the activity data corresponding to the first activity metric for the second time period, wherein:
            the representation of the comparison of the activity data indicates one of a negative trend, a neutral trend, and a positive trend for the activity data corresponding to the first activity metric for the first time period as compared to the activity data corresponding to the first activity metric for the second time period; and
            the representation of the comparison of the activity data includes an icon that is separate from the representation of the activity data corresponding to the first activity metric for the first time period and the representation of the activity data corresponding to the first activity metric for the second time period.

2. The electronic device of claim 1, wherein the representation of the activity data corresponding to the first activity metric for the first time period is visually distinct from the representation of the activity data corresponding to the first activity metric for the second time period.

3. The electronic device of claim 1, wherein displaying the first user interface includes:
   displaying an indication for an average of the activity data corresponding to the first activity metric for the first time period; and
   displaying an indication for an average of the activity data corresponding to the first activity metric for the second time period.

4. The electronic device of claim 1, wherein:
   the representation of the activity data corresponding to the first activity metric for the first time period is divided into a first number of representations; and
   the representation of the activity data corresponding to the first activity metric for the second time period is divided into a second number of representations different from the first number of representations.

5. The electronic device of claim 1, wherein the representation of the comparison indicates a difference between the activity data corresponding to the first activity metric for the first time period and the activity data corresponding to the first activity metric for the second time period.

6. The electronic device of claim 1, wherein displaying the first user interface includes:
   displaying a plurality of first-time-period representations for the first time period, wherein:
      a first first-time-period representation corresponds to a length of time,
      a second first-time-period representation corresponds to the length of time,
      the first first-time-period representation corresponds to a third time period within the first time period, and
      the second first-time-period representation corresponds to a fourth time period within the first time period; and
   displaying a plurality of second-time-period representations for the second time period, wherein:
      a first second-time-period representation corresponds to the length of time,
      a second second-time-period representation corresponds to the length of time,
      the first second-time-period representation corresponds to a fifth time period within the second time period,
      the second second-time-period representation corresponds to a sixth time period within the second time period,
      the third time period corresponds to the fifth time period,
      the fourth time period corresponds to the sixth time period,
      the first first-time-period representation is visually paired with the first second-time-period representation, and
      the second first-time-period representation is visually paired with the second second-time-period representation.

7. The electronic device of claim 1, wherein displaying the first user interface includes:
   displaying a representation of a percentage of time periods of a particular length of the activity data corresponding to the first activity metric for the first time period for which the first activity metric met a threshold activity level.

8. The electronic device of claim 1, wherein
   the icon indicates whether a relationship between the activity data corresponding to the first activity metric for the first time period and the activity data corresponding to the first activity metric for the second time period is a first type or a second type.

9. The electronic device of claim 1, wherein:
the electronic device includes a sensor device; and
the activity data corresponding to the first activity metric includes activity data received via the sensor device.

10. The electronic device of claim 1, wherein the activity data corresponding to the first activity metric includes activity data received from a second electronic device.

11. A non-transitory computer-readable storage medium storing one or more programs configured to be executed by one or more processors of an electronic device with a display device, the one or more programs including instructions for:
receiving:
activity data corresponding to a first activity metric for a first time period; and
activity data corresponding to the first activity metric for a second time period, wherein the first time period is a subset of the second time period;
receiving a request to display a first user interface; and
in response to receiving the request, displaying, via the display device, the first user interface including:
a representation of the activity data corresponding to the first activity metric for the first time period;
a representation of the activity data corresponding to the first activity metric for the second time period; and
a representation of a comparison of the activity data corresponding to the first activity metric for the first time period and the activity data corresponding to the first activity metric for the second time period, wherein:
the representation of the comparison of the activity data indicates one of a negative trend, a neutral trend, and a positive trend for the activity data corresponding to the first activity metric for the first time period as compared to the activity data corresponding to the first activity metric for the second time period; and
the representation of the comparison of the activity data includes an icon that is separate from the representation of the activity data corresponding to the first activity metric for the first time period and the representation of the activity data corresponding to the first activity metric for the second time period.

12. The non-transitory computer-readable storage medium of claim 11, wherein the representation of the activity data corresponding to the first activity metric for the first time period is visually distinct from the representation of the activity data corresponding to the first activity metric for the second time period.

13. The non-transitory computer-readable storage medium of claim 11, wherein displaying the first user interface includes:
displaying an indication for an average of the activity data corresponding to the first activity metric for the first time period; and
displaying an indication for an average of the activity data corresponding to the first activity metric for the second time period.

14. The non-transitory computer-readable storage medium of claim 11, wherein:
the representation of the activity data corresponding to the first activity metric for the first time period is divided into a first number of representations; and
the representation of the activity data corresponding to the first activity metric for the second time period is divided into a second number of representations different from the first number of representations.

15. The non-transitory computer-readable storage medium of claim 11, wherein the representation of the comparison indicates a difference between the activity data corresponding to the first activity metric for the first time period and the activity data corresponding to the first activity metric for the second time period.

16. The non-transitory computer-readable storage medium of claim 11, wherein displaying the first user interface includes:
displaying a plurality of first-time-period representations for the first time period, wherein:
a first first-time-period representation corresponds to a length of time,
a second first-time-period representation corresponds to the length of time,
the first first-time-period representation corresponds to a third time period within the first time period, and
the second first-time-period representation corresponds to a fourth time period within the first time period; and
displaying a plurality of second-time-period representations for the second time period, wherein:
a first second-time-period representation corresponds to the length of time,
a second second-time-period representation corresponds to the length of time,
the first second-time-period representation corresponds to a fifth time period within the second time period,
the second second-time-period representation corresponds to a sixth time period within the second time period,
the third time period corresponds to the fifth time period,
the fourth time period corresponds to the sixth time period,
the first first-time-period representation is visually paired with the first second-time-period representation, and
the second first-time-period representation is visually paired with the second second-time-period representation.

17. The non-transitory computer-readable storage medium of claim 11, wherein displaying the first user interface includes:
displaying a representation of a percentage of time periods of a particular length of the activity data corresponding to the first activity metric for the first time period for which the first activity metric met a threshold activity level.

18. The non-transitory computer-readable storage medium of claim 11, wherein
the icon indicates whether a relationship between the activity data corresponding to the first activity metric for the first time period and the activity data corresponding to the first activity metric for the second time period is a first type or a second type.

19. The non-transitory computer-readable storage medium of claim 11, wherein:
the electronic device includes a sensor device; and
the activity data corresponding to the first activity metric includes activity data received via the sensor device.

20. The non-transitory computer-readable storage medium of claim 11, wherein the activity data corresponding to the first activity metric includes activity data received from a second electronic device.

21. A method, comprising:
at an electronic device including a display device:
receiving:
activity data corresponding to a first activity metric for a first time period; and
activity data corresponding to the first activity metric for a second time period, wherein the first time period is a subset of the second time period;
receiving a request to display a first user interface; and
in response to receiving the request, displaying, via the display device, the first user interface including:
a representation of the activity data corresponding to the first activity metric for the first time period;
a representation of the activity data corresponding to the first activity metric for the second time period; and
a representation of a comparison of the activity data corresponding to the first activity metric for the first time period and the activity data corresponding to the first activity metric for the second time period, wherein:
the representation of the comparison of the activity data indicates one of a negative trend, a neutral trend, and a positive trend for the activity data corresponding to the first activity metric for the first time period as compared to the activity data corresponding to the first activity metric for the second time period; and
the representation of the comparison of the activity data includes an icon that is separate from the representation of the activity data corresponding to the first activity metric for the first time period and the representation of the activity data corresponding to the first activity metric for the second time period.

22. The method of claim 21, wherein the representation of the activity data corresponding to the first activity metric for the first time period is visually distinct from the representation of the activity data corresponding to the first activity metric for the second time period.

23. The method of claim 21, wherein displaying the first user interface includes:
displaying an indication for an average of the activity data corresponding to the first activity metric for the first time period; and
displaying an indication for an average of the activity data corresponding to the first activity metric for the second time period.

24. The method of claim 21, wherein:
the representation of the activity data corresponding to the first activity metric for the first time period is divided into a first number of representations; and
the representation of the activity data corresponding to the first activity metric for the second time period is divided into a second number of representations different from the first number of representations.

25. The method of claim 21, wherein the representation of the comparison indicates a difference between the activity data corresponding to the first activity metric for the first time period and the activity data corresponding to the first activity metric for the second time period.

26. The method of claim 21, wherein displaying the first user interface includes:
displaying a plurality of first-time-period representations for the first time period, wherein:
a first first-time-period representation corresponds to a length of time,
a second first-time-period representation corresponds to the length of time,
the first first-time-period representation corresponds to a third time period within the first time period, and
the second first-time-period representation corresponds to a fourth time period within the first time period; and
displaying a plurality of second-time-period representations for the second time period, wherein:
a first second-time-period representation corresponds to the length of time,
a second second-time-period representation corresponds to the length of time,
the first second-time-period representation corresponds to a fifth time period within the second time period,
the second second-time-period representation corresponds to a sixth time period within the second time period,
the third time period corresponds to the fifth time period,
the fourth time period corresponds to the sixth time period,
the first first-time-period representation is visually paired with the first second-time-period representation, and
the second first-time-period representation is visually paired with the second second-time-period representation.

27. The method of claim 21, wherein displaying the first user interface includes:
displaying a representation of a percentage of time periods of a particular length of the activity data corresponding to the first activity metric for the first time period for which the first activity metric met a threshold activity level.

28. The method of claim 21, wherein
the icon indicates whether a relationship between the activity data corresponding to the first activity metric for the first time period and the activity data corresponding to the first activity metric for the second time period is a first type or a second type.

29. The method of claim 21, wherein:
the electronic device includes a sensor device; and
the activity data corresponding to the first activity metric includes activity data received via the sensor device.

30. The method of claim 21, wherein the activity data corresponding to the first activity metric includes activity data received from a second electronic device.

* * * * *